(12) United States Patent
Chin et al.

(10) Patent No.: US 9,901,649 B2
(45) Date of Patent: Feb. 27, 2018

(54) BLOCK COPOLYMERS FOR THERAPEUTIC DRUG DELIVERY

(71) Applicants: INTERNATIONAL BUSINESS MACHINES CORPORATION, Armonk, NY (US); AGENCY FOR SCIENCE, TECHNOLOGY AND RESEARCH, Singapore (SG)

(72) Inventors: Willy Chin, Singapore (SG); Yukti Choudhury, Singapore (SG); Shujun Gao, Singapore (SG); James L. Hedrick, Pleasanton, CA (US); Xiyu Ke, Baltimore, MD (US); Min-Han Tan, Singapore (SG); Jye Yng Teo, Singapore (SG); Yi Yan Yang, Singapore (SG)

(73) Assignees: International Business Machines Corporation, Armonk, NY (US); Agency For Science, Technology and Research, Singapore (SG)

( * ) Notice: Subject to any disclaimer, the term of this patent is extended or adjusted under 35 U.S.C. 154(b) by 0 days.

(21) Appl. No.: 15/145,020

(22) Filed: May 3, 2016

(65) Prior Publication Data
US 2017/0319704 A1    Nov. 9, 2017

(51) Int. Cl.
*A61K 47/60* (2017.01)
*A61K 31/704* (2006.01)
(Continued)

(52) U.S. Cl.
CPC ............ *A61K 47/60* (2017.08); *A61K 9/0019* (2013.01); *A61K 31/704* (2013.01); *A61K 47/58* (2017.08);
(Continued)

(58) Field of Classification Search
None
See application file for complete search history.

(56) References Cited

U.S. PATENT DOCUMENTS 7,186,413 B2    3/2007  Bouhadir et al.
2005/0123596 A1   6/2005  Kohane et al.
(Continued)

OTHER PUBLICATIONS

Ke et al., "pH-sensitive polycarbonate micelles for enhanced intracellular release of anticancer drugs: a strategy to circumvent multidrug resistance", Polymer Chemistry, 5(7), pp. 2621-2628 (2014).*

(Continued)

*Primary Examiner* — Bethany Barham
*Assistant Examiner* — Barbara Frazier
(74) *Attorney, Agent, or Firm* — Michael R. Roberts

(57) ABSTRACT

Amphiphilic block copolymers (BCPs) were prepared comprising a poly(ethylene oxide) block and a biodegradable polycarbonate block functionalized with disulfide groups and carboxylic acid groups. The BCPs form self-assembled micellar particles in aqueous solution that can be loaded with hydrophobic drugs for therapeutic drug delivery. The loaded particles have small particle sizes (<100 nm), narrow particle size distributions, and high drug loading capacity (up to about 50 wt %) based on total dry weight of the loaded particles. Particles loaded with DOX released the DOX in response to changes in pH and glutathione (GSH) redox chemistry. The loaded particles efficiently delivered and released DOX within tumor cells, effectively suppressing growth of the tumor cells at a similar or even lower drug concentration than free DOX. Blank particles containing no DOX did not induce cytotoxicity to cells.

25 Claims, 12 Drawing Sheets

(51) Int. Cl.
    C08G 64/02      (2006.01)
    C08G 64/18      (2006.01)
    A61K 9/00       (2006.01)
    C08G 63/42      (2006.01)
    C08G 63/78      (2006.01)
    A61K 47/58      (2017.01)

(52) U.S. Cl.
    CPC ............ *C08G 63/42* (2013.01); *C08G 63/78* (2013.01); *C08G 64/02* (2013.01); *C08G 64/183* (2013.01)

(56) References Cited

U.S. PATENT DOCUMENTS

| | | |
|---|---|---|
| 2009/0181089 A1 | 7/2009 | Schellekens et al. |
| 2010/0112042 A1 | 5/2010 | Polisky et al. |
| 2011/0065807 A1 | 3/2011 | Radovic-Moreno et al. |
| 2013/0011441 A1 | 1/2013 | Hollinger et al. |
| 2014/0030350 A1 | 1/2014 | Ashrafi et al. |
| 2015/0231077 A1 | 8/2015 | Egusa et al. |
| 2015/0273071 A1 | 10/2015 | Green et al. |

OTHER PUBLICATIONS

Bae, et al., "Design of environment-sensitive supramolecular assemblies for intracellular drug delivery: polymeric micelles that are responsive to intracellular pH change", Angewandte Chemie International Edition, 2003, vol. 42, pp. 4640-4643,.

Chen, et al., "pH and reduction dual-sensitive copolymeric micelles for intracellular doxorubicin delivery", Biomacromolecules, 2011, 12 (10), pp. 3601-3611.

Chin, et al., "Biodegradable Broad-Spectrum Antimicrobial Polycarbonates: Investigating the Role of Chemical Structure on Activity and Selectivity", Macromolecules, (2013), vol. 46, pp. 8797-8807.

Duponte, "Glutathione catalysis and the reaction mechanisms of glutathione-dependent enzymes", Biochimica et Biophysica Acta 1830 (2013) 3217-3266.

Khorsand et al., paper entitled, "Intracellular drug delivery nanocarriers of glutathione-responsive degradable block copolymers having pendant disulfide linkages", published in Biomacromolecules. 2013; 14(6):2103-11 (ISSN: 1526-4602).

Lavasanifara et al., paper entitled, "Poly(ethylene oxide)-block-poly(L-amino acid) micelles for drug delivery", published in the Advanced Drug Delivery Reviews 54 (2002) 169-190.

Meng et al., paper entitled, "Intracellular drug release nanosystems", published in Materials Today, vol. 15, Issue 10, Oct. 2012, pp. 436-442.

Pratt, et al., "Exploration, Optimization, and Application of Supramolecular Thiourea-Amine Catalysts for the Synthesis of Lactide (Co)polymers", Macromolecules, (2006), vol. 39, pp. 7863-7871.

Sun, et al., "Biodegradable micelles with sheddable poly(ethylene glycol) shells for triggered intracellular release of doxorubicin", Biomaterials, (2009), vol. 30, 31, pp. 6358-6366.

Tang, et al., "Shell-detachable micelles based on disulfide-linked block copolymer as potential carrier for intracellular drug delivery", Bioconjugate Chemistry, (2009), 20, pp. 1095-1099.

Wen, et al., "Rapidly disassembling nanomicelles with disulfide-linked PEG shells for glutathione-mediated intracellular drug delivery", Chemical Communications, 2011, 47, pp. 3550-3552.

Yang, et al., "Supramolecular nanostructures designed for high cargo loading capacity and kinetic stability", Nano Today, (2010), vol. 5, pp. 515-523.

Zhou et al., paper entitled, "Endosomal pH-activatable poly(ethylene oxide)-graft-doxorubicin prodrugs: synthesis, drug release, and biodistribution in tumor-bearing mice", published in Biomacromolecules 2011, 12, 1460-1467.

* cited by examiner

BLOCK COPOLYMERS FOR THERAPEUTIC DRUG DELIVERY

PARTIES TO A JOINT RESEARCH AGREEMENT

This invention was made under a joint research agreement between International Business Machines Corporation and the Agency For Science, Technology and Research.

BACKGROUND

The present invention relates to block copolymers for therapeutic drug delivery, and more specifically, to block copolymers having dual-response release properties for drug delivery.

Cancer is one of the most prevalent public health concerns in many parts of the world. As one of the key treatments in medical oncology, chemotherapy is the most effective treatment for metastatic tumors and is always used in conjunction with other cancer treatments such as radiation therapy and surgery to increase success rate of eradicating tumor cells. Unfortunately, multidrug resistance is a major factor in failures of chemotherapy, where only a small portion of drug-sensitive cells are killed and a larger portion of tumor cells are left behind to become resistant. While the exact mechanisms in which tumor cells develop resistance are yet to be clearly understood, resistance to therapy has been highly associated with the development of molecular "pumps" in the tumor membranes that actively pump out the chemotherapeutic drugs, preventing the toxic effects of drugs from harming the cells. Moreover, many of these drugs are cytotoxic to healthy cells. This led to the development of tumor-targeting drug delivery systems using chemotherapeutic drugs.

Amongst the nano-drug delivery systems, micelles self-assembled from amphiphilic block copolymers are of interest. This is due to the several beneficial characteristics of polymer-based micelles over other types of nano-carriers, including liposomes: i) small size (10-100 nm) and a reasonably low polydispersity index and ii) a combination of hydrophobic core for efficient loading of hydrophobic drugs and a hydrophilic shell for enhanced stability in aqueous environments. Furthermore, research studies have demonstrated that drug-loaded polymer-based micelles can have increased blood circulation time and can accumulate at higher concentrations in the tumor tissues compared to normal tissues due to the enhanced permeability and retention effect (EPR effect).

Several chemotherapeutic drug-loaded biodegradable polymer-based micelles have undergone different phases of clinical trials in various countries. For instance, phase I clinical trials of NK012, an SN-38-loaded micelle based on biodegradable poly(ethylene glycol)-poly(glutamic acid) block copolymer, have been approved and are now in Phase II clinical trials for the treatment of colorectal cancer in Japan as well as breast cancer and small cell lung cancer in the USA. GENEXOL-PM, a biodegradable micelle based on poly(ethylene glycol)-poly(D,L-lactide) copolymer loaded with paclitaxel, has achieved FDA approval for use in patients with breast cancer.

Different tissues and cellular compartments have varying pH values. For example, the normal extracellular matrix and blood have a pH of about 7.4, while the tumor extracellular environment is more acidic at approximately 6.5 due to low oxygen supply in the intercellular environment. The pH in endosomes and lysosomes are even lower at 5.0 to 5.5. By utilizing variations in these pH values, pH-responsive polymer-based micelles have been constructed to target tumor tissues and/or cells. For instance, BAE, et al., Angewandte Chemie International Edition, 2003, volume 42, pages 4640-4643, conjugated DOX to a poly(ethylene glycol)-polyaspartate block copolymer through an acid sensitive hydrazone bond, and CHEN, et al., Biomacromolecules, 2011, 12 (10), pages 3601-3611, employed acetals as acid-cleavable linkages for poly(ethylene glycol)-polycarbonate block copolymer. Both studies demonstrated a significantly faster release of antitumor drugs at the endosomal pH than at physiological pH.

Glutathione (GSH) is a thiol-containing tripeptide generated in the cellular cytoplasm that is capable of reducing a disulfide bond, forming two thiol groups. The concentrations of GSH of the intracellular compartments and the extracellular environment differ significantly. The intracellular concentration of GSH is in the millimolar range (~2-10 mM) whereas the concentration of GSH in the extracellular fluids is in the micromolar range (~2-10 μM). In addition, it has been reported that tumor cells generally contain elevated concentrations of intracellular GSH, several fold higher than that of normal cells. The diversity in the redox potentials between intracellular and extracellular compartments has led to development of GSH-responsive micellar delivery of antitumor drugs. For example, WEN, et al., Chemical Communications, 2011, 47, pp 3550-3552, prepared reductively degradable micelles from poly(ε-benzyloxycabonly-L-lysine) with disulfide-linked poly(ethylene glycol). In vitro release studies revealed that DOX release increased by almost 4-fold in 10 mM GSH as compared to one without GSH in a period of 36 hours. TANG et al., Bioconjugate Chemistry, (2009), 20, pp 1095-1099 showed that shell-detachable micelles based on disulfide-linked block copolymer of poly(ε-caprolactone) and poly(ethyl ethylene phosphate) efficiently released DOX under GSH and enhanced growth inhibition of glutathione monoester pre-treated A549 tumor cells. SUN et al., Biomaterials, (2009), volume 30, 31, pp 6358-6366 reported that shell-sheddable micelles prepared from copolymer of poly(ε-caprolactone) and poly(ethylene glycol) released DOX significantly faster inside RAW 264.7 cells and gave a higher anti-tumor efficacy as compared to the reduction insensitive control.

Although progress in micellar drug delivery has been made in the past decade, a need persists to improve the therapeutic benefits of these systems. Ongoing issues include poor target specificity of therapeutic drugs, and lethargic drug release at tumor sites and/or in the tumor cells. Polymer-based micelles having improved drug loading capacity and kinetic stability can be deficient in their ability to release the drugs and/or deliver a therapeutic cargo at a desired location. Non-toxic, biodegradable and/or biocompatible polymers are needed that have improved drug release characteristics, particularly in the cytoplasmic environment.

SUMMARY

Accordingly, a block copolymer (BCP) is disclosed, comprising:
   i) a hydrophilic block A having a structure according to formula (A-1):

(A-1)

wherein m represents average degree of polymerization (DP), and m has a value greater than 1; and
ii) a block B which comprises an aliphatic carbonate repeat unit of formula (A-2):

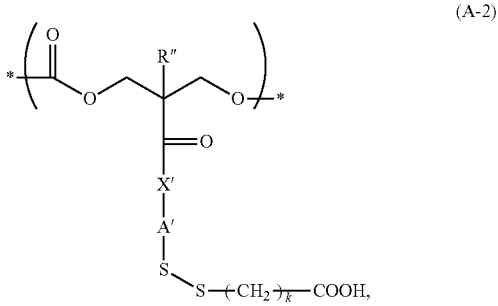

(A-2)

wherein
k is a positive integer having a value of 2-10,
A' is a divalent hydrocarbon linking group comprising 2-10 carbons,
R" is a monovalent radical selected from the group consisting of hydrogen, methyl, ethyl, and propyl, and
X' is *—O—* or *—NH—*;
wherein
the BCP is a linear block copolymer,
block B is a polycarbonate chain or a polyestercarbonate chain, and
an end repeat unit of block A is directly or indirectly covalently linked to an end repeat unit of block B.
Also disclosed is a composition, comprising:
water; and
loaded particles dispersed in the water, wherein each of the loaded particles comprises two or more macromolecules of the BCP of claim 1 and a therapeutic agent for a medical treatment, the BCP and the therapeutic agent bound by non-covalent interactions;
wherein
the therapeutic agent is selected from the group consisting of genes, proteins, peptides, drugs, and combinations thereof,
the loaded particles have an average cross-sectional circular diameter of about 10 nm to about 500 nm, and
the loaded particles are capable of releasing the therapeutic agent in response to a change in pH and/or reaction with a disulfide reducing agent.
Further disclosed is a method, comprising:
preparing an initial block copolymer by organocatalyzed ring opening polymerization (ROP) of a cyclic carbonate monomer comprising a pendent leaving group, the ROP initiated by a polymeric initiator comprising a poly(ethylene oxide) chain, the initial block copolymer comprising a poly(ethylene oxide) chain designated block A and a second block comprising an aliphatic carbonate repeat unit comprising a sidechain leaving group, wherein an end repeat unit of block A is directly or indirectly covalently linked to an end repeat unit of the second block;
treating the initial block copolymer with a compound comprising a thiosulfonate anion, thereby forming a modified block copolymer by nucleophilic substitution of the leaving group by the thiosulfonate anion, the modified block copolymer comprising a carbonate repeat unit comprising a sidechain thiosulfonate group; and treating the modified block copolymer with a compound comprising a thiol group and a carboxylic acid group, thereby forming a block copolymer (BCP) comprising block A and a block B;
wherein
block B is a polycarbonate chain or a polyestercarbonate chain, and
block B comprises an aliphatic carbonate repeat unit comprising a disulfide group and a carboxyl acid group.
The above-described and other features and advantages of the present invention will be appreciated and understood by those skilled in the art from the following detailed description, drawings, and appended claims.

DETAILED DESCRIPTION

Figure 1:
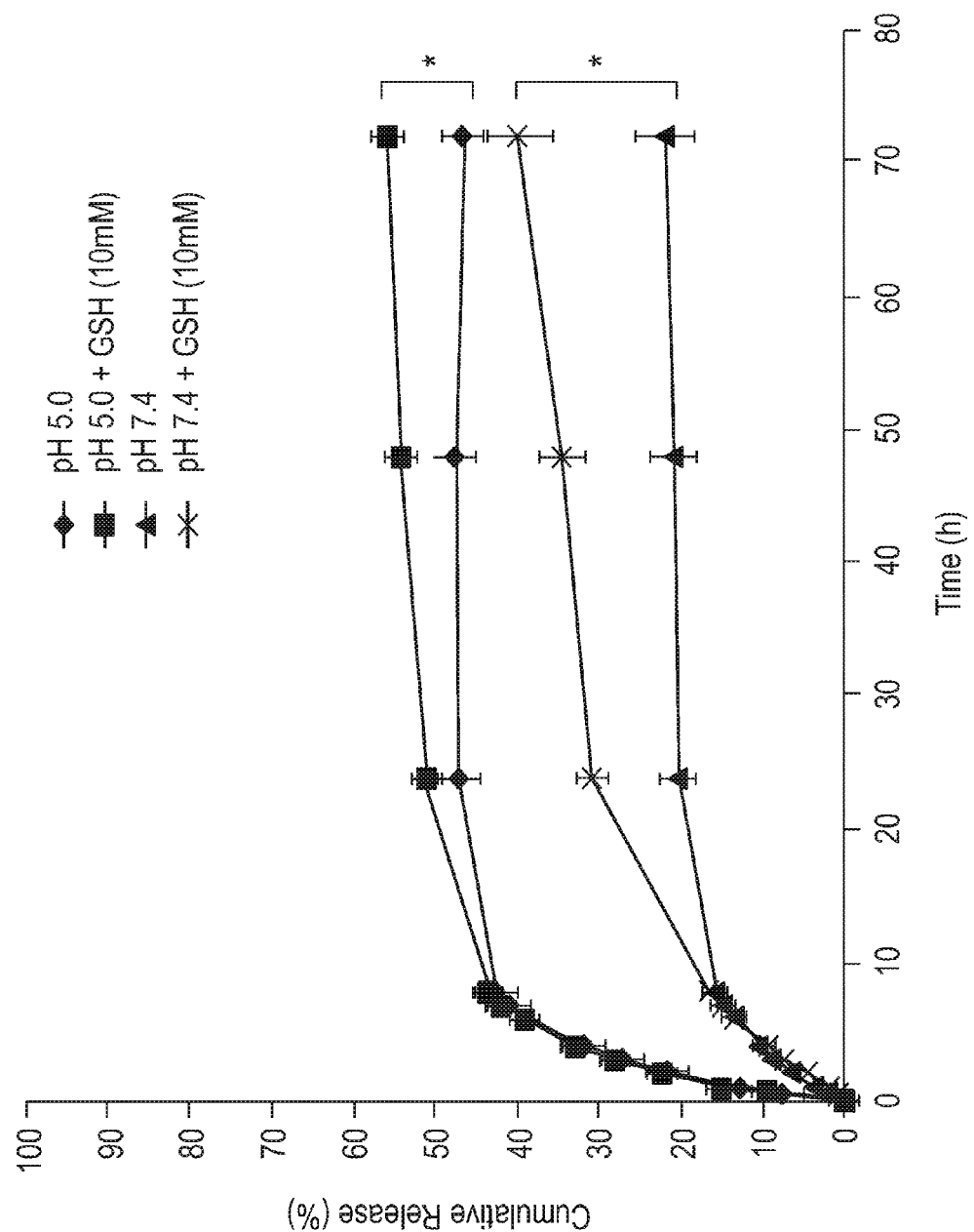
FIG. 1 is a graph showing the time-dependent cumulative release of DOX from loaded-particles LM-1 at pH 5.0 and 7.4, with and without GSH (mean±standard deviation, n=3, P value<0.05 at each pH).

Disclosed are amphiphilic block copolymers (BCPs) that self-assemble in aqueous solution to form nano-sized particles (i.e., micelles) useful for drug delivery applications.

The particles comprise two or more macromolecules of the BCP bound by non-covalent interactions (e.g., hydrogen bonding, hydrophobic interactions). The particles have hydrophilic surfaces and a hydrophobic cores, and are dispersible in aqueous solution as discrete particles. The BCPs comprise a poly(ethylene oxide) block, designated block A, and a polycarbonate block or polyestercarbonate block, designated block B. Block B comprises an aliphatic carbonate repeat unit having a polymer backbone portion and a pendent sidechain portion linked to the polymer backbone. The sidechain portion comprises a carboxylic acid group and a disulfide group. When self-assembly occurs in solution in the presence of a therapeutic agent for a medical treatment (e.g., a cancer drug), a nano-sized "loaded particle" can form that comprises the BCP and the therapeutic agent bound by non-covalent interactions. Herein, the self-assembled BCP is also referred to as a "carrier" of the therapeutic agent, and the therapeutic agent is also referred to as the "cargo". The loaded particles are capable of delivering a cargo to a target cell (e.g., cancer cell), transporting the cargo through the cell membrane, and releasing the cargo within the cell interior in response to a change in pH (e.g., as in the acidic endosomal environment) and/or by reaction with an intracellular reducing agent capable of cleaving a disulfide bond, forming two thiol groups. The reaction is illustrated below using glutathione (GSH), an intracellular reducing agent of disulfides.

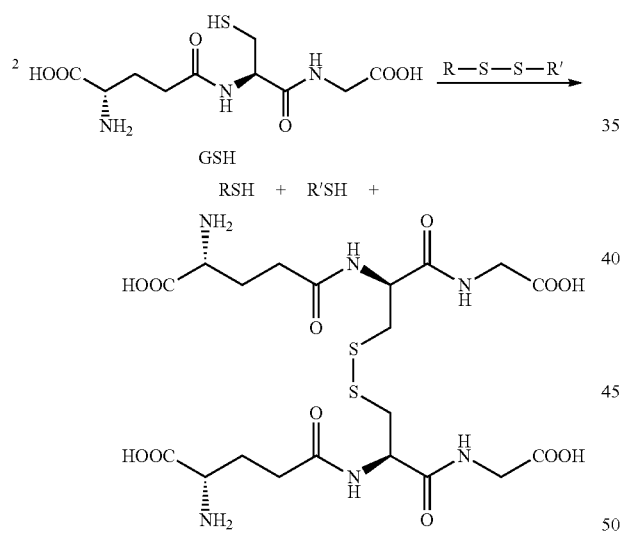

Herein, a polycarbonate chain consists of carbonate repeat units, whereas a polyestercarbonate chain consists of ester repeat units and carbonate repeat units. A polycarbonate chain can be formed by ring opening polymerization of one or more cyclic carbonate monomers. A polyestercarbonate chain can be formed by ring opening polymerization of a mixture containing a cyclic carbonate monomer and a cyclic ester monomer.

The BCP is a linear polymer. Herein, a linear polymer has one polymer branch rather than intersecting polymer branches, and the one polymer branch has two peripheral dangling ends (i.e., the BCP is not a macrocycle). The polymer branch can comprise two or three polymer blocks, wherein adjacent polymer blocks have distinct chemical compositions. Respective end repeat units of adjacent polymer blocks are linked by a divalent linking group, which can be a single bond or a group comprising 0-20 carbons.

The BCP has a polymer backbone that consists of the collection of covalently linked atomic centers providing the shortest path of covalent bonds from the most peripheral repeat unit at a first end of the block copolymer to the most peripheral repeat unit at an opposing end of the block copolymer chain. The BCP backbone includes atomic centers of any linking groups joining adjacent polymer blocks, which are part of the shortest path of covalent bonds. The BCP backbone can include carbon atomic centers (backbone carbons), oxygen atomic centers (backbone oxygens), nitrogen atomic centers (backbone nitrogens), and so on.

As an example, the block copolymer DSP-1 has the following structure.

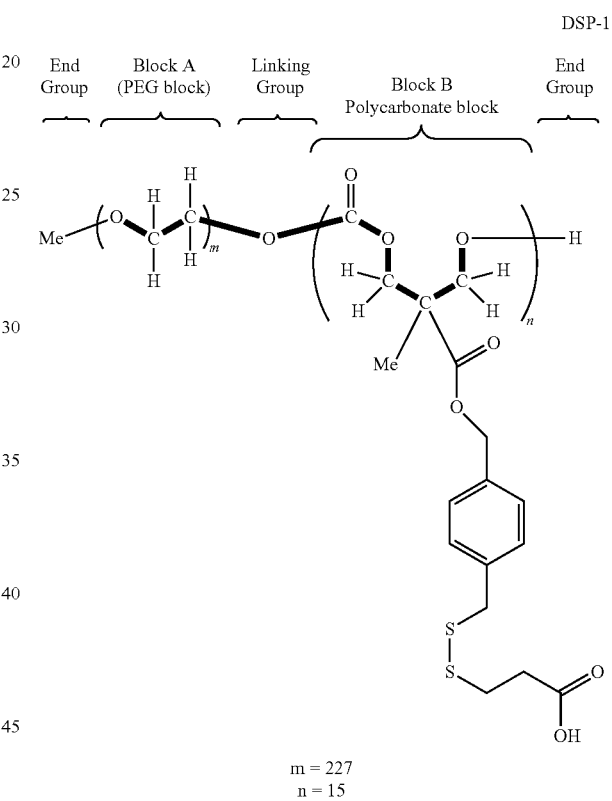

$m = 227$
$n = 15$

DSP-1 has a poly(ethylene oxide) block (block A, also referred to as "PEG block") and a polycarbonate block (block B) linked by a divalent linking group (*—O—*). The atomic centers of the BCP backbone are shown in bold font linked by bold bonds. The oxygen of the linking group is an atomic center of the block copolymer backbone. Herein, the hydrogens that are linked to backbone carbons of block A and block B are not atomic centers of the BCP backbone. Likewise, the carbonyl oxygen of the carbonate group of block B is not an atomic center of the BCP backbone. Additionally, the sidechain methyl group of block B and the sidechain ester group of block B contain no atomic centers of the BCP backbone. Additionally, the methyl end group and the hydrogen end group contain no atomic centers of the BCP backbone.

Each polymer block has a backbone (e.g., block A backbone, block B backbone, and so on), which is a portion of the BCP backbone. The atomic centers of the PEG block that are part of the BCP backbone are referred to as the block A backbone. The atomic centers of the polycarbonate block that are part of the BCP backbone are referred to as the block B backbone.

The BCPs can be biodegradable and/or biocompatible. The term "biodegradable" is defined by the American Society for Testing and Materials as degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

A "biocompatible" material is defined herein as a material capable of performing with an appropriate host response in a specific application.

Herein, "restricted metals" include ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium.

Each one of the foregoing restricted metals can have a concentration in the BCP of 0 parts to 100 ppm (parts per million), 0 parts to 100 ppb (parts per billion), or 0 parts to 100 ppt (parts per trillion). Preferably, each one of the foregoing restricted metals has a concentration of 0 parts in the BCP (i.e., the concentration is below detection limits). In an embodiment, the chemical formulas of the components used in the ring opening polymerization (ROP), including the cyclic carbonyl monomers (i.e., cyclic carbonates, cyclic esters), the ROP initiator, the catalyst for the ring opening polymerization, the solvent, and any base accelerator, contain none of the above restricted metals. A therapeutic agent can comprise a restricted metal.

No restriction is placed on the concentration of boron, silicon, or any individual alkali metal in the disclosed BCPs and/or compositions thereof.

The BCPs can be non-toxic. Preferably, the BCPs have an intravenous LD50 value of 500 mg/kg or more. Herein, intravenous LD50 of a substance refers to the median lethal intravenous dosage in milligrams of the substance per kilogram of a test mammal's (e.g., mouse) body mass that kills 50% of the test mammal population in a specified time period.

Diblock Copolymers (A-B type)

The BCP can be an A-B-type diblock copolymer. This type of BCP comprises a hydrophilic polymer block (block A), which is a poly(ethylene oxide) chain, and a second polymer block (block B), which is a polycarbonate chain or a polyestercarbonate chain.

The poly(ethylene oxide) chain of block A has the structure of formula (A-1):

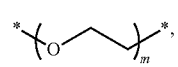

wherein
m represents average degree of polymerization (DP), and m has a value greater than 1.

Preferably, m has a value of about 100 to about 300. Block A is also referred to herein as a PEG block after a poly (ethylene glycol) (PEG) material, which can be used in the preparation of the BCP.

Herein, an atomic center shown linked to an asterisk (a starred bond) indicates the atomic center is covalently linked to another atomic center of the chemical structure represented by the asterisk. For example, the oxygen of (A-1), which is shown linked to an asterisk, can be linked to an atomic center of an end group, a linking group, or another repeat unit of block B. The methylene carbon having a starred bond of (A-1) can be linked to an atomic center of an end group, a linking group, or another repeat unit of block B.

Block B comprises an aliphatic carbonate repeat unit having a sidechain portion pendent to the block B backbone. The sidechain comprises a disulfide group and a carboxyl acid group. In an embodiment, the aliphatic carbonate repeat unit of block B has a structure in accordance with formula (A-2):

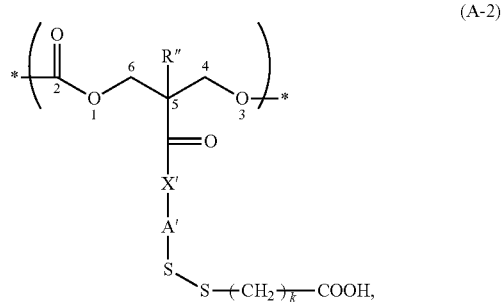

wherein
atomic centers of the polymer backbone are numbered 1-6,
k is a positive integer having a value of 2-10,
A' is a divalent hydrocarbon linking group comprising 2-10 carbons,
R" is a monovalent radical selected from the group consisting of hydrogen, methyl, ethyl, and propyl, and
X' is *—O—* or *—NH—*.

The carboxylic acid group provides a pH switch for releasing the therapeutic agent. The disulfide group provides a redox switch for releasing the therapeutic agent. In an embodiment, X' is *—O—* (i.e., the pendent side chain comprising the disulfide group is an ester group, wherein the ester portion has a terminal carboxylic acid group, and the ester carbonyl group is directly linked to the block B polymer backbone).

Exemplary non-limiting A' groups include those of Scheme 1.

Scheme 1

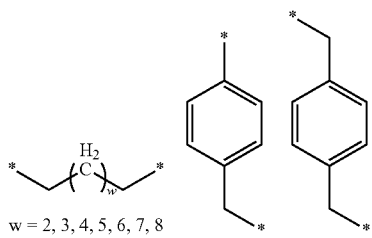

w = 2, 3, 4, 5, 6, 7, 8

Block B can be a homopolymer or random copolymer chain comprising the aliphatic carbonate repeat unit of formula (A-2). Block B can comprise other aliphatic carbonate repeat units and/or aliphatic ester repeat units (e.g., an ester repeat unit formed by ring opening polymerization of lactide). Block B can have an average degree of polymerization (DP) between 1 and 100, more preferably between 5 and 50, and even more preferably about 10 to about 20.

More specific examples of carbonate repeat units of formula (A-2) include those of Scheme 2.

Scheme 2

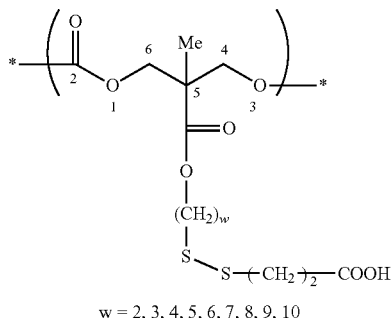

w = 2, 3, 4, 5, 6, 7, 8, 9, 10

In an embodiment, block B is a polycarbonate chain having a structure according to formula (A-3):

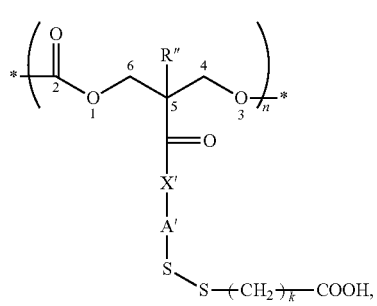

(A-3)

wherein
  atomic centers of the polymer backbone of block B are numbered 1-6,
  n represents average degree of polymerization, and n has a value between 1 and 100,
  each k is an independent positive integer having a value of 2-10,
  each A' is an independent divalent hydrocarbon group comprising 2-10 carbons,
  each R" is an independent monovalent radical selected from the group consisting of hydrogen, methyl, ethyl, and propyl, and
  each X' is an independent member of the group consisting of *—O—* and *—NH—*.

A more specific block B is a polycarbonate chain of formula (A-4):

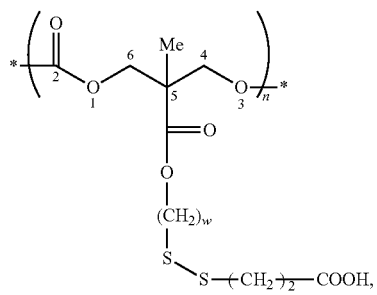

(A-4)

wherein
  atomic centers of the polymer backbone of block B are numbered 1-6,
  each w is an independent positive integer having a value of 2-10, and
  n represents average degree of polymerization, and n has a value between 1 and 100.

Another more specific block B is a homopolycarbonate chain of formula (A-5):

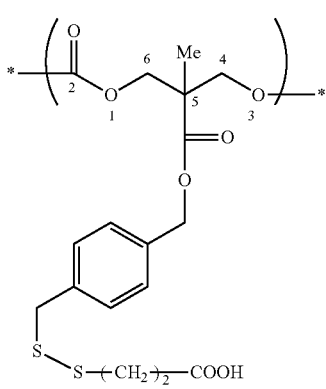

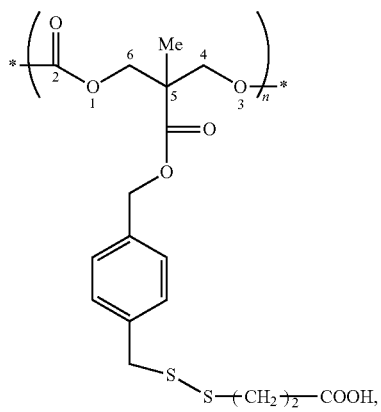

(A-5)

wherein
- atomic centers of the polymer backbone of block B are numbered 1-6, and
- n represents average degree of polymerization, and n has a value between 1 and 100.

An end repeat unit of block A is directly or indirectly covalently linked to an end repeat unit of block B. More specifically, block A and block B are covalently linked to a divalent linking group L', which can be a single bond or a group comprising 0-20 carbons. No restriction is placed on the structure of L', with the proviso that the self-assembly properties of the BCP in water, cargo loading properties of the BCP, and cargo release properties of the BCP are not adversely affected. Non-limiting L' groups include divalent heteroatoms (e.g., *—O—*, *—S—*), amine groups (e.g., *—N(H)—*, *—N(R)—*, wherein R is a monovalent $C_1$-$C_6$ hydrocarbon group), carbonyl-containing groups (e.g., *—C(=O)—*, *—C(=O)O—*, *—C(=O)NH—*), and alkyleneoxy groups (e.g., *—CH$_2$CH$_2$O—*).

The diblock copolymer comprises a first end group E', which is linked to a most peripheral end repeat unit of block A. The diblock copolymer comprises a second end group E", which is linked to a most peripheral end repeat unit of block B. No restriction is placed on E' and E", with the proviso that the self-assembly properties of the BCP in water, cargo loading properties of the BCP, and cargo release properties of the BCP are not adversely affected. As non-limiting examples, E' and/or E" can be a member of the group consisting of hydrogen, $C_1$-$C_{10}$ hydrocarbyl groups (e.g., methyl, ethyl, phenyl, benzyl), aryloxy groups (e.g., phenoxy), $C_1$-$C_{10}$ alkoxy groups (e.g., methoxy, ethoxy), and $C_1$-$C_{10}$ acyl groups (e.g., acetyl, propionyl, benzoyl)

More specific A-B-type BCPs have structures in accordance with formula (A-6):

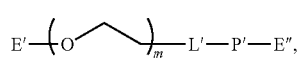

(A-6)

wherein
- m represents average degree of polymerization, and m has a value between 1 and 300,
- E' is a first end group,
- E" is a second end group,
- L' is a single bond or a divalent linking group comprising 0-20 carbons, and
- P' is a polycarbonate or polyestercarbonate chain comprising a carbonate repeat unit of formula (A-2).

Other more specific A-B-type BCPs have structures in accordance with formula (A-7):

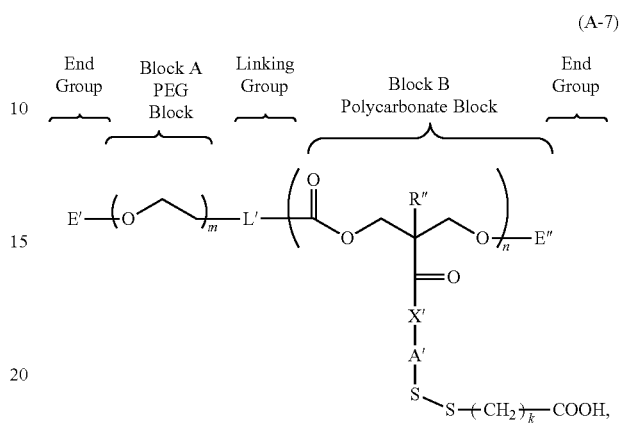

(A-7)

wherein
- m represents average degree of polymerization, and m has a value between 1 and 300,
- n represents average degree of polymerization, and n has a value between 1 and 100,
- each k is an independent positive integer having a value of 2-10,
- each A' is an independent divalent hydrocarbon group comprising 2-10 carbons,
- E' is a first end group,
- E" is a second end group,
- L' is a single bond or a divalent linking group comprising 0-20 carbons,
- each R" is an independent monovalent radical selected from the group consisting of hydrogen, methyl, ethyl, and propyl, and
- each X' is an independent member of the group consisting of *—O—* and *—NH—*.

Still more specific A-B-type BCPs have structures in accordance with formula (A-8):

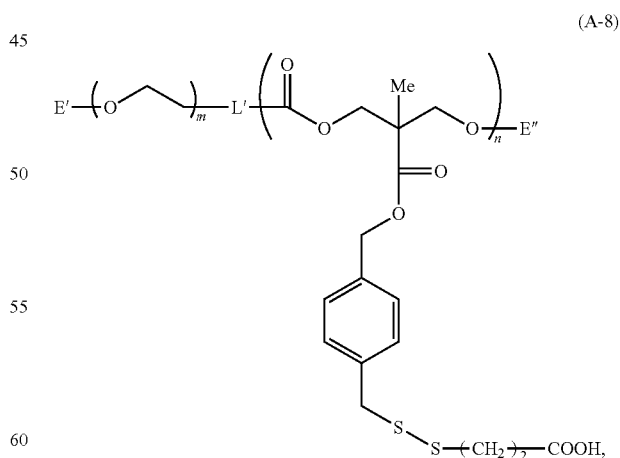

(A-8)

wherein
- m represents average degree of polymerization, and m has a value between 1 and 300,
- n represents average degree of polymerization, and n has a value between 1 and 100, E' is a first end group,
E" is a second end group, and
L' is a single bond or a divalent linking group comprising 0-20 carbons.

In an embodiment, E' is methyl or ethyl, E" is hydrogen, and L' is *—O—*. Preferably, in the above structures m has an average value of about 100 to about 300, and n has an average value of about 10 to about 20.

Triblock Copolymers (B-A-B' type)

The block copolymer can be a linear triblock copolymer of the B-A-B' type. This BCP comprises a divalent central block A of formula (A-1) which is directly or indirectly covalently linked to a block B and a block B'. Block B and block B' are independent blocks. Block B can be a polycarbonate chain or a polyestercarbonate chain comprising the carbonate repeat unit of formula (A-2). Block B' can be a polycarbonate chain or a polyestercarbonate chain comprising the carbonate repeat unit of formula (A-2). In an embodiment, block B and block B' have the same chemical structure.

More specific B-A-B' type triblock copolymers have structures in accordance with formula (A-9):

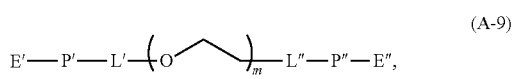

(A-9)

wherein
m represents average degree of polymerization, and m has a value between 1 and 300,
the poly(ethylene oxide) chain is designated block A,
E' is a first end group,
E" is a second end group,
L' is a single bond or a divalent linking group comprising 0-20 carbons,
L" is a single bond or a divalent linking group comprising 0-20 carbons, of a divalent linking group L". No restriction is placed on the structure of L' and L", with the proviso that the self-assembly properties of the BCP in water, cargo loading properties of the BCP, and cargo release properties of the BCP are not adversely affected. L' can be a single bond or a $C_0$-$C_{20}$ group. Non-limiting L' groups include divalent heteroatoms (e.g., *—O—*, *—S—*), amine groups (e.g., *—N(H)—*, *—N(R)—*, wherein R is a monovalent $C_1$-$C_6$ hydrocarbon group), carbonyl-containing groups (e.g., *—C(=O)—*, *—C(=O)O—*, *—C(=O)NH—*), and alkyleneoxy groups (e.g., *—CH$_2$CH$_2$O—*). L" can be a single bond or a $C_0$-$C_{20}$ group. Non-limiting L" groups include divalent heteroatoms (e.g., *—O—*, *—S—*), amine groups (e.g., *—N(H)—*, *—N(R)—*, wherein R is a monovalent $C_1$-$C_6$ hydrocarbon group), carbonyl-containing groups (e.g., *—C(=O)—*, *—C(=O)O—*, *—C(=O)NH—*), and alkyleneoxy groups (e.g., *—CH$_2$CH$_2$O—*).

The B-A-B'-type triblock copolymers comprise a first end group E', which is linked to a peripheral end repeat unit of block B, and a second end group E", which is linked to a peripheral end repeat unit of block B'. No restriction is placed on E' and E", with the proviso that the self-assembly properties of the BCP in water, cargo loading properties of the BCP, and cargo release properties of the BCP are not adversely affected. As non-limiting examples, E' and/or E" can be a member of the group consisting of hydrogen, $C_1$-$C_{10}$ hydrocarbyl groups (e.g., methyl, ethyl, phenyl, benzyl), aryloxy groups (e.g., phenoxy), $C_1$-$C_{10}$ alkoxy groups (e.g., methoxy, ethoxy), and $C_1$-$C_{10}$ acyl groups (e.g., acetyl, propionyl, benzoyl)

In an embodiment, L' is a single bond, L" is a heteroatom *—O—*, E' is hydrogen and E" is hydrogen. In another embodiment, P' and P" are polycarbonate chains of formula (A-3).

Still more specific B-A-B'-type triblock copolymers have structures in accordance with formula (A-10):

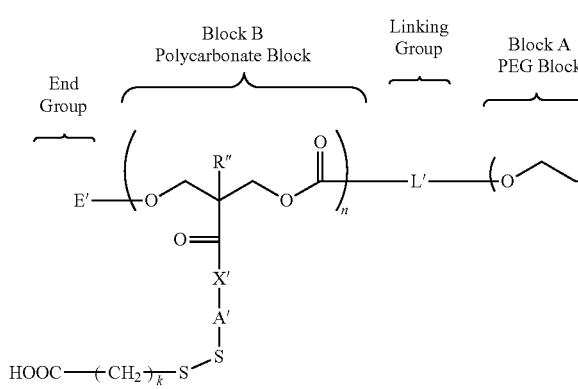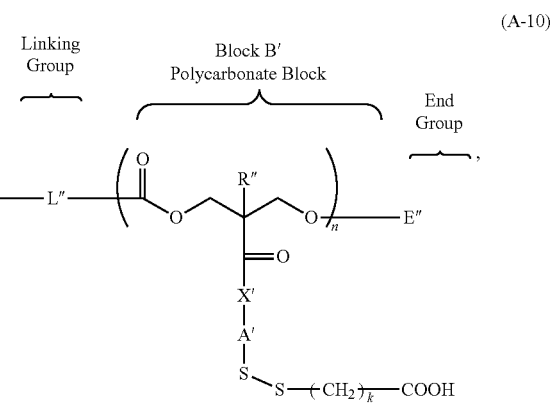

(A-10)

P' is a polycarbonate or polyestercarbonate chain (block B) comprising a carbonate repeat unit of formula (A-2), and
P" is another polycarbonate or polyestercarbonate chain (block C) comprising a carbonate repeat unit of formula (A-2).

A first end repeat unit of central block A is covalently linked to an end repeat unit of block B by way of a divalent linking group L'. A second end repeat unit of block A is covalently linked to an end repeat unit of block B' by way wherein
m represents average degree of polymerization, and m has a value between 1 and 300,
n represents average degree of polymerization, and n has a value between 1 and 100,
n' represents average degree of polymerization, and n' has a value between 1 and 100,
each k is an independent positive integer having a value of 2-10, each A' is an independent divalent hydrocarbon group comprising 2-10 carbons,
E' is a first end group,
E" is a second end group,
L' is a single bond or a divalent linking group comprising 0-20 carbons,
L" is a single bond or a divalent linking group comprising 0-20 carbons,
each R" is an independent monovalent radical selected from the group consisting of hydrogen, methyl, ethyl, and propyl, and
each X' is an independent member of the group consisting of *—O—* and *—NH—*.

Still more specific B-A-B'-type triblock copolymers have structures in accordance with formula (A-11):

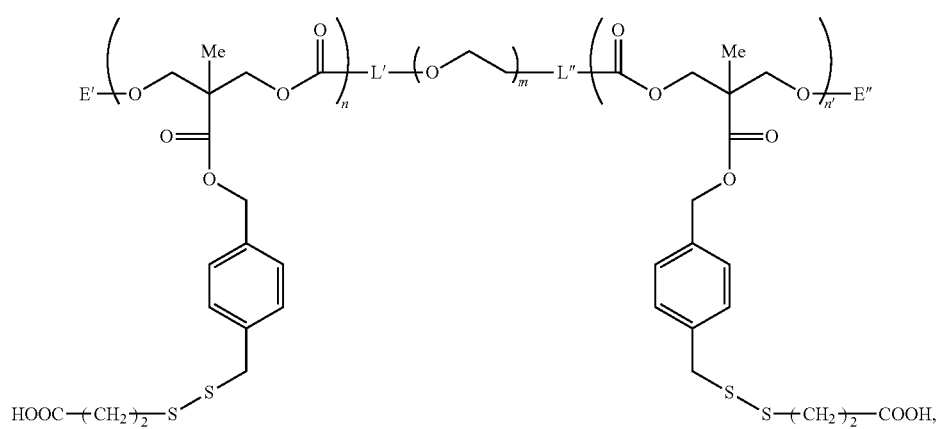

wherein
m represents average degree of polymerization, and m has a value between 1 and 300,
n represents average degree of polymerization, and n has a value between 1 and 100,
n' represents average degree of polymerization, and m' has a value between 1 and 100,
E' is a first end group,
E" is a second end group,
L' is a single bond or a divalent linking group comprising 0-20 carbons, and
L" is a single bond or a divalent linking group comprising 0-20 carbons.

In an embodiment, L' is a single bond, L" is *—O—*, E' is hydrogen, and E" is hydrogen.

Triblock Copolymers (A-B-A' type)

The block copolymer can be a linear triblock copolymer of the A-B-A' type. This BCP comprises a divalent central block B that is directly or indirectly covalently linked to a block A of formula (A-1) and a block A' of formula (A-1). The central block B is a polycarbonate chain or a polyestercarbonate chain comprising the carbonate repeat unit of formula (A-2).

More specific A-B-A'-type triblock copolymers have structures in accordance with formula (A-12):

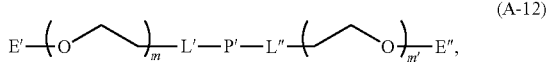

wherein
m represents average degree of polymerization (DP) of a block A, and m has a value between 1 and 300,
m' represents average degree of polymerization (DP) of a block A', and m' has a value between 1 and 300,
E' is a first end group,
E" is a second end group,
L' is a single bond or a divalent linking group comprising 0-20 carbons,
L" is a single bond or a divalent linking group comprising 0-20 carbons, and
P' is a polycarbonate chain or polyestercarbonate chain (block B) comprising a carbonate repeat unit of formula (A-2).

A first end repeat unit of central block B is covalently linked to an end repeat unit of block A by way of a divalent linking group L'. A second end repeat unit of central block B is covalently linked to an end repeat unit of block A' by way of a divalent linking group L". No restriction is placed on the structure of L' and L", with the proviso that the self-assembly properties of the BCP in water, cargo loading properties of the BCP, and cargo release properties of the BCP are not adversely affected. L' can be a single bond or a $C_0$-$C_{20}$ group. Non-limiting L' groups include divalent heteroatoms (e.g., *—O—*, *—S—*), amine groups (e.g., *—N(H)—*, *—N(R)—*, wherein R is a monovalent $C_1$-$C_6$ hydrocarbon group), carbonyl-containing groups (e.g., *—C(=O)—*, *—C(=O)O—*, *—C(=O)NH—*), and alkyleneoxy groups (e.g., *—CH$_2$CH$_2$O—*). L" can be a single bond or a $C_0$-$C_{20}$ group. Non-limiting L" groups include divalent heteroatoms (e.g., *—O—*, *—S—*), amine groups (e.g., *—N(H)—*, *—N(R)—*, wherein R is a monovalent $C_1$-$C_6$ hydrocarbon group), carbonyl-containing groups (e.g., *—C(=O)—*, *—C(=O)O—*, *—C(=O)NH—*), and alkyleneoxy groups (e.g., *—CH$_2$CH$_2$O—*).

The A-B-A'-type triblock copolymers comprise a first end group E', which is linked to a peripheral end repeat unit of block A, and a second end group E", which is linked to a peripheral end repeat unit of block A'. No restriction is placed on E' and E", with the proviso that the self-assembly properties of the BCP in water, cargo loading properties of the BCP, and cargo release properties of the BCP are not adversely affected. As non-limiting examples, E' and/or E" can be a member of the group consisting of hydrogen, $C_1$-$C_{10}$ hydrocarbyl groups (e.g., methyl, ethyl, phenyl, benzyl), aryloxy groups (e.g., phenoxy), $C_1$-$C_{10}$ alkoxy groups (e.g., methoxy, ethoxy), and $C_1$-$C_{10}$ acyl groups (e.g., acetyl, propionyl, benzoyl).

Still more specific A-B-A'-type triblock copolymers have a structure in accordance with formula (A-13):

each R" is an independent monovalent radical selected from the group consisting of hydrogen, methyl, ethyl, and propyl, and each X' is an independent member of the group consisting of *—O—* and *—NH—*.

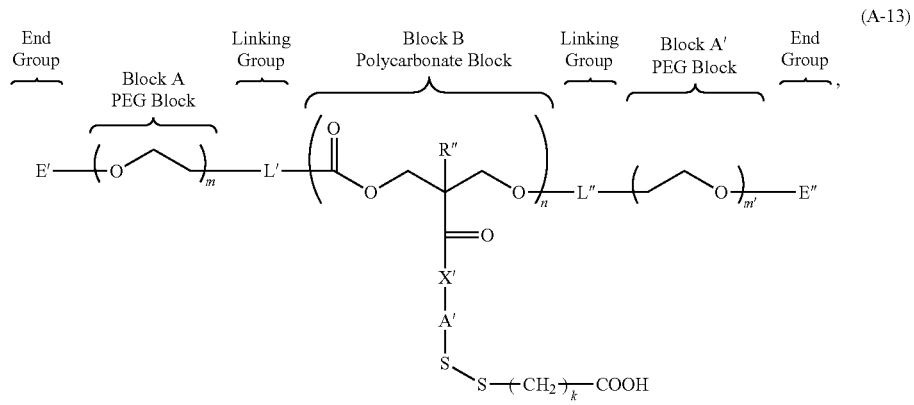

wherein
- m represents average degree of polymerization of a block A, and m has a value between 1 and 300,
- m' represents average degree of polymerization of a block A', and m' has a value between 1 and 300,
- n represents average degree of polymerization of block B, and n has a value between 1 and 100,
- each k is an independent positive integer having a value of 2-10, In an embodiment, P' is a polycarbonate chain of formula (A-3). In an embodiment, E' and E" are methyl, L' is *—O—*, and L" is *—C(=O)NH—* wherein the carbonyl of the *—C(=O)NH—* group is linked to the terminal oxygen of block B.

Yet more specific A-B-A'-type triblock copolymers have a structure in accordance with formula (A-14):

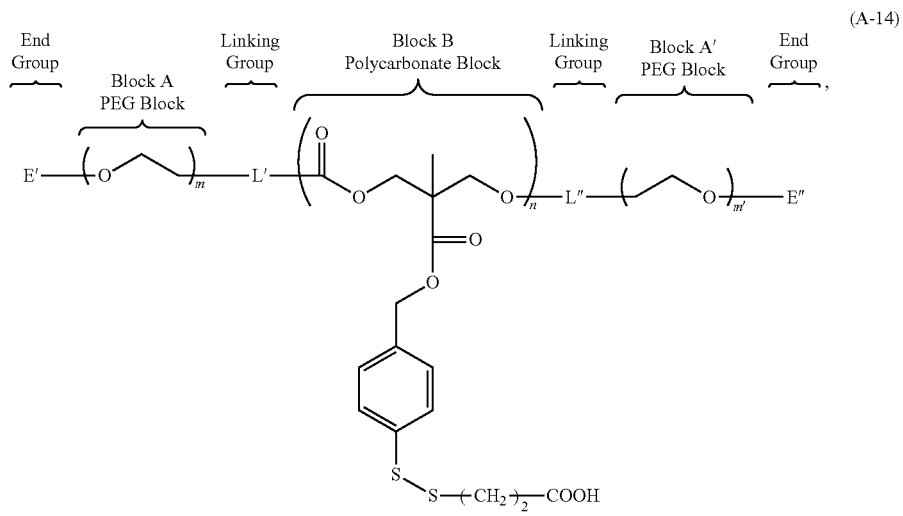

each A' is an independent divalent hydrocarbon group comprising 2-10 carbons,
E' is a first end group,
E" is a second end group,
L' is a single bond or a divalent linking group comprising 0-20 carbons,
L" is a single bond or a divalent linking group comprising 0-20 carbons, wherein
- m represents average degree of polymerization of a block A, and m has a value between 1 and 300,
- m' represents average degree of polymerization of a block A', and m' has a value between 1 and 300,
- n represents average degree of polymerization of block B, and n has a value between 1 and 100,
- E' is a first end group, E" is a second end group, L' is a single bond or a divalent linking group comprising 0-20 carbons, and L" is a single bond or a divalent linking group comprising 0-20 carbons.

In an embodiment, P' is a polycarbonate chain of formula (A-3). In an embodiment, E' and E" are methyl, L' is *—O—*, and L" is *—C(═O)NH—* wherein the carbonyl of the *—C(═O)NH—* group is linked to the terminal oxygen of block B.

Average Molecular Weight

The diblock and triblock copolymers can have a number average molecular weight (Mn) of about 1500 or more, more preferably about 1500 to about 50,000, and most preferably about 5000 to about 20,000, as determined by NMR and GPC using the Mn of the polymeric initiator. In an embodiment, the diblock and triblock copolymers have an Mn of about 5000 to about 10,000.

The diblock and triblock copolymers can have a weight average molecular weight (Mw) of about 1500 or more, more preferably about 1500 to about 50,000, and most preferably about 5,000 to about 20,000 as determined by NMR using the Mw of the polymeric initiator. In an embodiment, the diblock and triblock copolymers have a weight average molecular weight Mn of about 5000 to about 10,000.

The diblock and triblock copolymers can have a polydispersity index (PDI) of 1.01 to 2.0, more preferably 1.01 to 1.30, and even more preferably 1.01 to 1.25.

Preparation of the Block Copolymers

The diblock and triblock copolymers can be prepared by ring opening polymerization (ROP) of a cyclic carbonate monomer that comprises a leaving group capable of undergoing a post-polymerization nucleophilic substitution reaction with a thiosulfonate anion, producing a carbonate repeat unit comprising a sidechain thiosulfonate ester group.

The cyclic carbonate monomers bearing an active leaving group have a structure in accordance with formula (A-15):

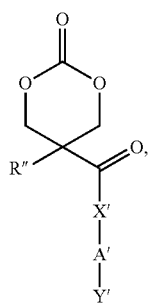

(A-15)

wherein

A' is a divalent hydrocarbon linking group comprising 2-10 carbons,

R" is a monovalent radical selected from the group consisting of hydrogen, methyl, ethyl, and propyl, X' is *—O—* or *—NH—*, and Y' is a monovalent leaving group capable of undergoing a nucleophilic substitution reaction with a thiosulfonate anion.

In an embodiment, X' is *—O—*, Y' is a halide selected from the group consisting of chloride, bromide and iodide, and A' is 1,4-phenyldimethylene:

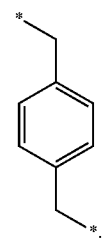

More specific cyclic carbonate monomers having a leaving group capable of undergoing a nucleophilic substitution reaction with a thiosulfonate anion include those of Scheme 3.

Scheme 3

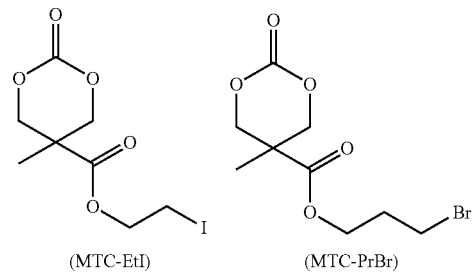

(MTC-EtI)    (MTC-PrBr)

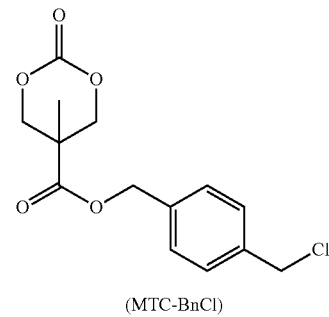

(MTC-BnCl)

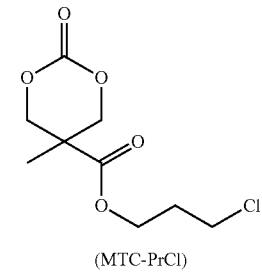

(MTC-PrCl)

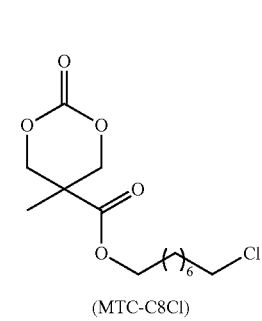

(MTC-C8Cl)

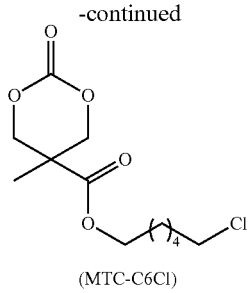

(MTC-C6Cl)

The cyclic carbonate monomers comprising the leaving group can be used singularly or in combination.

Diblock Copolymers

The reaction sequence to produce a disclosed diblock copolymer can be accomplished in three steps, starting with a ROP of cyclic carbonate monomer of formula (A-15).

The ROP reaction mixture comprises a cyclic carbonate monomer of formula (A-15), a mono-nucleophilic polymeric ROP initiator comprising a poly(ethylene oxide) chain (e.g., poly(ethylene glycol) monomethyl (MPEG), an organocatalyst, a solvent, and optionally an accelerator). The ROP produces an initial diblock copolymer comprising a block A having the structure of formula (A-1) and an initial block B, which is a polycarbonate or polyestercarbonate chain comprising a carbonate repeat unit of formula (A-16):

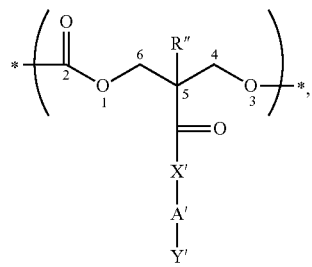

wherein
  atomic centers of the polymer backbone are numbered 1-6,
  A' is a divalent hydrocarbon linking group comprising 2-10 carbons,
  R" is a monovalent radical selected from the group consisting of hydrogen, methyl, ethyl, and propyl,
  X' is *—O—* or *—NH—*, and
  Y' is a monovalent leaving group capable of undergoing a nucleophilic substitution reaction with a thiosulfonate anion.

Exemplary non-limiting leaving groups Y' include halides (e.g., chloride, bromide, iodide), tosylate, and mesylate. Chloride and bromide are preferred Y' groups.

More specific initial diblock copolymers have structures according to formula (A-17):

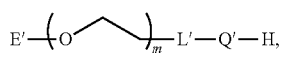

wherein
  m represents average degree of polymerization, and m has a value between 1 and 300, E' is a first end group,
L' is a single bond or a divalent linking group comprising 0-20 carbons, and
Q' is a polycarbonate or polyestercarbonate chain comprising a carbonate repeat unit of formula (A-14) and having a hydrogen end group.

Still more specific initial diblock BCPs have structures in accordance with formula (A-18):

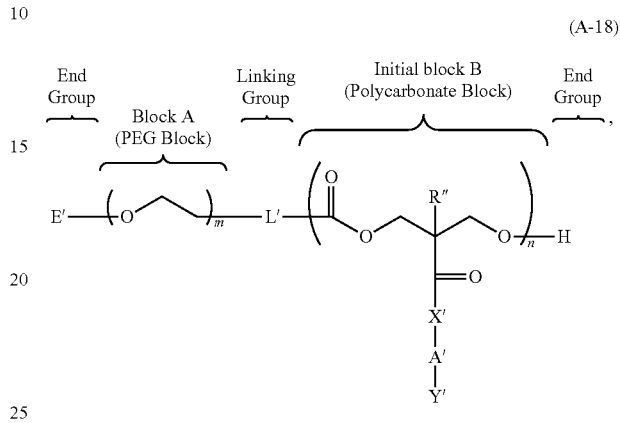

wherein
  m represents average degree of polymerization, and m has a value between 1 and 300,
  n represents average degree of polymerization, and n has a value between 1 and 100,
  each A' is an independent divalent hydrocarbon group comprising 2-10 carbons,
  E' is a first end group,
  L' is a single bond or a divalent linking group comprising 0-20 carbons,
  each R" is an independent monovalent radical selected from the group consisting of hydrogen, methyl, ethyl, and propyl,
  each X' is an independent member of the group consisting of *—O—* and *—NH—*, and
  each Y' is an independent monovalent leaving group capable of undergoing a nucleophilic substitution reaction with a thiosulfonate anion.

Optionally, the terminal alcohol group (hydroxy group) of (A-18) can be endcapped.

Treating the initial diblock copolymer comprising the carbonate repeat unit of formula (A-16) with a thiosulfonate anion (T'—S(=O)$_2$S$^-$, where T' is a C$_1$-C$_{10}$ hydrocarbyl group) produces a modified diblock copolymer comprising a carbonate repeat unit of formula (A-19):

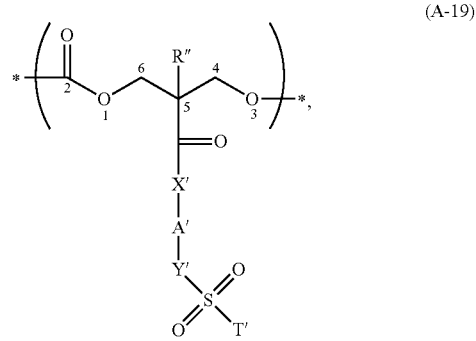

wherein
  atomic centers of the polymer backbone are numbered 1-6,
  A' is a divalent hydrocarbon linking group comprising 2-10 carbons,
  R" is a monovalent radical selected from the group consisting of hydrogen, methyl, ethyl, and propyl,
  X' is *—O—* or *—NH—*, and
  T' is a monovalent $C_1$-$C_{10}$ hydrocarbyl group.

More specific modified diblock copolymers have structures according to formula (A-20):

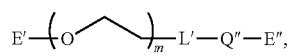

(A-20)

wherein
  m represents average degree of polymerization, and m has a value between 1 and 300,
  E' is a first end group,
  E" is a second end group selected from the group consisting of hydrogen and groups comprising one or more carbons,
  L' is a single bond or a divalent linking group comprising 0-20 carbons, and
  Q" is a polycarbonate or polyestercarbonate chain comprising a carbonate repeat unit of formula (A-19).

Still more specific modified diblock copolymers have structures in accordance with formula (A-21):

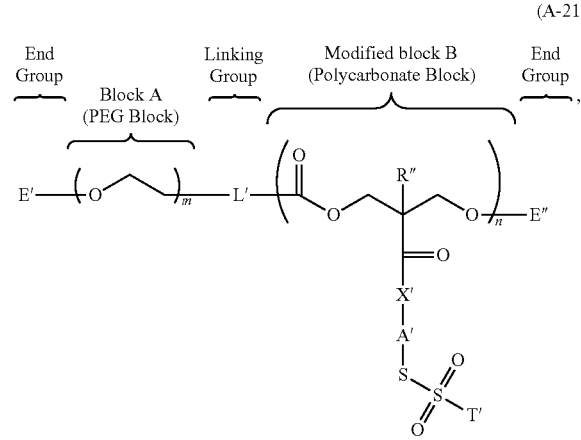

(A-21)

wherein
  m represents average degree of polymerization, and m has a value between 1 and 300,
  n represents average degree of polymerization, and n has a value between 1 and 100,
  each A' is an independent divalent hydrocarbon group comprising 2-10 carbons,
  E' is a first end group,
  E" is a second end group selected from the group consisting of hydrogen and groups comprising one or more carbons,
  L' is a single bond or a divalent linking group comprising 0-20 carbons,
  each R" is an independent monovalent radical selected from the group consisting of hydrogen, methyl, ethyl, and propyl,
  each X' is an independent member of the group consisting of *—O—* and *—NH—*, and
  each T' is an independent monovalent $C_1$-$C_{10}$ hydrocarbon group.

When E" is hydrogen in (A-200) and/or (A-21), the modified diblock copolymer of (A-20) or (A-21) can be optionally endcapped before the next step.

A preferred thiosulfonate anion is methanethiosulfonate (T' is methyl), which is commercially available as a sodium salt.

In the final step, the modified diblock copolymer is treated with a mercapto-carboxylic acid compound of formula (A-22):

(A-22)

wherein k is a positive integer having a value of 2-10.

The reaction with the mercapto-carboxylic acid compound produces the disclosed diblock copolymer comprising a carbonate repeat unit of formula (A-2).

The following reactions illustrate the preparation of block copolymer DSP-1.

In a first step, an initial diblock copolymer P-1 is formed by the room temperature ROP of MTC-BnCl, initiated by MPEG-10K, catalyzed by 1-(3,5-bis(trifluoromethyl)-phenyl)-3-cyclohexyl-2-thiourea (TU), and cocatalyzed by 1,8-diazabicyclo[5,4,0]undec-7-ene (DBU) in solvent dichloromethane (DCM).

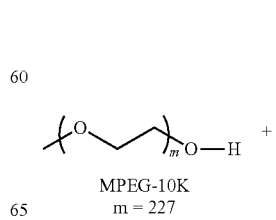

MPEG-10K
m = 227

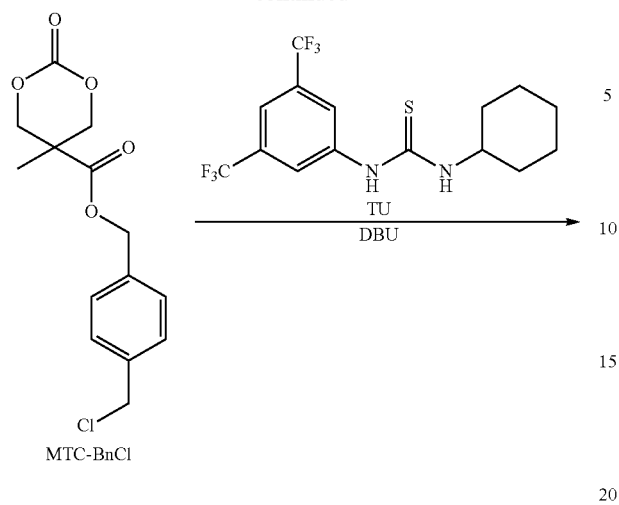

MTC-BnCl

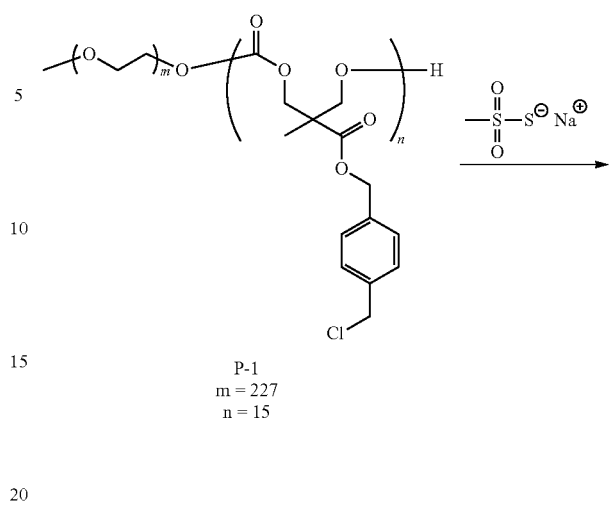

P-1
m = 227
n = 15

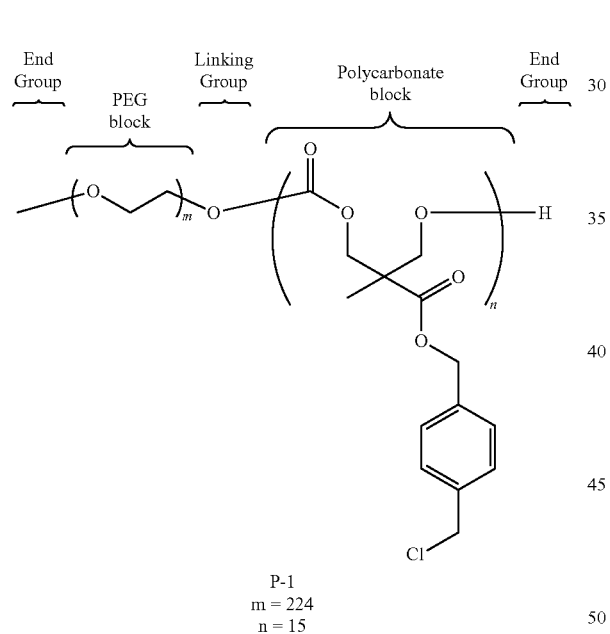

P-1
m = 224
n = 15

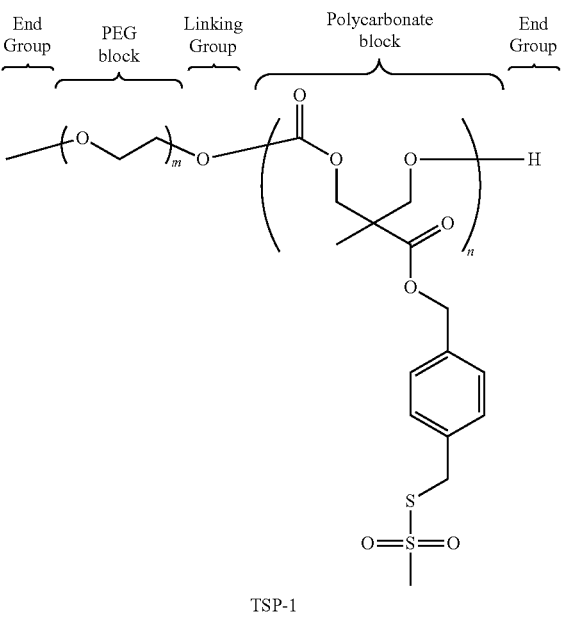

TSP-1
m = 224
n = 15

For this example, the polycarbonate block of P-1 is not endcapped. The terminal alcohol hydroxy group of the polycarbonate block is a living end group capable of initiating another ROP.

In the next step, the initial diblock copolymer P-1, which has an active chloride leaving group on the ester side chain, is treated with sodium methanethiosulfonate, thereby forming intermediate diblock copolymer TSP-1.

The polycarbonate backbone of P-1 is substantially unaffected by the thiosulfonate anion. In this example, the polycarbonate block of TSP-1 is not endcapped.

In the final step, the intermediate diblock copolymer TSP-1 is treated with 3-mercaptopropionic acid, thereby forming DSP-1.

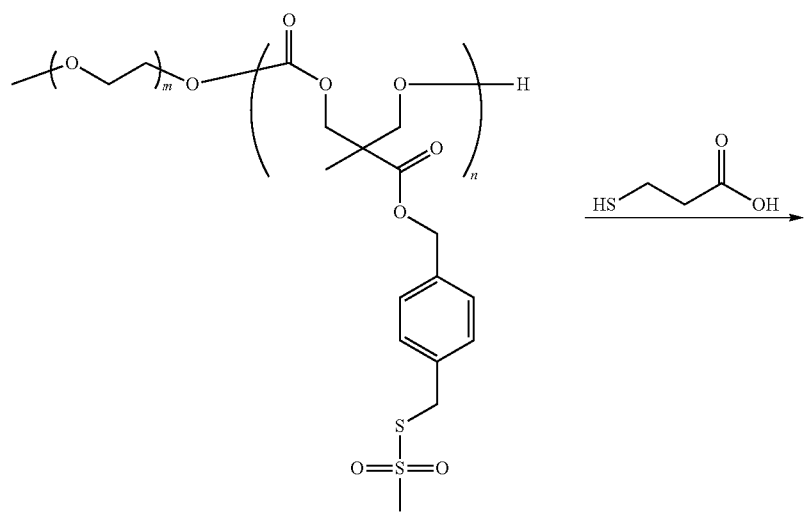

TSP-1
m = 227
n = 15

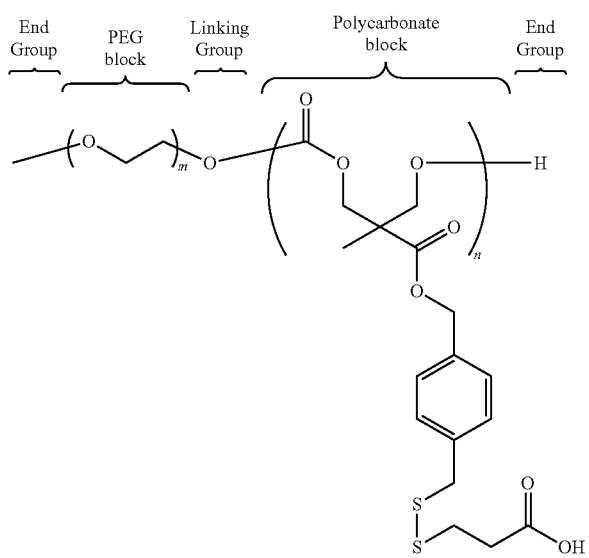

DSP-1
m = 227
n = 15

60

Preparation of B-A-B'-Type Block Copolymers

The B-A-B'-type block copolymers can be prepared in a similar manner utilizing a di-nucleophilic polymeric ROP initiator comprising a poly(ethylene oxide) chain (e.g., poly(ethylene glycol) (PEG)) in place of a mono-nucleophilic polymeric ROP initiator. This reaction is illustrated for the formation of T-1 below.

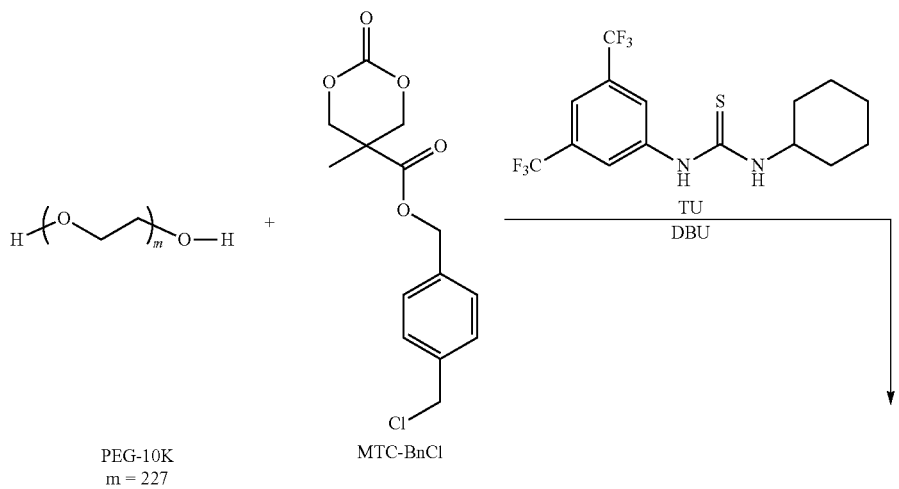

PEG-10K
m = 227

MTC-BnCl

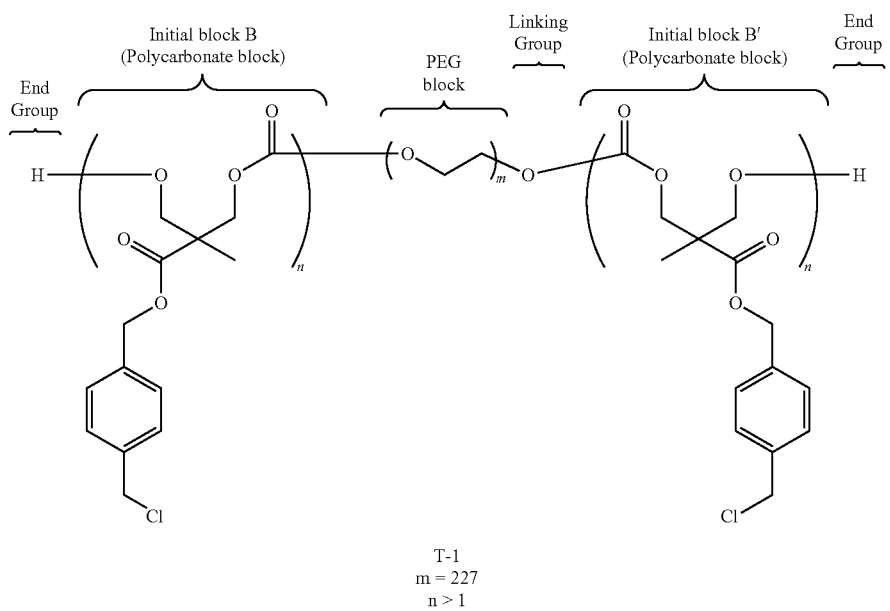

T-1
m = 227
n > 1

In this example, one end of the central PEG block (block A) is linked to the terminal carbonyl of one of the polycarbonate blocks (block B) by a single bond. The other end of PEG block is linked to the terminal carbonyl of the second polycarbonate block (block B') by a divalent oxygen *—O—*. Optionally, each of the carbonate blocks can be endcapped if desired.

The reaction of triblock copolymer T-1 with sodium methanethiosulfonate and a mercapto-carboxylic acid can be accomplished using the above-described procedure, resulting in a triblock copolymer having two polycarbonate blocks of formula (A-5).

Preparation of A-B-A'-Type Block Copolymers

The A-B-A'-type triblock copolymers can be prepared starting from an above-described initial diblock copolymer (e.g., P-1), and endcapping the initial diblock copolymer with an endcap agent comprising a poly(ethylene oxide) chain (e.g., poly(ethylene glycol) monomethyl ether isocyanate, MPEG-NCO). The reaction of MPEG-NCO with P-1 is illustrated in the formation of T-2 below.

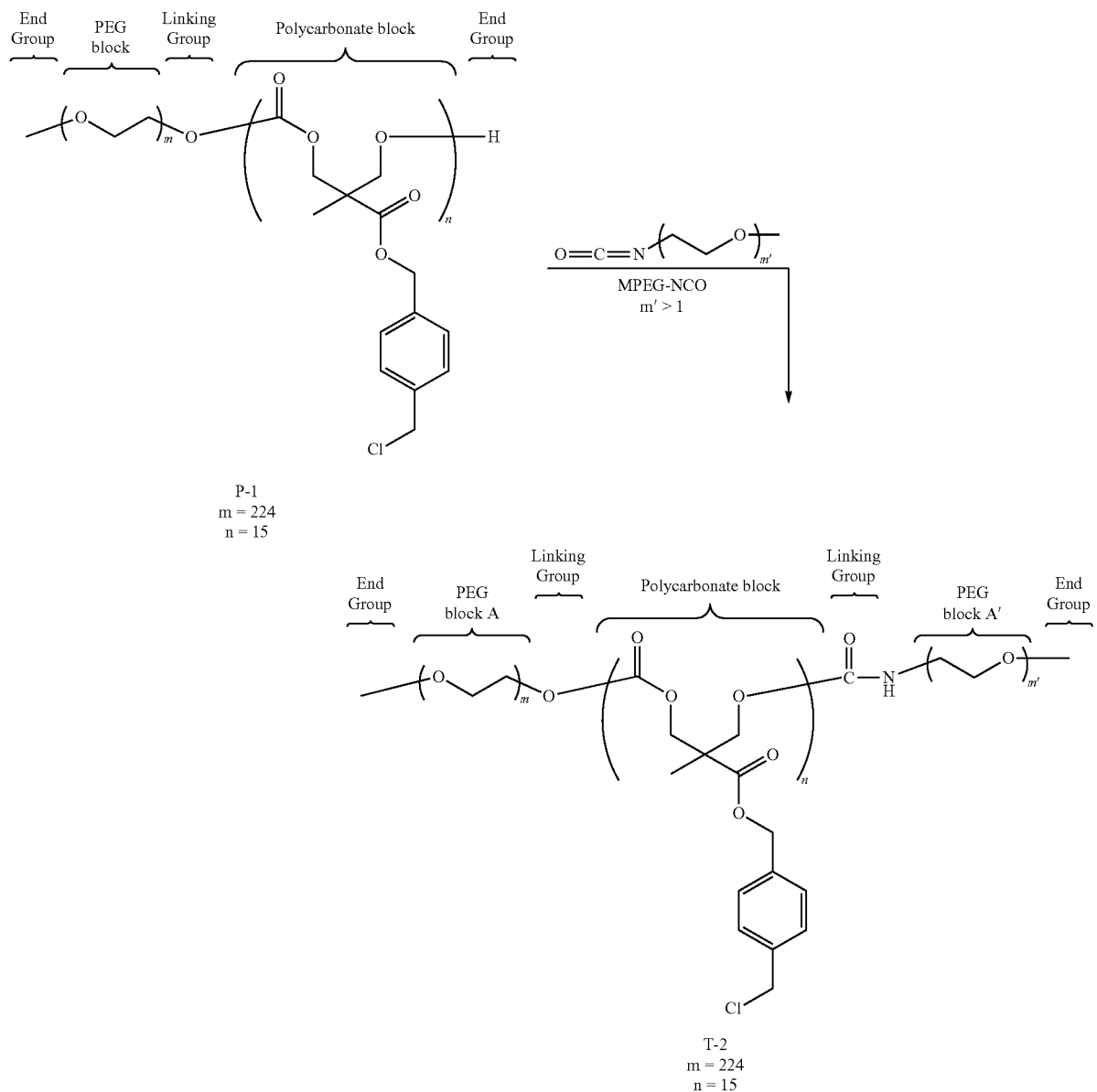

In triblock copolymer T-2, one of the two peripheral PEG blocks (block A) is linked to the terminal carbonyl of the central polycarbonate block by a divalent oxygen *—O—*. The second PEG block (block A') is linked to the terminal backbone oxygen of the central polycarbonate block by a divalent linking group*—(C=O)NH—*. In this example, each of the PEG blocks has a methyl end group.

The reaction of triblock copolymer T-2 with sodium methanethiosulfonate and a mercapto-carboxylic acid can be accomplished following the above-described procedure to produce a triblock copolymer having a central polycarbonate block of formula (A-5) (not shown).

ROP Initiators

In a preferred method of making the block copolymers, the ROP reaction mixture includes a polymeric initiator comprising a poly(ethylene oxide) chain, which is a precursor to a block A of the block copolymer. The polymeric initiator can comprise one or two nucleophilic groups selected from the group consisting of alcohols, amines, thiols, and combinations thereof.

Exemplary non-limiting PEG based initiators comprising a poly(ethylene oxide) chain include those of Scheme 4, where m>1.

Scheme 4

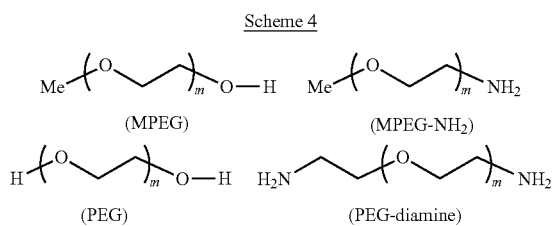

The ROP initiators can be used singularly or in combination.

ROP Catalysts

The ROP reaction mixture includes a catalyst that is preferably an organocatalyst whose chemical structure contains none of the restricted metals described further above.

The organocatalyst can be an organic acid. Exemplary organic acids include diphenylphosphate, sulfuric acid, p-toluenesulfonic acid, methanesulfonic acid, and trifluoromethane sulfonic acid (triflic acid). In an embodiment, the organocatalyst is trifluoromethane sulfonic acid.

Other organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexylthiourea (TU):

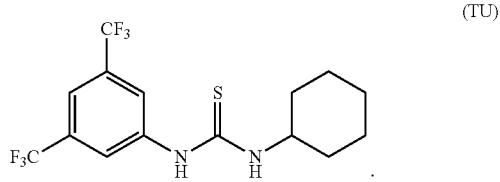 [SMILES: FC(F)(F)c1cc(NC(=S)NC2CCCCC2)cc(C(F)(F)F)c1]

(TU)

Other ROP organocatalysts comprise at least one 1,1,1,3,3,3-hexafluoropropan-2-ol-2-yl (HFP) group. Singly-donating hydrogen bond catalysts have the formula (B-1):

$R^2$—C(CF$_3$)$_2$OH (B-1), wherein $R^2$ represents a hydrogen or a monovalent radical having 1 to 20 carbons, for example, an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are listed in Scheme 5.

Scheme 5

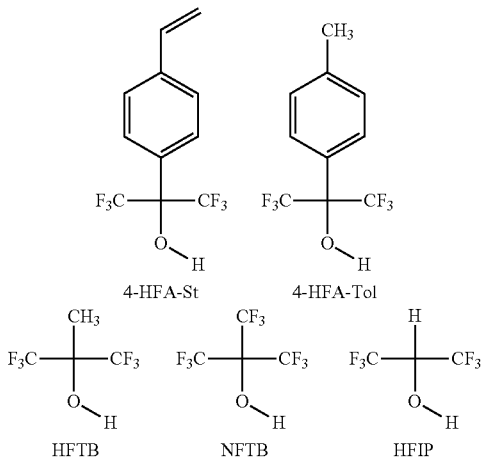

Doubly-donating hydrogen bonding catalysts have two HFP groups, represented by the formula (B-2):

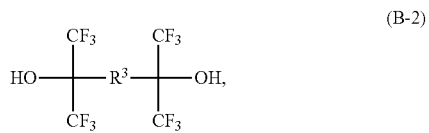

(B-2)

wherein $R^3$ is a divalent radical bridging group comprising 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, or a combination thereof. Representative double hydrogen bonding catalysts of formula (B-2) include those listed in Scheme 6. In a specific embodiment, $R^2$ is an arylene or substituted arylene group, and the HFP groups occupy positions meta to each other on the aromatic ring.

Scheme 6

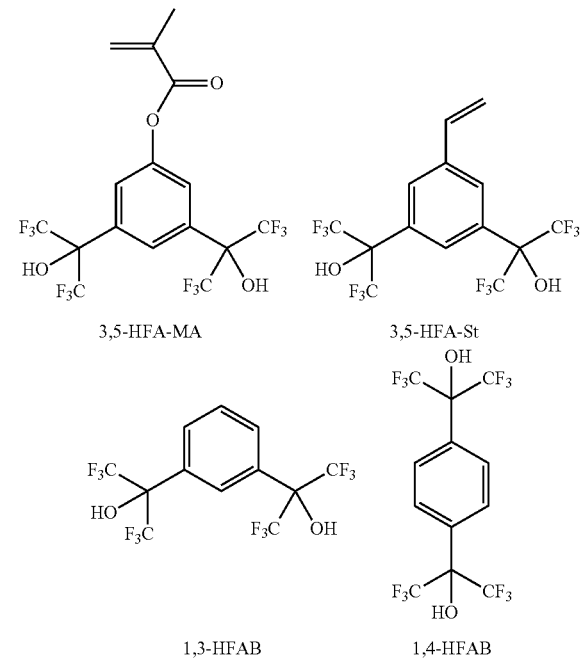

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, several organocatalysts together. The ROP catalyst can be added in a proportion of 1/20 to 1/40,000 moles relative to the cyclic carbonyl monomers, and preferably in a proportion of 1/1,000 to 1/20,000 moles relative to the cyclic carbonyl monomers.

Diluent Monomers

The ROP reaction mixture can include a second cyclic carbonyl monomer selected from the group consisting of cyclic carbonates, cyclic esters, and combinations thereof, which can undergo ring opening to form a carbonate and/or ester second repeat unit, respectively. The second repeat units can act as diluents for adjusting the hydrophilic/hydrophobic balance of the BCPs. That is, the amphiphilic properties of the BCPs can be controlled by adjusting the amount and structure of the first cyclic carbonate monomer and/or the amount and structure of a diluent second cyclic carbonyl monomer.

Non-limiting examples of diluent cyclic carbonate monomers are listed in Scheme 7.

Scheme 7

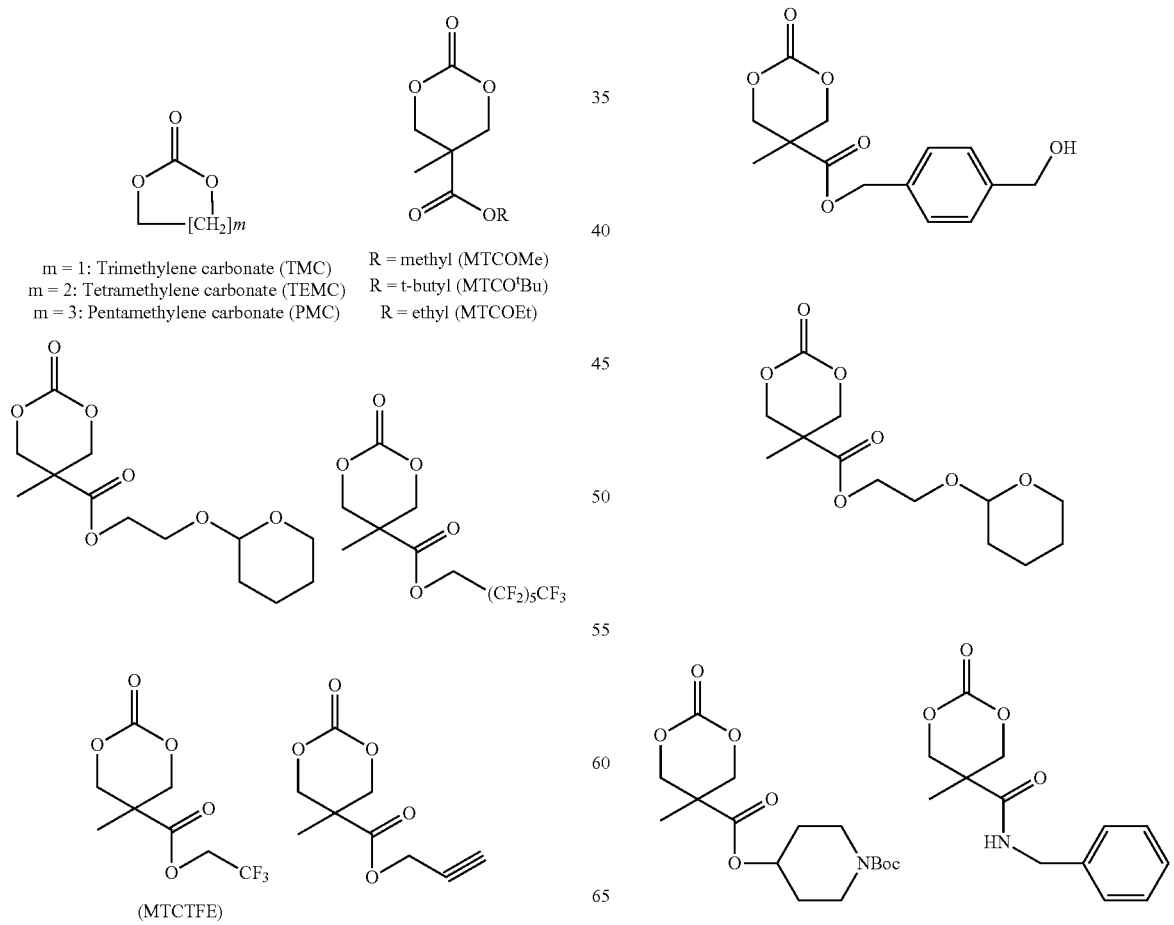

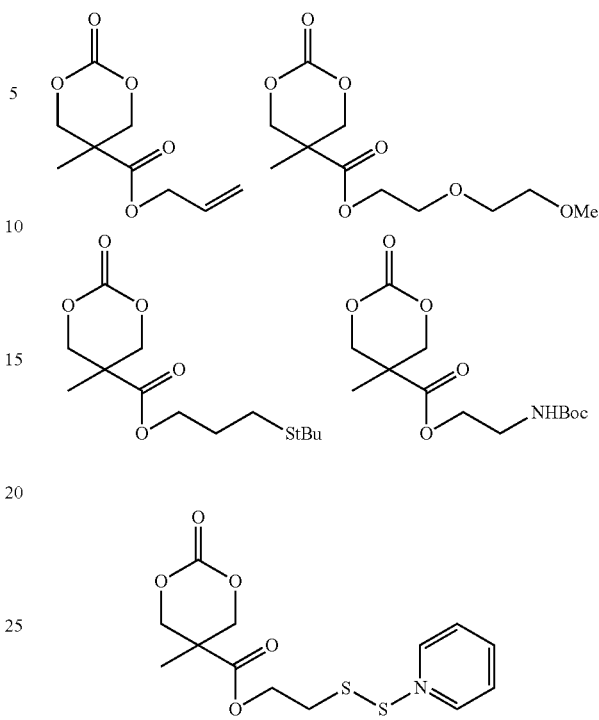

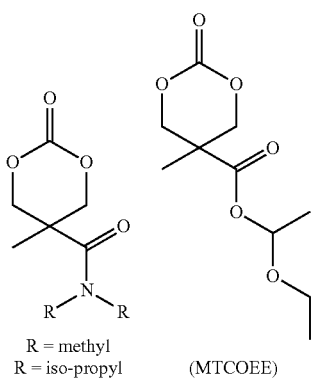

R = methyl
R = iso-propyl       (MTCOEE)

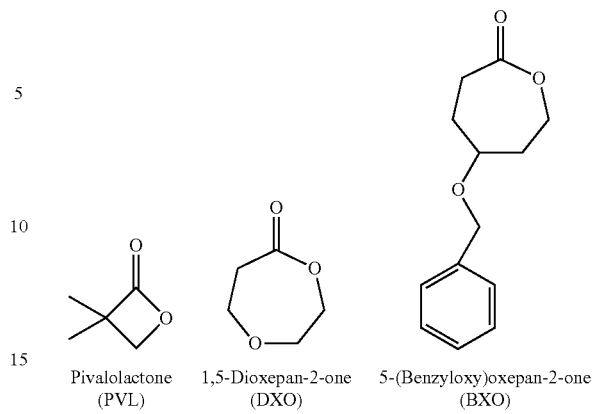

Pivalolactone (PVL)   1,5-Dioxepan-2-one (DXO)   5-(Benzyloxy)oxepan-2-one (BXO)

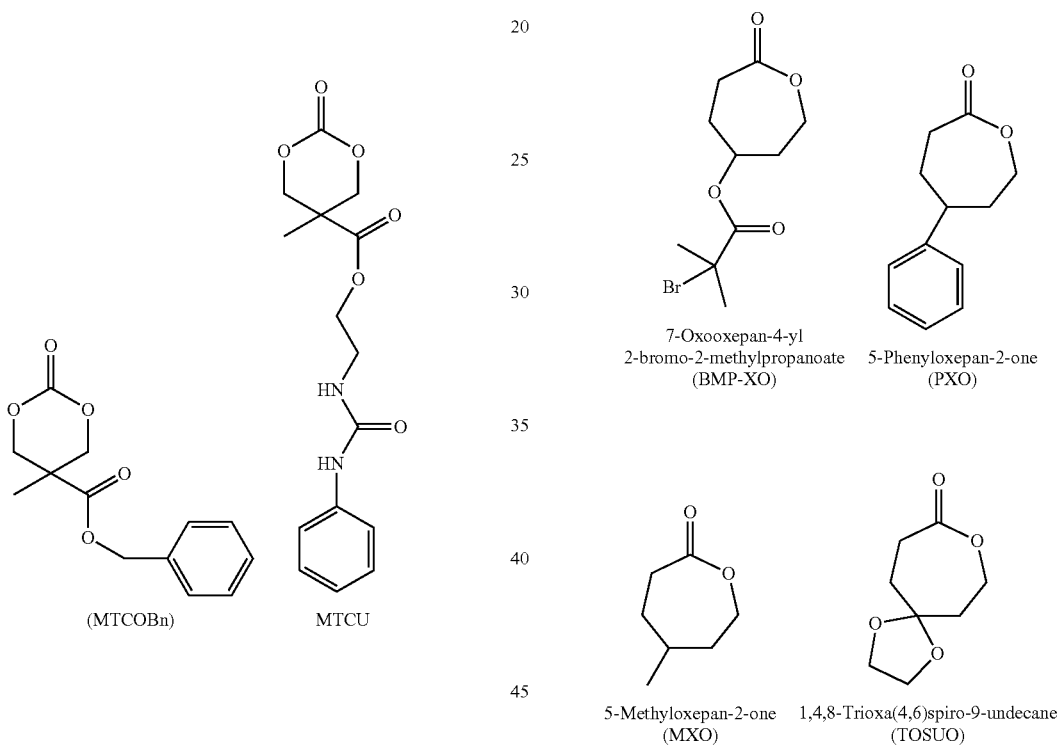

(MTCOBn)        MTCU

7-Oxooxepan-4-yl 2-bromo-2-methylpropanoate (BMP-XO)

5-Phenyloxepan-2-one (PXO)

5-Methyloxepan-2-one (MXO)

1,4,8-Trioxa(4,6)spiro-9-undecane (TOSUO)

Non-limiting exemplary cyclic ester monomers (e.g., lactones) include compounds of Scheme 8.

Scheme 8

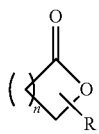

R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = CH₃; n = 1: beta-Butyrolactone (b-BL)
R = CH₃; n = 2: gamma-Valerolactone (g-VL)

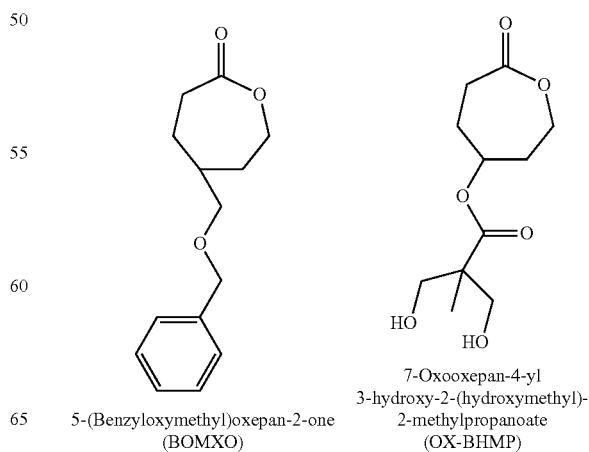

5-(Benzyloxymethyl)oxepan-2-one (BOMXO)

7-Oxooxepan-4-yl 3-hydroxy-2-(hydroxymethyl)-2-methylpropanoate (OX-BHMP)

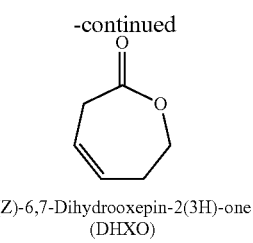

(Z)-6,7-Dihydrooxepin-2(3H)-one
(DHXO)

Other diluent cyclic ester monomers are dioxane dicarbonyl monomers of Scheme 9.

Scheme 9

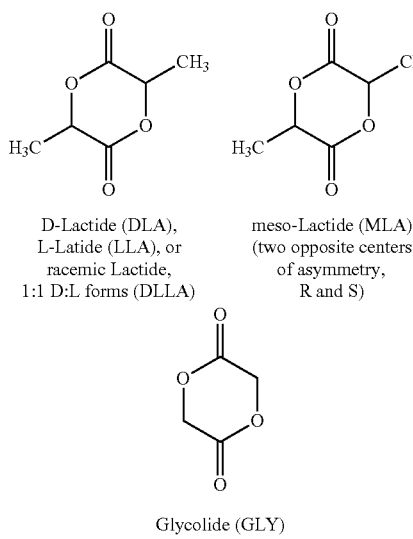

D-Lactide (DLA),
L-Latide (LLA), or
racemic Lactide,
1:1 D:L forms (DLLA)

meso-Lactide (MLA)
(two opposite centers
of asymmetry,
R and S)

Glycolide (GLY)

The above cyclic carbonyl monomers can be purified by recrystallization from a solvent such as ethyl acetate or by other known methods of purification, with particular attention being paid to removing as much water as possible from the monomer. The monomer moisture content can have a value of 1 to 10,000 ppm, 1 to 1,000 ppm, 1 to 500 ppm, and most specifically 1 to 100 ppm, by weight of the monomer.

The components used to prepare the BCPs, including the cyclic carbonyl monomer(s), ROP initiator, and/or endcapping agents, can be stereospecific or non-stereospecific. A stereospecific cyclic carbonyl monomer, repeat unit, end group, and/or linking group i) has a non-superposable mirror image and ii) comprises one or more asymmetric tetravalent carbons (i.e., tetrahedral $sp^3$ carbons). Each asymmetric tetravalent carbon is assigned an R or S symmetry based on Cahn-Ingold-Prelog (CIP) symmetry rules. For example, if a stereospecific repeat unit has one asymmetric tetravalent carbon, then the stereospecific repeat unit can be present substantially as the R stereoisomer or substantially as the S stereoisomer, meaning the stereoisomer can be present in a stereoisomeric purity of 90% to 100%, 94% or more, or more particularly 98% to 100%. In another example, if the stereospecific repeat unit has two asymmetric tetravalent carbons, the stereospecific repeat unit can be present substantially as the R,R stereoisomer, substantially as the R,S stereoisomer, substantially as the S,S stereoisomer, or substantially as the S,R stereoisomer.

ROP Accelerators

The ROP polymerization can be conducted in the presence of an optional accelerator, in particular a nitrogen base. Exemplary nitrogen base accelerators are listed below and include pyridine (Py), N,N-dimethylaminocyclohexane (Me₂NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof, shown in Scheme 10.

Scheme 10

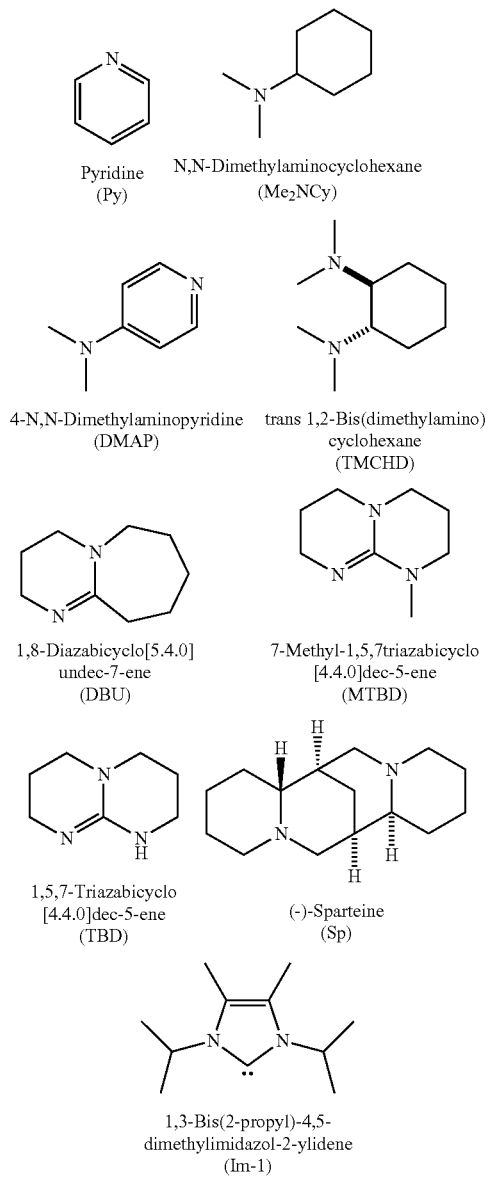

Pyridine
(Py)

N,N-Dimethylaminocyclohexane
(Me₂NCy)

4-N,N-Dimethylaminopyridine
(DMAP)

trans 1,2-Bis(dimethylamino)
cyclohexane
(TMCHD)

1,8-Diazabicyclo[5.4.0]
undec-7-ene
(DBU)

7-Methyl-1,5,7triazabicyclo
[4.4.0]dec-5-ene
(MTBD)

1,5,7-Triazabicyclo
[4.4.0]dec-5-ene
(TBD)

(−)-Sparteine
(Sp)

1,3-Bis(2-propyl)-4,5-
dimethylimidazol-2-ylidene
(Im-1)

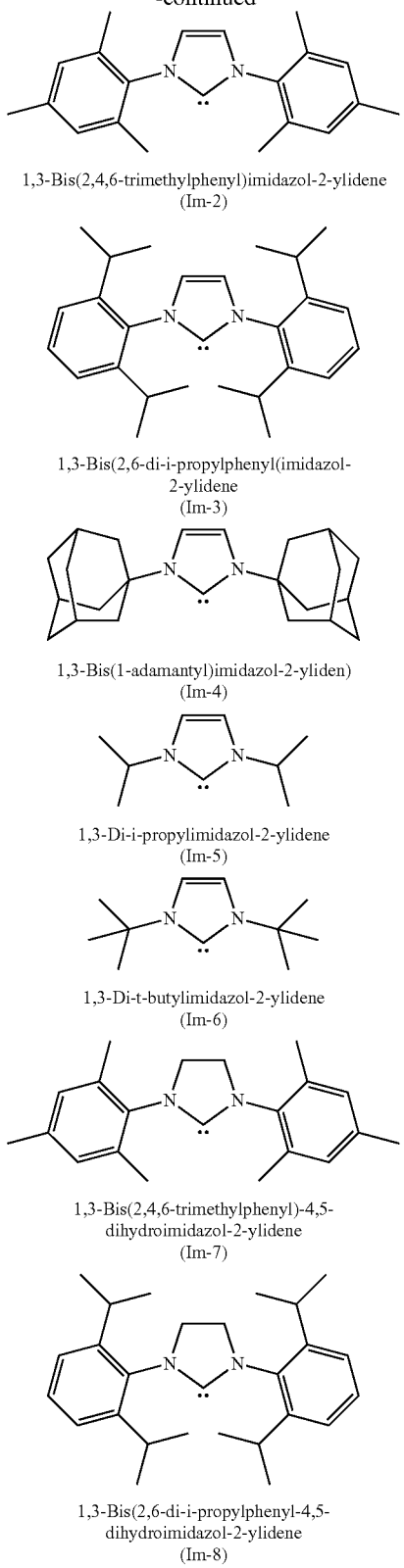

1,3-Bis(2,4,6-trimethylphenyl)imidazol-2-ylidene
(Im-2)

1,3-Bis(2,6-di-i-propylphenyl(imidazol-2-ylidene
(Im-3)

1,3-Bis(1-adamantyl)imidazol-2-yliden)
(Im-4)

1,3-Di-i-propylimidazol-2-ylidene
(Im-5)

1,3-Di-t-butylimidazol-2-ylidene
(Im-6)

1,3-Bis(2,4,6-trimethylphenyl)-4,5-dihydroimidazol-2-ylidene
(Im-7)

1,3-Bis(2,6-di-i-propylphenyl-4,5-dihydroimidazol-2-ylidene
(Im-8)

In an embodiment, the accelerator has two or three nitrogens, each capable of participating as a Lewis base, as for example in the structure (−)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

ROP Conditions

The ring-opening polymerization is preferably performed at a temperature of about 15° C. to about 50° C., and even more specifically 20° C. to 30° C. Reaction times vary with solvent, temperature, agitation rate, pressure, and equipment. In general, the polymerizations are complete within 1 to 100 hours.

The ROP reaction is preferably performed with a solvent. Exemplary solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. A suitable monomer concentration is about 0.1 to 5 moles per liter, and more particularly about 0.2 to 4 moles per liter.

The ROP polymerizations are conducted using a dry, inert atmosphere, such as nitrogen or argon, and at a pressure of 100 MPa to 500 MPa (1 atm to 5 atm), more typically at a pressure of 100 MPa to 200 MPa (1 atm to 2 atm). At the completion of the reaction, the solvent can be removed using reduced pressure.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The amount of initiator is calculated based on the equivalent molecular weight per nucleophilic initiator group. The nucleophilic initiator groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomer. For example, if the molecular weight of the initiator is 100 g/mole and the initiator has 2 alcohol hydroxyl groups, the equivalent molecular weight per hydroxyl group is 50 g/mole. If the polymerization calls for 5 mol % hydroxyl groups per mole of cyclic carbonyl monomer, the amount of initiator is 0.05×50=2.5 g per mole of cyclic carbonyl monomer.

The catalysts can be removed by selective precipitation or in the case of the solid supported catalysts, simply by filtration. The block copolymer can comprise residual catalyst in an amount greater than or equal to 0 wt % (weight percent), based on total weight of the hydrophilic polymer and the residual catalyst.

Endcap Agents

The intermediate and disulfide-carboxylic acid containing block copolymer can further be treated with an endcap agent to prevent further chain growth and stabilize the reactive end groups against unwanted side reactions such as chain scission. Endcap agents include, for example, materials for converting terminal hydroxyl groups to esters, such as carboxylic acid anhydrides, carboxylic acid chlorides, or reactive esters (e.g., p-nitrophenyl esters). In an embodiment, the endcap agent is acetic anhydride, which converts reactive hydroxy end groups to acetate ester groups. In another embodiment, the endcap agent contains a poly (ethylene oxide) chain. The endcap agent can also comprise a biologically active moiety, which becomes bound to the terminal end group of the ring opened polymer chain.

The endcap agent can comprise a poly(ethylene oxide) chain for preparing A-B-A triblock copolymers as described above.

In an embodiment, the diblock and triblock copolymer has a living end group (i.e., not endcapped), which is capable of initiating a ring opening polymerization.

Cytotoxicity

The BCPs alone are generally non-cytotoxic. For example, cell viability of human breast cancer cells (BT-474 cell line) and hereditary leiomyomastosis and renal cancer cells (NCCFH-01 cell line) can be in a range of 80% to 100% at polymer concentrations of at least 1000 mg/L.

Loaded Particles

The self-assembly properties of the block copolymers allows the block copolymers to serve as dispersing aids for therapeutic agents (e.g., drugs, genes, proteins, peptides) in an aqueous mixture.

The disclosed BCPs can self-assemble by non-covalent interactions in water, thereby forming discrete nano-sized particles dispersed in the solvent. The particles comprise two or more self-assembled macromolecules of a disclosed BCP bound by non-covalent interactions. The particles can comprise water molecules bound by non-covalent interactions (e.g., water of hydration). The particles can have a hydrophilic surface region and a relatively hydrophobic interior core region.

Herein, a loaded particle is a particle comprising two or more self-assembled macromolecules of a disclosed BCP and a therapeutic agent, which are bound by non-covalent interactions. A method of forming a loaded particle comprises i) forming a first mixture comprising water, a disclosed BCP, and optionally an organic solvent, ii) forming a second mixture comprising a therapeutic agent and a solvent selected from the group consisting of organic solvents, water, and combinations thereof, iii) combining the first mixture and the second mixture, thereby forming a third mixture, and iv) removing the organic solvent(s) from the third mixture, thereby forming a loaded particle comprising the BCP and the therapeutic agent bound by non-covalent interactions. The third mixture can be dialyzed against deionized water using a dialysis membrane system to remove the organic solvent.

Exemplary organic solvents include methanol, ethanol, propanol, 2-propanol, 1-butanol, 2-butanol, t-butyl alcohol, acetone, 2-butanone, dimethoxyethane, diglyme, diethyl ether, methyl t-butyl ether, methylene chloride, ethyl acetate, ethylene glycol, glycerin, dimethylsulfoxide, dimethylformamide, acetic acid, tetrahydrofuran (THF), and dioxane.

The loaded particles can comprise the BCP in an amount of about 40.0 wt % to about 99.9 wt %, and the therapeutic agent in an amount of about 60.0 wt % to about 0.1 wt %, each based on total dry weight of the loaded particles.

The loaded particles can have an average particle size (circular cross sectional diameter) of 10 nm to 500 nm, more preferably 10 nm to 250 nm, and most preferably 25 nm to 100 nm as measured by dynamic light scattering. For the foregoing particle sizes, the aqueous solution can have a pH of 5.0 to 8.0, more particularly 6.0 to 8.0, or even more particularly 7.0 to 8.0.

Also disclosed is a composition for a medical treatment comprising water and the loaded particles in contact with the water. The loaded particles comprise the BCP and a therapeutic agent bound by non-covalent interactions. The loaded particles are preferably discrete particles dispersed in the water. The compositions can be administered topically, orally, and/or by injection. Depending on the intended use, the loaded particles can release the therapeutic agent in the blood stream and/or within a target cell.

The loaded particles of the composition can have an average particle size as measured by dynamic light scattering of about 10 nm to about 500 nm, more preferably 10 nm to about 200 nm, and most preferably 10 nm to 100 nm.

The compositions can comprise the loaded particles in an amount greater than 0 weight percent (wt %), and more particularly in an amount of about 0.1 wt. % to about 15 wt % based on total dry weight of the compositions.

The therapeutic agent can be any suitable therapeutic agent capable of forming a reversible complex (i.e., by non-covalent interactions) with a disclosed BCP, wherein the complex is capable of controlled release of the therapeutic agent. Non-limiting therapeutic agents include DNA, genes, peptides, proteins, enzymes, lipids, phospholipids, and nucleotides), natural or synthetic organic compounds (e.g., drugs, dyes, synthetic polymers, oligomers, and amino acids), inorganic materials (e.g., metals and metal oxides), radioactive variants of the foregoing, and combinations of the foregoing.

The therapeutic agent is effective in inducing a desirable medical response. Non-limiting desirable medical responses include selective alteration of the chemical structure and/or activity of a cell type relative to another cell type. As an example, one desirable change in a chemical structure can be the incorporation of a gene into the DNA of a cell. A desirable change in activity can be the expression of the transfected gene by the cell. Another desirable change in cell activity can be the induced production of a desired hormone or enzyme. Alternatively, a desirable change in activity can be the selective death of one cell type over another cell type. For example, the therapeutic agent can be a drug that selectively kills a bacterium, inactivates a virus, and/or kills tumor cells. No limitation is placed on the relative change in cellular activity caused by the therapeutic agent, providing the change is desirable and useful. Moreover, no limitation is placed on the therapeutic agent, providing the therapeutic agent induces a medically useful response. In an embodiment, the therapeutic agent is a drug. In another embodiment, the therapeutic agent is a cancer drug. In another embodiment, the therapeutic agent is an antimicrobial agent.

Exemplary commercially available drugs include the following, where the generic drug name is enclosed in parentheses next to the all-capitalized registered trade name: 13-cis-Retinoic Acid, 2-CdA (Cladribine), 2-Chlorodeoxyadenosine (Cladribine), 5-Azacitidine, 5-Fluorouracil (Fluorouracil), 5-FU (Fluorouracil), 6-Mercaptopurine, 6-MP (6-Mercaptopurine), 6-TG (Thioguanine), 6-Thioguanine (Thioguanine), ABRAXANE® (Paclitaxel protein bound), ACCUTANE® (Isotretinoin), Actinomycin-D (Dactinomycin), ADRIAMYCIN® (Doxorubicin), ADRUCIL® (Fluorouracil), AFINITOR® (Everolimus), AGRYLIN® (Anagrelide), ALA-CORT® (Hydrocortisone), Aldesleukin, Alemtuzumab, ALIMTA® (Pemetrexed), Alitretinoin (9-cis-retinoic acid), Alkaban-AQ (Vinblastine), ALKERAN® (Melphalan), All-transretinoic Acid (Tretinoin), Alpha Interferon (Interferon Alfa), Altretamine, Amethopterin (Methotrexate), Amifostine, Aminoglutethimide, Anagrelide, ANANDRON® (Nilutamide), Anastrozole, Arabinosylcytosine (Cytarabine), Ara-C (Cytarabine), ARANESP® (Darbepoetin Alfa), AREDIA® (Pamidronate), ARIMIDEX® (Anastrozole), AROMASIN® (Exemestane), ARRANON® (Nelarabine), Arsenic Trioxide, Asparaginase, ATRA (All-transretinoic Acid), AVASTIN®

(Bevacizumab), Azacitidine, BCG, BCNU (Carmustine), Bendamustine (Bendamustine Hydrochloride), Bevacizumab, Bexarotene, BEXXAR® (Tositumomab), Bicalutamide, BICNU® (Carmustine), BLENOXANE® (Bleomycin), Bleomycin, Bortezomib, Busulfan, BUSULFEX® (Busulfan), C225 (Cetuximab), Calcium Leucovorin (Leucovorin), CAMPATH® (Alemtuzumab), CAMPTOSAR® (Irinotecan), Camptothecin-11 (Irinotecan), Capecitabine, CARAC® (Fluorouracil), Carboplatin, Carmustine, Carmustine Wafer, CASODEX® (Bicalutamide), CC-5013 (Lenalidomide), CCI-779 (Temsirolimus), CCNU (Lomustine), CDDP (Cisplatin), CEENU® (Lomustine), CERUBIDINE® (Daunomycin), Cetuximab, Chlorambucil, Cisplatin, Citrovorum Factor (Leucovorin), Cladribine, Cortisone (Hydrocortisone), CO SMOGEN® (Dactinomycin), CPT-11 (Irinotecan), Cyclophosphamide, CYTADREN® (Aminoglutethimide), Cytarabine, Cytarabine Liposomal, CYTOSAR-U® (Cytarabine), CYTOXAN® (Cyclophosphamide), Dacarbazine, DACOGEN® (Decitabine), Dactinomycin, Darbepoetin Alfa, Dasatinib, Daunomycin, Daunorubicin, Daunorubicin Hydrochloride, Daunorubicin Liposomal, DAUNOXOME® (Daunorubicin Liposomal), DECADRON™ (Dexamethasone), Decitabine, DELTA-CORTEF® (Prednisolone), DELTASONE® (Prednisone), Denileukin Diftitox, DEPOCYT® (Cytarabine Liposomal), Dexamethasone, Dexamethasone Acetate, Dexamethasone Sodium Phosphate, DEXASONE® (Dexamethasone), Dexrazoxane, DHAD (Mitoxantrone), DIC (Dacarbazine), DIODEX® (Dexamethasone), Docetaxel, DOXIL® (Doxorubicin Liposomal), Doxorubicin, Doxorubicin Liposomal, DROXIA® (Hydroxyurea), DTIC (Dacarbazine), DTIC-DOME® (Decarbazine), Duralone (Methylprednisolone), EFUDEX® (Fluorouracil), ELIGARD® (Leuprolide), ELLENCE® (Epirubicin), ELOXATIN® (Oxaliplatin), ELSPAR® (Asparaginase), EMCYT® (Estramustine), Epirubicin, Epoetin Alfa, ERBITUX® (Cetuximab), Erlotinib, Erwinia L-asparaginase (Asparaginase), Estramustine, ETHYOL® (Amifostine), ETOPOPHOS® (Etoposide), Etoposide, Etoposide Phosphate, EULEXIN® (Flutamide), Everolimus, EVISTA® (Raloxifene), Exemestane, FARESTON® (Toremifene), FASLODEX® (Fulvestrant), FEMARA® (Letrozole), Filgrastim, Floxuridine, FLUDARA® (Fludarabine), Fludarabine, FLUOROPLE® (Fluorouracil), Fluorouracil, Fluorouracil (cream), Fluoxymesterone, Flutamide, Folinic Acid (Leucovorin), FUDR® (Floxuridine), Fulvestrant, G-CSF (Pegfilgrastim), Gefitinib, Gemcitabine, Gemtuzumab ozogamicin, GEMZAR® (Gemcitabine), GLEEVEC® (Imatinib mesylate), GLIADEL® Wafer (Carmustine Wafer), GM-CSF (Sargramostim), Goserelin, Granulocyte—Colony Stimulating Factor (Pegfilgrastim), Granulocyte Macrophage Colony Stimulating Factor (Sargramostim), HALOTESTIN® (Fluoxymesterone), HERCEPTIN® (Trastuzumab), HEXADROL® (Dexamethasone), HEXALEN® (Altretamine), Hexamethylmelamine (Altretamine), HMM (Altretamine), HYCAMTIN® (Topotecan), HYDREA® (Hydroxyurea), Hydrocort Acetate (Hydrocortisone), Hydrocortisone, Hydrocortisone Sodium Phosphate, Hydrocortisone Sodium Succinate, HYDROCORTONE® Phosphate (Hydrocortisone), Hydroxyurea, Ibritumomab, Ibritumomab Tiuxetan (Ibritumomab), IDAMYCIN® (Idarubicin), Idarubicin, IFEX® (Ifosfamide), IFN-alpha (Interferon alfa), Ifosfamide, IL-11 (Oprelvekin), IL-2 (Aldesleukin), Imatinib mesylate, Imidazole Carboxamide (Decarbazine), Interferon alfa, Interferon Alfa-2b (PEG Conjugate), Interleukin-2 (Aldesleukin), Interleukin-11 (Oprelvekin), INTRON® A (interferon alfa-2b), IRESSA® (Gefitinib), Irinotecan, Isotretinoin, Ixabepilone, IXEMPRA® (Ixabepilone), Kidrolase (Asparaginase), LANACORT® (Hydrocortisone), Lapatinib, L-asparaginase, LCR (Vincristine), Lenalidomide, Letrozole, Leucovorin, LEUKERAN® (Chlorambucil), LEUKINE® (Sargramostim), Leuprolide, Leurocristine (Vincristine), LEUSTATIN® (Cladribine), Liposomal Ara-C, LIQUID PRED® (Prednisone), Lomustine, L-PAM (Melphalen), L-Sarcolysin (Melphalen), LUPRON® (Leuprolide), LUPRON DEPOT® (Leuprolide), MATULANE® (Procarbazine), MAXIDEX® (Dexamethasone), Mechlorethamine, Mechlorethamine Hydrochloride, Medralone (Methylprednisolone), MEDROL® (Methylprednisolone), MEGACE® (Megestrol), Megestrol, Megestrol Acetate (Megastrol), Melphalan, Mercaptopurine (6-Mercaptopurine), Mesna, MESNEX® (Mesna), Methotrexate, Methotrexate Sodium (Methotrexate), Methylprednisolone, METICORTEN® (Prednisone), Mitomycin (Mitomycin C), Mitomycin-C, Mitoxantrone, M-Prednisol (Methylprednisolone), MTC (Mitomycin-C), MTX (Methotrexate), MUSTARGEN® (Mechlorethamine), Mustine (Mechlorethamine), MUTAMYCIN® (Mitomycin-C), MYLERAN® (Busulfan), MYLOCEL® (Hydroxyurea), MYLOTARG® (Gemtuzumab ozogamicin), NAVELBINE® (Vinorelbine), Nelarabine, NEOSAR® (Cyclophosphamide), NEULASTA® (Pegfilgrastim), NEUMEGA® (Oprelvekin), NEUPOGEN® (Filgrastim), NEXAVAR® (Sorafenib), NILANDRON® (Nilutamide), Nilutamide, NIPENT® (Pentostatin), Nitrogen Mustard (Mechlorethamine), NOLVADEX® (Tamoxifen), NOVANTRONE® (Mitoxantrone), Octreotide, Octreotide acetate (Octreotide), ONCASPAR® (Pegaspargase), ONCOVIN® (Vincristine), ONTAK® (Denileukin Diftitox), ONXOL® (Paclitaxel), Oprelvekin (Interleukin-11), ORAPRED® (Prednisolone), ORASONE® (Prednisone), Oxaliplatin, Paclitaxel, Paclitaxel Protein-bound, Pamidronate, Panitumumab, PANRETIN® (Alitretinoin), PARAPLATIN® (Carboplatin), PEDIAPRED® (Prednisolone), PEG Interferon, Pegaspargase, Pegfilgrastim, PEG-INTRON® (Interferon Alfa-2b), PEG-L-asparaginase, Pemetrexed, Pentostatin, Phenylalanine Mustard (Melphalen), PLATINOL® (Cisplatin), Platinol-AQ (Cisplatin), Prednisolone, Prednisone, PRELONE® (Prednisolone), Procarbazine, PROCRIT® (Epoetin Alfa), PROLEUKIN® (Aldesleukin), Prolifeprospan 20 with Carmustine Implant (Carmustine Wafer), PURINETHOL® (6-Mercaptopurine), Raloxifene, REVLIMID® (Lenalidomide), RHEUMATREX® (Methotrexate), RITUXAN® (Rituximab), Rituximab, Roferon-A (Interferon Alfa-2a), RUBEX® (Doxorubicin), Rubidomycin hydrochloride (Daunomycin), SANDOSTATIN® (Octreotide), SANDOSTATIN LAR® (Octreotide), Sargramostim, SOLU-CORTEF® (Hydrocortisone), SOLU-MEDROL® (Methylprednisolone), Sorafenib, SPRYCEL® (Dasatinib), STI-571 (Imatinib Mesylate), Streptozocin, SU11248 (Sunitinib), Sunitinib, SUTENT® (Sunitinib), Tamoxifen, TARCEVA® (Erlotinib), TARGRETIN® (Bexarotene), TAXOL® (Paclitaxel), TAXOTERE® (Docetaxel), TEMODAR® (Temozolomide), Temozolomide, Temsirolimus, Teniposide, TESPA (Thiotepa), Thalidomide, THALOMID® (Thalidomide), THERACYS® (BCG), Thioguanine, Thioguanine Tabloid (Thioguanine), Thiophosphoamide (Thiotepa), THIOPLEX® (Thiotepa), Thiotepa, TICE® (BCG), TOPOSAR® (Etoposide), Topotecan, Toremifene, TORISEL® (Temsirolimus), Tositumomab, Trastuzumab, TREANDA® (Bendamustine Hydrochloride), Tretinoin, TREXALL® (Methotrexate), TRISENOX® (Arsenic Trioxide), TSPA (Thiotepa), TYKERB® (Lapatinib), VCR (Vincristine), VECTIBIX® (Panitumumab), VELBAN® (Vinblastine), VELCADE® (Bortezomib), VEPESID® (Etoposide), VESANOID® (Tretinoin), VIADUR® (Leuprolide), VIDAZA® (Azacitidine), Vinblastine, Vinblastine Sulfate, VINCASAR PFS® (Vincristine), Vincristine, Vinorelbine, Vinorelbine tartrate (Vinorelbine), VLB (Vinblastine), VM-26 (Teniposide), Vorinostat, VP-16 (Etoposide), VUMON® (Teniposide), XELODA® (Capecitabine), ZANOSAR® (Streptozocin), ZEVALIN® (Ibritumomab), ZINECARD® (Dexrazoxane), ZOLADEX® (Goserelin), Zoledronic acid, ZOLINZA® (Vorinostat), and ZOMETA® (Zoledronic acid).

Non-limiting examples of rigid hydrophobic drugs (with stereochemistry shown) include the anti-tumor drug paclitaxel (PTX):

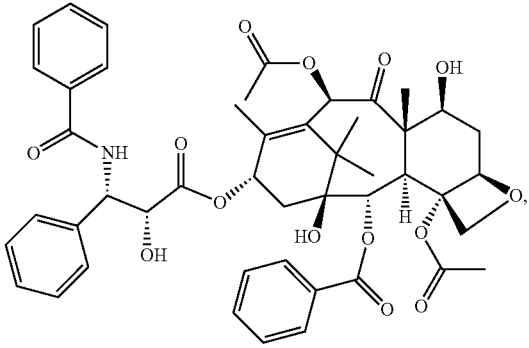 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

anti-tumor drug doxorubicin (DOX):

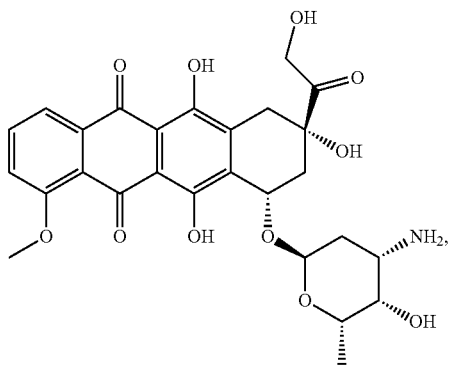 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

immunosuppressive drug cyclosporin A (CYC):

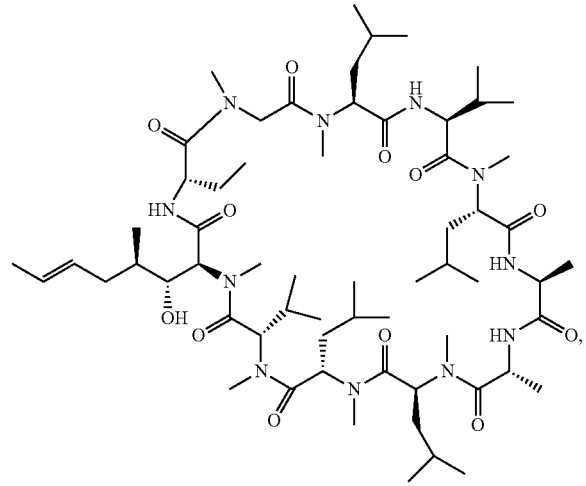 [SMILES: C/C=C/C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

and hair growth drug spironolactone (SPL):

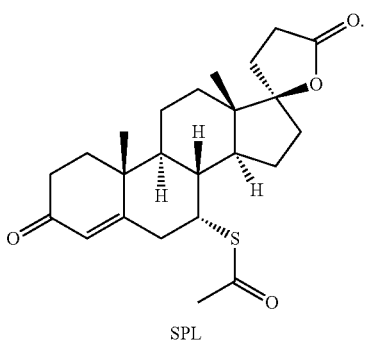

SPL

The loaded particles can comprise the therapeutic agents singularly or in combination. The aqueous compositions can comprise one or more different loaded particles comprising different therapeutic agents.

INDUSTRIAL APPLICABILITY

Compositions comprising the loaded particles can be used for human and/or non-human medical treatments. The compositions can be administered in the form of a powder, a pill, a liquid solution, paste, and/or a gel. The compositions can be used as a drug. The compositions can be administered topically, orally, as suppositories, and/or by injection, including intravenous injections. The compositions can comprise an oil in addition to water and have the form of a stable aqueous dispersion.

Also disclosed is a method of killing a cell, comprising contacting a cell with a loaded particle, thereby killing the cell. In an embodiment, the cell is a cancer cell. In an embodiment, the cell is a bacterium. The bacterium can be a Gram-positive bacterium, Gram-negative bacterium, yeast, and/or fungus.

Non-limiting exemplary bacteria (microbes) include Gram-positive Staphylococcus aureus (S. aureus), Gram-negative Escherichia coli (E. coli), fungus Candida albicans (C. albicans), Gram-negative Pseudomonas aeruginosa (P. aeruginosa), and yeasts. Other bacteria include Gram-positive Staphylococcus epidermidis (S. epidermidis), Gram-positive Methicillin-resistant Staphylococcus aureus (MRSA), Gram-positive Vancomycin-resistant Enterococcus (VRE), Gram-negative Acinetobacter baumannii (A. baumannii), and Gram-negative Klebsiella pneumoniae (K. pneumoniae) and Cryptococcus neoformans (C. neoformans).

An antimicrobial composition comprises a loaded particle comprising a disclosed BCP and an antimicrobial agent. The antimicrobial composition can be applied to a human and/or non-human animal tissue, including mammalian and/or non-mammalian animal tissue. The general term "animal tissue" includes wound tissue, burn tissue, skin, internal organ tissue, blood, bones, cartilage, teeth, hair, eyes, nasal surfaces, oral surfaces, other body cavity surfaces, and any cell membrane surfaces. In an embodiment, a method comprises contacting an animal tissue with the loaded polymer, thereby killing a bacterium.

The antimicrobial composition can be used in the form of a powder, a pill, and/or an aqueous mixture applied as a freely flowing liquid, spray, cream, injectable mixture, and/or gel. Uses include disinfectants for hands, skin, hair, bone, ear, eye, nose, throat, internal tissue, wounds, and teeth (e.g., as a mouthwash). Still other uses include disinfectants for articles such as medical devices. Medical devices include swabs, catheters, sutures, stents, bedpans, gloves, facial masks, absorbent pads, absorbent garments, internal absorbent devices, and insertable mechanical devices.

The antimicrobial compositions can be used for disinfecting surfaces of homes, businesses, and particularly hospitals that contact animal tissue and/or animal fluids. Exemplary home and commercial building surfaces include floors, door surfaces, bed surfaces, air conditioning surfaces, bathroom surfaces, railing surfaces, kitchen surfaces, and wall surfaces. Other articles include medical devices, cloths, garments, and non-medical equipment. Surfaces of articles can comprise materials such as wood, paper, metal, cloth, plastic, rubber, glass, paint, leather, or combinations thereof. In an embodiment, a method comprises contacting a surface of an article with the loaded polymer composition, thereby disinfecting the surface. In another embodiment, a method comprises contacting a surface of an article with an aqueous mixture of the composition.

The following examples demonstrate the preparation of diblock BCPs, their cytotoxicity, and their effectiveness in forming a drug loaded particles with doxorubicin (DOX) for treatment of tumor cells. The loaded particles can release the DOX in response to a change in pH and/or by reaction with GSH. Without being bound by theory, following endocytosis, the DOX-loaded particles are believed to be destabilized in the more acidic environment of the endosome by protonation of the BCP carboxylic acid groups, which triggers initial drug release. The results indicate that after endosomal escape, cleavage of the disulfide bonds by GSH in the cytoplasm of the tumor cell causes release of more DOX.

EXAMPLES

Materials used in the following examples are listed in Table 1.

TABLE 1

| ABBREVIATION | DESCRIPTION | SUPPLIER |
|---|---|---|
| BT-474 cells | Human breast cancer cells | ATCC |
| DBU | 1,8-Diazabicyclo[5,4,0]undec-7-ene | Sigma-Aldrich |
| DCM | Dichloromethane | Sigma-Aldrich |
| DOX | Doxorubicin, purchased as hydrochloride salt (DOX-HCl) | Merck, SG |
| FBS | Fetal bovine serum | Invitrogen/GIBCO, SG |
| GSH | Glutathione | Sigma-Aldrich |
| MPEG-5K | Poly(ethylene glycol) monomethyl ether, Mn = 5000, DP = 113 | Sigma-Aldrich |
| MPEG-10K | Poly(ethylene glycol) monomethyl ether, Mn = 10000, DP = 227 | Sigma-Aldrich |
| MTT | 1-(4,5-Dimethylthiazol-2-yl)-3,5-Diphenylformazan | Sigma-Aldrich |
| NaMTS | Sodium methane sulfonate | Sigma-Aldrich |
| NCCFH-01 cells | Hereditary leiomyomastosis and renal cancer cell line | Institute of Bioengineering and Nanotechnology, SG |
| PBS | Phosphate buffered saline | Sigma-Aldrich |
| TMA | Trimethylamine | Sigma-Aldrich |
| TU | N-Bis(3,5-Trifluoromethyl)Phenyl-N'-Cyclohexylthiourea | Prepared below |

Herein, Mn is the number average molecular weight, Mw is the weight average molecular weight, and MW is the molecular weight of one molecule.

All chemical reagents were purchased from Sigma-Aldrich (U.S.A.) and used as received unless otherwise specified.

1-(3,5-bis(Trifluoromethyl)-phenyl)-3-cyclohexyl-2-thiourea (TU) was prepared according to PRATT, et al., "Exploration, Optimization, and Application of Supramolecular Thiourea Amine Catalysts for the Synthesis of Lactide (Co)polymers", Macromolecules, (2006), volume 39, pages 7863-7871. TU was dissolved in THF, stirred with $CaH_2$, filtered, and freed of solvent in vacuo.

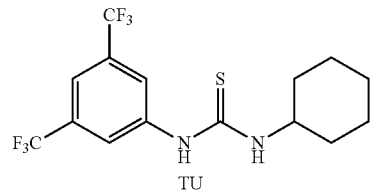

TU

Prior to use, 1,8-diazabicyclo [5,4,0]undec-7-ene (DBU) was stirred over $CaH_2$ and vacuum distilled before being transferred to a glove box.

Doxorubicin-hydrochloride (DOX-HCl) was purchased from Merck (Singapore). Doxorubicin (DOX) has the following structure.

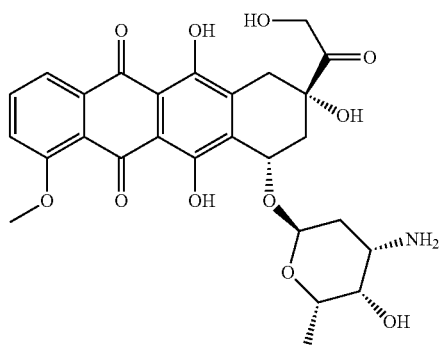

Doxorubicin

BT-474 human breast cancer cell line was purchased from ATCC (Manassas, Va., U.S.A). Hereditary leiomyomastosis and renal cancer cells (NCCFH-01 cell line) was obtained from Dr. Min-Han Tan, Institute of Bioengineering and Nanotechnology, Singapore. Cells were cultured in RPMI-1640 medium containing 25 mM Hepes and L-Glutamine (Lonza, Singapore) supplemented with 10% fetal bovine serum (FBS), 100 U/mL penicillin and 100 µg/mL streptomycin at 37° C. in 5% $CO_2$. 3-[4,5-Dimenthylthiazol-2-yl]-2,5-diphenyl tetrazolium bromide (MTT) was dissolved in phosphate-buffered saline (PBS, pH 7.4) with a concentration of 5 mg/mL, and the solution was filtered with a 0.22 micrometer filter to remove blue formazan crystals prior to usage.

Cyclic carbonate monomer MTC-BnCl was synthesized according to CHIN, et al., "Biodegradable Broad-Spectrum Antimicrobial Polycarbonates: Investigating the Role of Chemical Structure on Activity and Selectivity", Macromolecules, (2013), volume 46, pages 8797-8807.

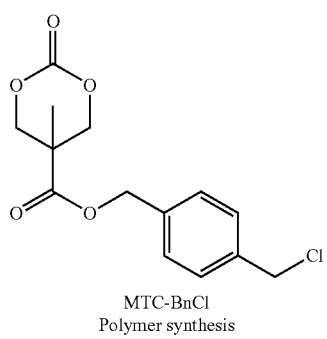

MTC-BnCl
Polymer synthesis

Example 1

Formation of diblock polymer P-1 containing an active chlorobenzyl group. The poly(ethylene oxide) block, referred to as PEG block, polycarbonate block comprising a pendent benzyl chloride moiety, oxide linking group, and end groups are shown in the structure of P-1.

The detailed procedure for the ring-opening polymerization of MTC-BnCl monomer with MPEG-10K (Mn 10000 g mol$^{-1}$) as macroinitiator is given as a representative example. Using a glove box, MTC-BnCl (299 mg, 1.0 mmol) was added to a reaction vial containing TU (18.5 mg, 0.05 mmol) dissolved in anhydrous DCM (2 mL). The mixture was subsequently charged with MPEG-10K (500 mg, 0.05 mmol) before adding DBU (7.46 microliters, 0.05 mmol) and the resulting mixture was stirred at room temperature for 1 hour. Upon completion of the reaction as ascertained from GPC chromatography, an excess of benzoic acid (10 mg, 0.08 mmol) was added to quench the catalyst. The crude polymer was then precipitated twice into cold diethyl ether, centrifuged and the supernatant decanted to obtain a white powdery solid P-1 (89% yield). 1H NMR (400 MHz, CDCl$_3$, 22° C.): δ7.39-7.27 (m, Ph-H, overlapped with CDCl$_3$ peak), 5.18-5.08 (m, 30H, —OCOCH$_2$—), 4.55 (m, 29H, —CH$_2$Cl), 4.35-4.19 (m, 58H, —OCOOCH$_2$— and —OCH$_2$CCH$_3$—), 3.71-3.59 (bs, 909H, PEG —CH$_2$—), 1.29-1.18 (m, 45H, —CH$_3$). The polycarbonate block has an average degree of polymerization (DP)=15 (i.e., n=15 in the above structure).

Example 2

Preparation of P-2 from MPEG-5K (Mn 1000, m=113).

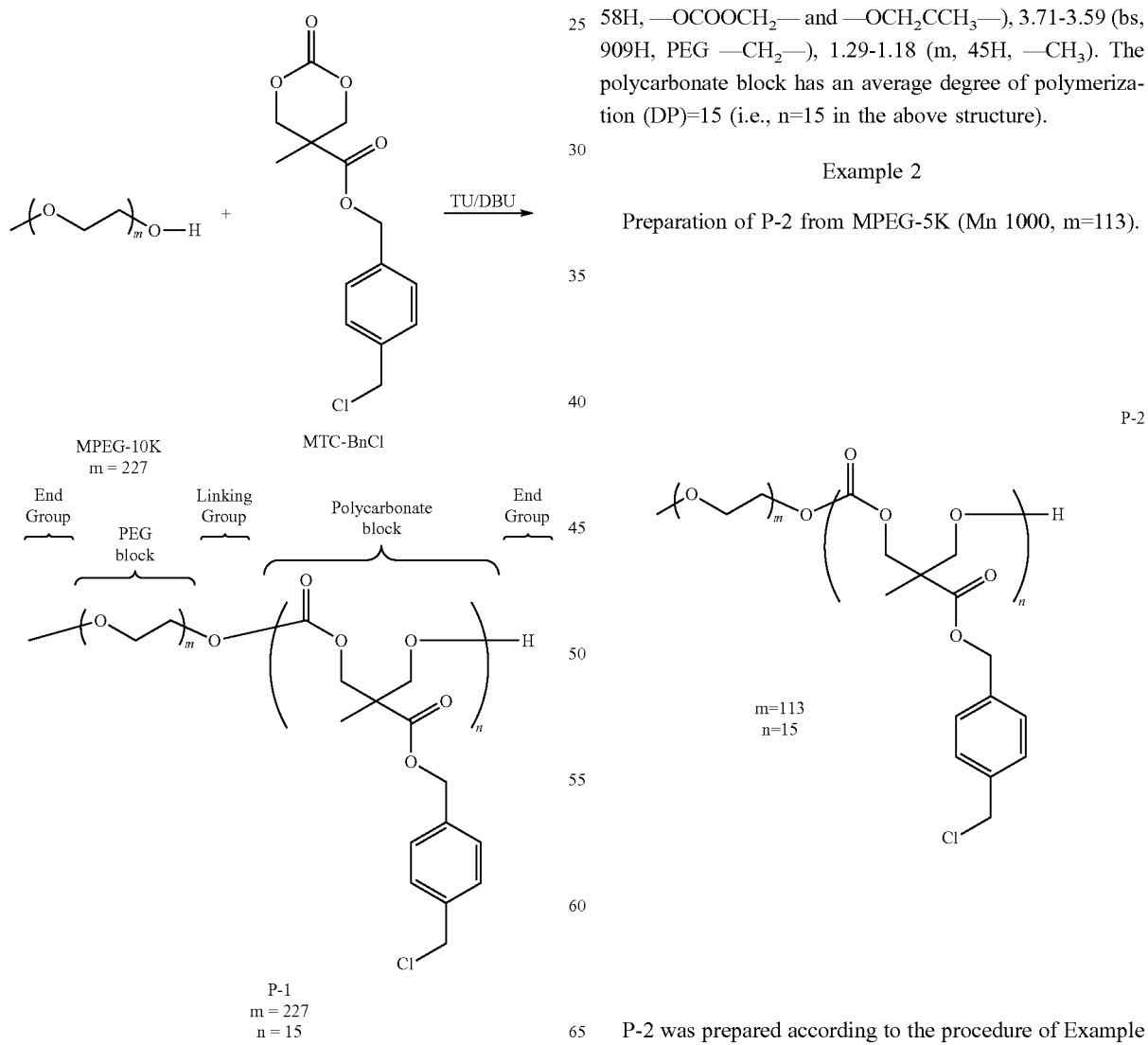

P-2 was prepared according to the procedure of Example 1 using MPEG-5K in place of MPEG-10K. For P-2, m=113 and n=15.

Example 3

Preparation of P-3 from MPEG-5K (Mn 1000, m=113).

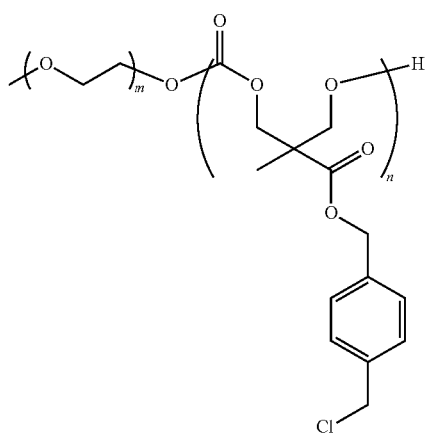

m = 113
n = 7

P-3 was prepared according to the general procedure of Example 1 using MPEG-5K and half the amount of MTC-BnCl. For P-3, m=113 and n=7.

Example 4

Formation of thiosulfonate-containing polymer TSP-1 from P-1. The PEG block, polycarbonate block comprising a thiosulfonate moiety, oxide linking group and end groups are shown in the structure of TSP-1 below.

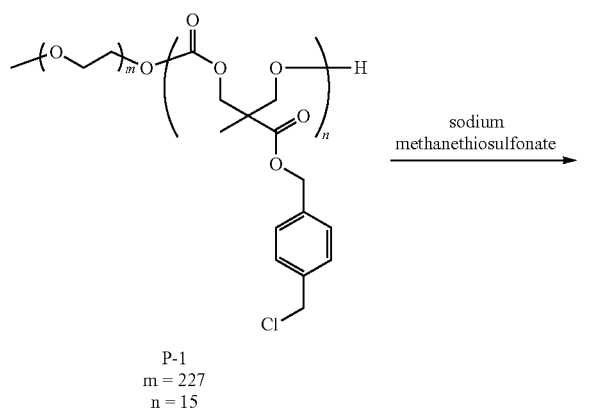

P-1
m = 227
n = 15

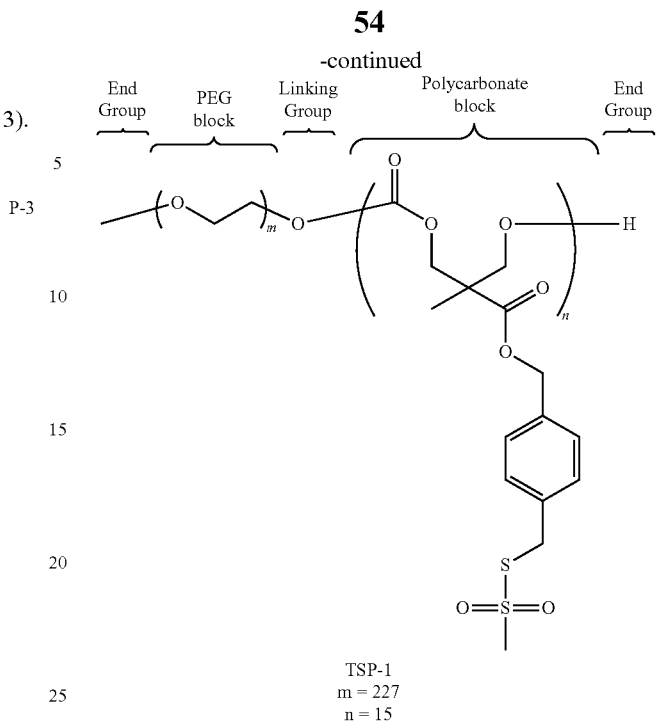

TSP-1
m = 227
n = 15

The following procedure is representative. In a reaction vial, block polymer P-1 (0.60 g, 0.04 mmol) was dissolved in a 5:1 acetonitrile:methanol mixture (6 mL). Sodium methanethiosulfonate (NaMTS) was subsequently added in excess (2 equivalents relative to benzyl chloride groups). The reaction mixture was stirred overnight at 50° C. After removal of the solvent in vacuo, the crude mixture was re-dissolved in DCM and filtered to remove NaCl and unreacted NaMTS. The crude polymer TSP-1 was precipitated in cold diethyl ether and dried as a waxy white solid (90% yield). 1H NMR (400 MHz, DMSO, 22° C.): δ 7.46-7.27 (m, 59H, Ph-H), 5.11 (m, 30H, OCOCH$_2$—), 4.51-4.43 (m, 29H, —CH$_2$S—), 4.33-4.12 (m, 61H, —OCOOCH$_2$— and —OCH$_2$CCH$_3$—), 3.51 (bs, 909H, PEG —CH$_2$—), 3.35-3.31 (m, 46H, —SO$_2$CH$_3$), 1.21-1.07 (m, 45H, —CH$_3$).

Example 5

Formation of thiosulfonate-containing polymer TSP-2 from P-2.

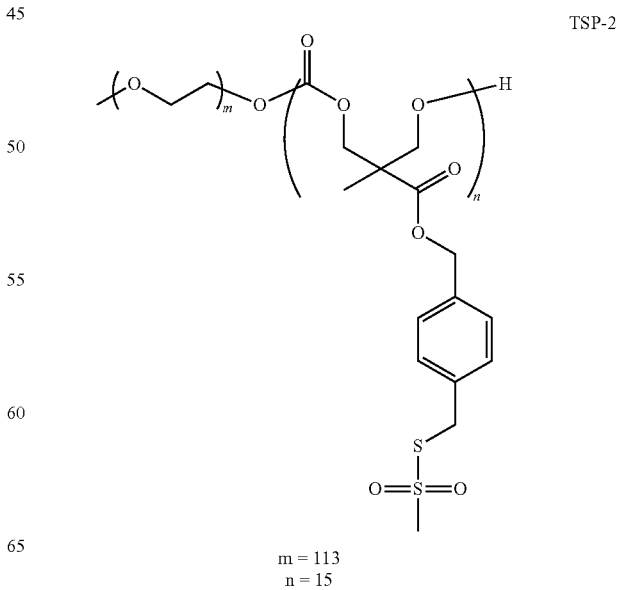

TSP-2
m = 113
n = 15

TSP-2 was prepared according to the procedure of Example 4 using P-2 in place of P-1. For TSP-2, m=113 and n=15.

Example 6

Formation of thiosulfonate-containing polymer TSP-3 from P-3.

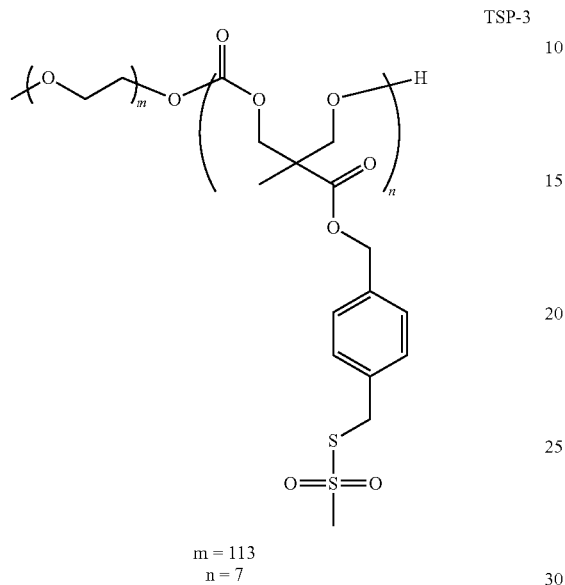

TSP-3
m = 113
n = 7

TSP-3 was prepared according to the procedure of Example 4 using P-3 in place of P-1. For TSP-3, m=113 and n=7.

Example 7

Formation of disulfide-containing polymer DSP-1 from TSP-1. The PEG block, polycarbonate block comprising a disulfide acid moiety, oxide linking group and end groups are shown in the structure of DSP-1 below.

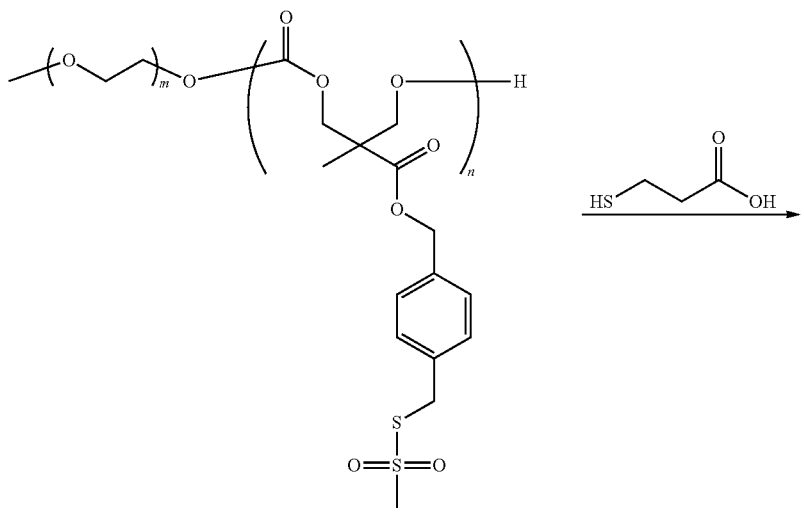

TSP-1
m = 227
n = 15

-continued

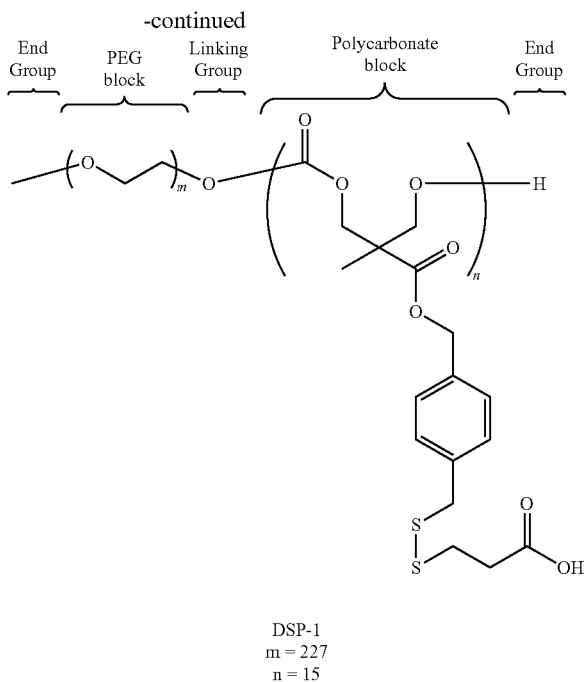

DSP-1
m = 227
n = 15

The following procedure is representative. In a reaction vial TSP-1 (0.50 g, 0.03 mmol) was dissolved in anhydrous THF (5 mL). 3-mercaptopropionic acid (0.72 g, 15 equivalents relative to benzyl chloride groups) was then added, and the reaction mixture was stirred overnight at 40° C. Upon completion of the reaction, the reaction mixture was precipitated twice in cold diethyl ether, centrifuged and the supernatant decanted to afford the crude copolymer DSP-1 as a waxy white solid. Further purification was carried out via dialysis against DMSO for 48 hours. After twice precipitating the polymer in diethyl ether, the solvent was removed. The resultant polymer DSP-1 was re-dissolved in deionized (DI) water and freeze-dried to yield a white flaky solid (79% yield). 1H NMR (400 MHz, DMSO, 22° C.) δ 7.36-7.17 (m, 60H, Ph-H), 5.07 (m, 2H, OCOCH$_2$—), 4.32-4.09 (m, 59H, —OCOOCH$_2$— and —OCH$_2$CCH$_3$—), 3.97-3.86 (m, 28H, —CH$_2$S—), 3.50 (bs, 909H, PEG —CH$_2$—), 2.75-2.64 (m, 28H, —SCH$_2$CH$_2$COOH), 2.56-2.49 (m, overlapped with d$_6$-DMSO peak, —SCH$_2$CH$_2$COOH), 1.20-1.04 (m, 45H, —CH$_3$). PDI=1.24; Mw=15602 gmol$^{-1}$.

Example 8

Formation of thiosulfonate-containing polymer DSP-2 from TSP-2.

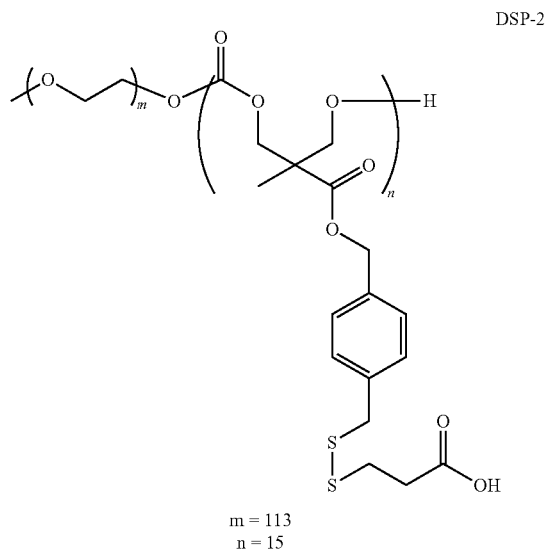

DSP-2
m = 113
n = 15

DSP-2 was prepared according to the procedure of Example 7 using TSP-2 in place of TSP-1. For DSP-2, m=113 and n=15. PDI=1.21; Mw=11002 gmol$^{-1}$.

Example 9

Formation of thiosulfonate-containing polymer DSP-3 from TSP-3.

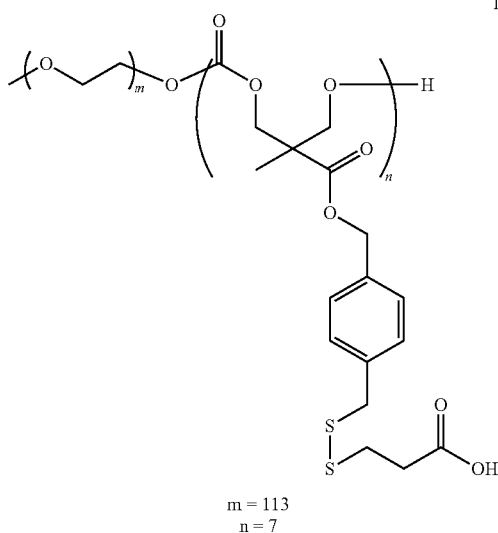

DSP-3 m = 113
n = 7

DSP-3 was prepared according to the procedure of Example 7 using TSP-3 in place of TSP-1. For DSP-3, m=113 and n=7. PDI=1.26; Mw=7801 gmol$^{-1}$.

Preparation of Blank Particles

Example 10

Preparation of blank particles BM-1 using DSP-1. The critical micelle concentration (CMC) value of DSP-1 was measured in deionized (DI) water by a LS50B luminescence spectrometer (Perkin Elmer, U.S.A) using pyrene as probe. Pyrene in acetone solution (10 μL, 6.16×10$^{-5}$ M) was added into glass vials. After the acetone was evaporated, polymer solution (1 mL) with various concentrations ranging from 0.01 to 2000 mg/L was added into each vial and mixed with pyrene by vortexing. After incubation overnight, the solutions were scanned from 300 to 360 nm with an emission wavelength of 395 nm to get the excitation spectra. Both excitation and emission bandwidths were set at 2.5 nm. The intensity ratios of $I_{337}/I_{334}$ obtained from the excitation spectra were used to plot a curve as a function of polymer concentration. The intersection of the tangent to the curve at the inflection and the tangent of the points at low polymer concentrations gave the CMC value. The CMC value of DSP-1 was 11.3 mg/L. For the in vitro study, BM-1 was prepared by combining DSP-1 (1.0 mg) in RPMI-1640 (1.0 mL) and gently vortexing 10 seconds at about 22° C. (room temperature). More dilute concentrations of BM-1 used for cytotoxicity testing of FIGS. 4 and 5 were obtained by diluting this sample.

Example 11

Preparation of blank particles BM-2 using DSP-2. Using the above procedure, the CMC of DSP-2 was determined to be 9.3 mg/L. For the in vitro study, BM-2 was prepared by combining DSP-2 (1.0 mg) in RPMI-1640 (1.0 mL) and gently vortexing 10 seconds at about 22° C. (room temperature). More dilute concentrations of BM-2 used for cytotoxicity testing (FIG. 7 below) were obtained by diluting this sample.

For the in vivo study, the blank particles were prepared by dissolving the polymers in saline directly.

Preparation of DOX-Loaded Particles and Measurement of DOX Loading

Examples 12-15

DOX-loaded particles of various DOX:COOH feed molar ratios were prepared using a sonication/membrane dialysis as described in YANG, et al., "Supramolecular nanostructures designed for high cargo loading capacity and kinetic stability", Nano Today, (2010), volume 5, pages 515-523. DOX-HCl was dissolved in N,N-dimethylacetamide (DMAc, 1.5 mL) and neutralized with trimethylamine (three moles excess). The polymer was dissolved in DMAc (0.5 mL) and mixed with the DOX solution by vortexing. The resulting solution was then added dropwise over 2 minutes to DI water (10 mL) while under sonication using a probe-based sonicator of 130 W (Vibra Cell VCX 130). Excess DOX and solvents were subsequently removed through dialysis against DI water (1000 mL) using a dialysis bag with molecular weight cut-off (MWCO) of 1000 Da (Spectra/Por 7, Spectrum Laboratories Inc.), and the water was changed at 2 hours, 5 hours, and 24 hours from the start of dialysis. DOX-loaded micellar solution inside the dialysis bag was collected at 48 hours and used for further studies or lyophilized for 2 days. Each experiment was performed in triplicates. The size of the micellar particles was measured using a particle sizer (Malvern (ZEN 3600) Zetasizer Nano ZS) prior to lyophilization. To determine the DOX content, 100 microliters of freshly prepared particles was diluted in dimethyl sulfoxide (DMSO, 900 microliters), or dried DOX-loaded particles (1 mg) was dissolved in DMSO (1 mL), and the absorbance of DOX in the solution was measured using a UV-Vis spectrophotometer (UV 2501 PC Shimadzu, Japan) at 480 nm. A standard curve was constructed to evaluate DOX concentration in the range of 1 to 1000 mg/L, and the r$^2$ value of the absorbance at 480 nm plotted linearly against DOX concentration in DMSO was at least 0.99. DOX loading was then assessed using the following formula:

$$DOX\ loading = \frac{Mass\ of\ DOX\ loaded\ in\ particles}{Mass\ of\ DOX\ loaded\ particles} \times 100\%$$

Encapsulation efficiency, the ratio of actual and original amount of DOX encapsulated in particles, was determined as follows:

$$Encapsulation\ efficiency = \frac{Actual\ amount\ of\ DOX\ loaded\ in\ particles}{Theoretical\ amount\ of\ DOX\ loaded\ in\ particles} \times 100\%$$

Table 1 lists the properties of disulfide-carboxylic polycarbonate particles (mean±standard deviation, n=3). DP is the degree of polymerization, mole ratio refers to feed mole ratio of DOX:COOH groups of the polycarbonate block.

TABLE 1

| Example | Loaded Particle Name | MPEG block (Mn) | Polymer Name | Feed Mole Ratio DOX:COOH | Particle size (nm) | PDI | DOX loading level (%) | Encapsulation efficiency (%) |
|---|---|---|---|---|---|---|---|---|
| 12 | LM-1 | 10000 | DSP-1 | 1 | 60 ± 9 | 0.14 ± 0.01 | 24.1 ± 1.6 | 68.3 ± 4.5 |
| 13 | LM-2 | 10000 | DSP-1 | 2 | 51 ± 3 | 0.10 ± 0.01 | 47.2 ± 1.5 | 90.6 ± 2.8 |
| 14 | LM-3 | 5000 | DSP-2 | 1 | 32 ± 1 | 0.08 ± 0.02 | 39.7 ± 0.5 | 89.7 ± 2.8 |
| 15 | LM-4 | 5000 | DSP-3 | 1 | 32 ± 1 | 0.25 ± 0.07 | 5.2 ± 0.7 | 15.1 ± 2.0 |

The average particle size of DOX-loaded particles LM-1, prepared from block polymer DSP-1 at DOX:COOH feed mole ratio of 1:1, was 60 nm. For LM-2, where the feed mole ratio was 2:1, the particle size was 51 nm. LM-1 and LM-2 also had a narrow size distribution (PDI=0.14 and 0.10, respectively). LM-1 (feed mole ratio 1:1) also achieved a high drug loading level of 24.1 wt %, attributed to the presence of ionic interactions between carboxylic acid groups in the polymer and amine group in DOX. Doubling the initial DOX:COOH mole ratio to 2 (LM-2) increased the final drug loading level by approximately 2-fold to 47.2%, possibly due to increased hydrophobic interactions between the DOX molecules. Although LM-2 had a higher drug loading level than LM-1, the average particle sizes were similar, suggesting that the particles prepared at feed mole ratio=2 (LM-2) had a more compact structure. The DOX encapsulation efficiency of LM-2 was 90.6%, considerably higher than LM-1 (68.3%).

The average particle size of LM-3, which utilized DSP-2, was 32 nm when the DOX:COOH feed mole ratio=1. This particle size is substantially smaller compared to LM-1 (60 nm). The smaller particle size is attributed to the shorter shell-forming PEG block of LM-3. LM-3 particles also had lower PDI (0.08), higher DOX loading level (about 40 wt %), and greater encapsulation efficiency (~90%) compared to LM-1 particles prepared at the same feed mole ratio=1. The increase in drug loading capacity of LM-3 may be explained by the relatively higher hydrophobicity of polymer DSP-2 compared to polymer DSP-1, resulting in stronger hydrophobic interactions between DOX and the micellar core comprising the more hydrophobic polycarbonate block.

For particles LM-4, which utilized DSP-3 having a polycarbonate block of DP=7 compared to DP=15 for DSP-2, the DOX loading level was about 8-fold less (5.2 wt %) compared to LM-3. These findings suggest that the polycarbonate block length, the PEG block length, and the initial DOX:COOH feed mole ratio, play important roles in affecting the particle size and the DOX loading level of the resultant particles. Because particles LM-1 to LM-3 had small particle sizes, narrow size distributions, and high drug loading levels compared to LM-4, particles LM-1 to LM-3 were selected for further studies.

In Vitro Release of DOX-Loaded Particles

The in vitro release of DOX from particles of polymers DSP-1 and DSP-2 was investigated in the simulated physiological environment of pH 7.4 and endosomal pH of 5.0. A concentration of 10 mM was used to mimic the cytoplasmic concentration of glutathione (GSH).

Figure 2:
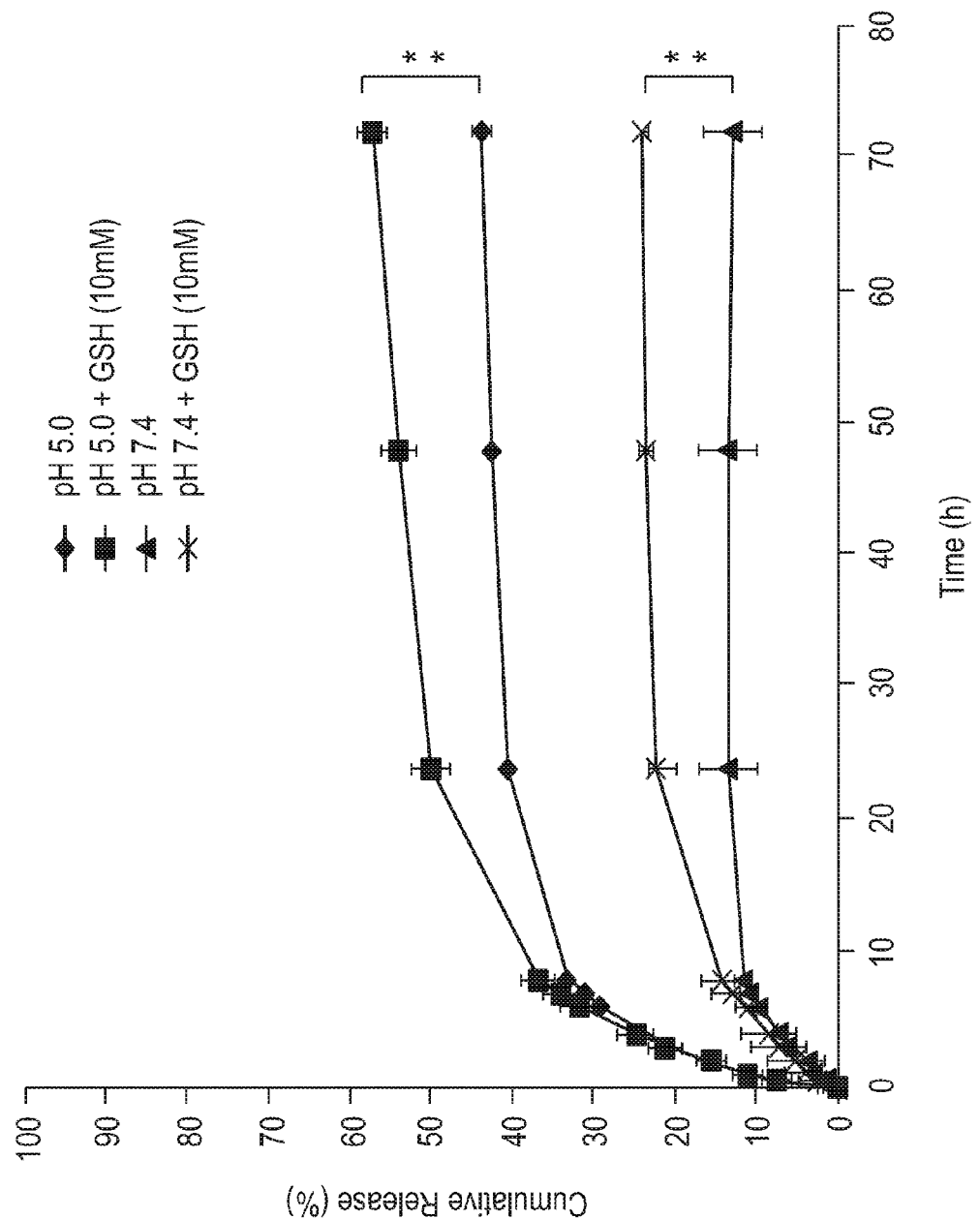
FIG. 2 is a graph showing the time-dependent cumulative release of DOX from loaded-particles LM-2 at pH 5.0 and 7.4, with and without GSH (mean±standard deviation, n=3, P value<0.01 at each pH).
Figure 3:
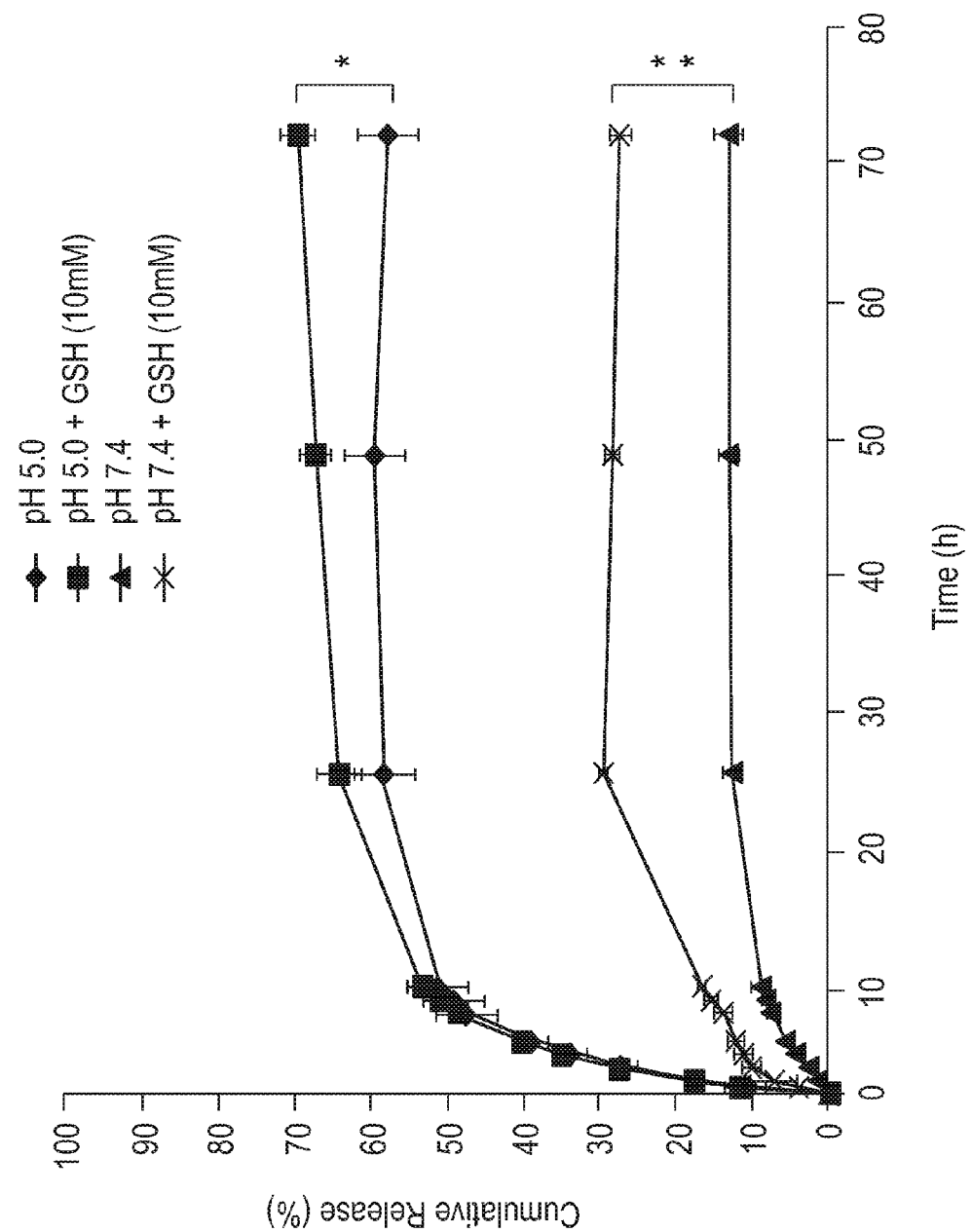
FIG. 3 is a graph showing the time-dependent cumulative release of DOX from loaded-particles LM-3 at pH 5.0 and 7.4, with and without GSH (mean±standard deviation, n=3, P value at pH 5.0<0.05, P value at pH 7.4<0.01).

FIG. 1 is a graph showing the time-dependent cumulative release of DOX from particles LM-1 (DSP-1, DOX:COOH feed mole ratio=1) at pH 5.0 and 7.0, with and without GSH (10 mM). FIG. 2 is a graph showing the time-dependent cumulative release of DOX from particles LM-2 (DSP-1, DOX:COOH feed mole ratio=2) at pH 5.0 and 7.0, with and without GSH (10 mM). FIG. 3 is a graph showing the time-dependent cumulative release of DOX from particles LM-3 (DSP-2, DOX:COOH feed mole ratio=1) at pH 5.0 and 7.0, with and without glutathione (GSH, 10 mM). Generally, a significant acceleration of DOX release was observed at pH 5.0 for the three particle types, where ~30%-40% of the encapsulated DOX was released within the first 8 hours for LM-1 and LM-2 particles, and approximately 50% DOX was released within 7 hours for LM-3 particles. Rapid release of DOX in an acidic environment is expected due to weakening of electrostatic interactions between amine group of DOX and acid group of polymers, which in turn, facilitates drug release. In addition, solubility of DOX increases in acidic pH (40, 41). On the other hand, within a period of 72 hours at the physiological pH of 7.4, about 10%-20% of the encapsulated DOX was released from LM-1 and LM-2 particles (FIGS. 1-2), and only ~8% from LM-3 particles (FIG. 3). These results demonstrate that drug release from the particles was pH-sensitive.

Addition of GSH at both pH 5.0 and pH 7.4 for the three particle types significantly enhanced the rate of DOX release at each pH, indicating that the particles were redox-responsive (FIGS. 1-3).

Although the effect of acidic pH was greater than the effect of added GSH, the highest DOX release was clearly observed for all particle types when the dual stimuli were applied concurrently (FIGS. 1-3). From the viewpoint of intracellular trafficking, DOX-loaded particles will first be exposed to an acidic environment (~pH 5.0) in the endosomes following cellular uptake through endocytosis. Exposure to protons would disrupt the ionic interactions between the amino group of DOX and carboxylate group, facilitating initial release of DOX. Subsequent entry of particles into the cytoplasm would then further release DOX when GSH cleaves the disulfide bonds.

Kinetic Stability

The kinetic stability of the DOX-loaded particles was evaluated by monitoring relative scattered light intensity change as a function of time using the particle sizer (Malvern (ZEN 3600) Zetasizer Nano ZS) in the presence of sodium dodecyl sulfate (SDS, 2.23 mg/mL), which acted as a destabilizing agent at room temperature.

Figure 4:
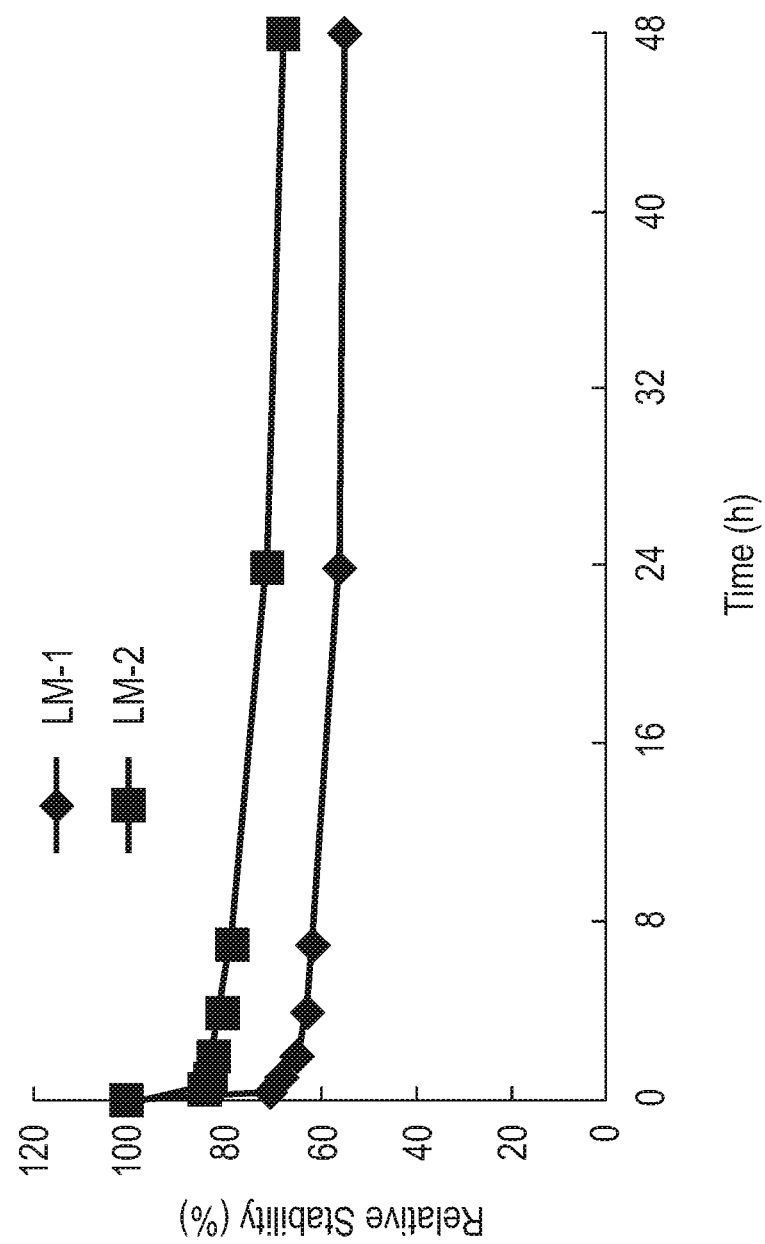
FIG. 4 is a graph showing the kinetic stability of loaded particles LM-1 and LM-2 in the presence of SDS.
Figure 5:
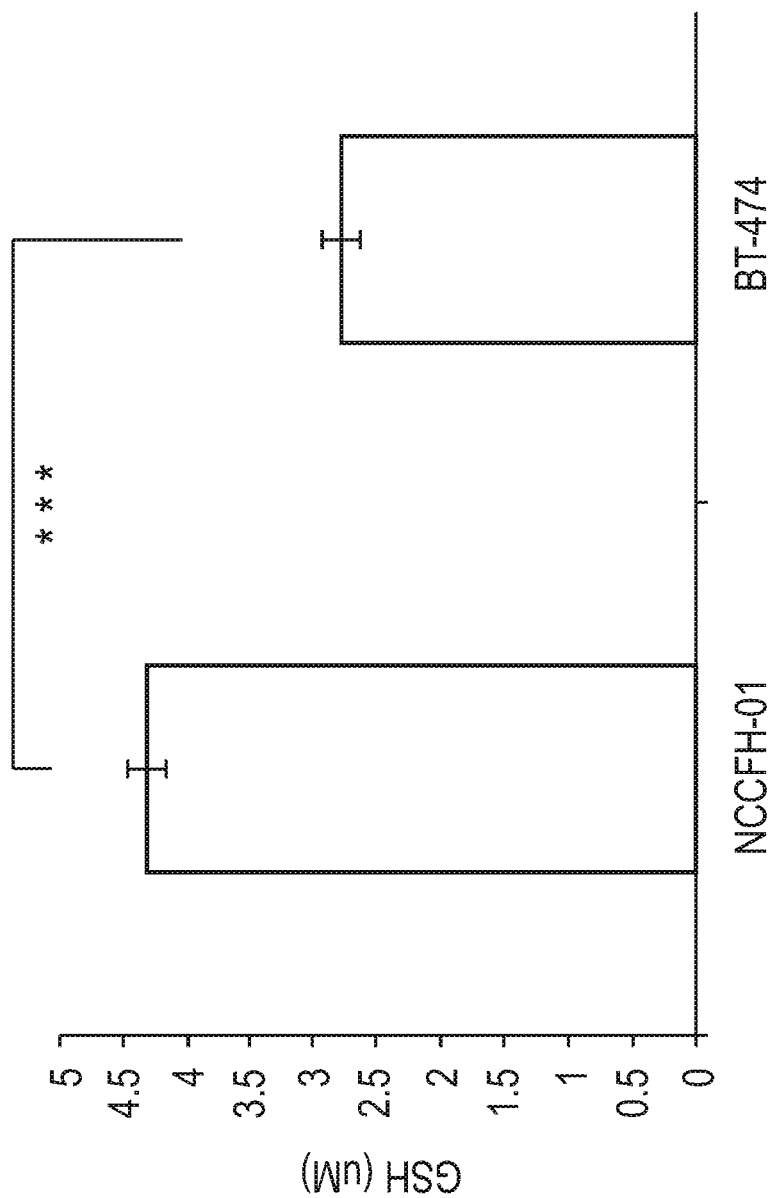
FIG. 5 is a bar graph showing levels of basal glutathione (GSH) in NCCFH-01 and BT-474 cells. Data are expressed as average±standard deviation (SD) of 3 independent experiments; P value<0.001.

FIG. 4 (graph) illustrates the kinetic stability of loaded particles LM-1 and LM-2 in the presence of SDS. The particles showed comparable stability, with the relative intensity leveling off at 54% for LM-1 and 68% for LM-2 at 48 hours. The slightly greater stability of LM-2 may be due to enhanced hydrophobic interactions between DOX and the particle core at higher DOX content.

Measurement of Intracellular GSH Levels

Intracellular glutathione levels were measured using the GSH-Glo Assay (Promega) and ratio of GSH to glutathione disulphide (GSSG) was quantified using the GSH/GSSG-Glo Assay (Promega). To quantify GSH, cells (BT-474 or NCCFH-01) were seeded at a density of $1 \times 10^4$ cells per well in 48-well plates and allowed to attach overnight, and then the cells were lysed. GSH was indirectly measured by the coupled conversion of luciferin-NT (derivative form) to luciferin in the presence of intracellular GSH, which produces luminescence by the activity of luciferase on luciferin. The luminescence was measured in a plate reader and luminescence units converted to glutathione concentration based on a standard curve.

The ratio of GSH:GSSG was measured similarly. Plates (48-well) were seeded with $1 \times 10^4$ cells per well. The cells were lysed the following day using the appropriate lysis buffer (which also converts GSSG to GSH) with or without N-ethylmaleimide (which blocks sulfhydryl groups of free cysteine of GSH). The subsequent reaction similarly quantifies total glutathione (GSH+GSSG) or GSSG based on luminescence production. The ratio of GSH to GSSG was calculated from the luminescence of distinct cell samples used for GSH+GSSG and GSSG quantifications.

Figure 6:
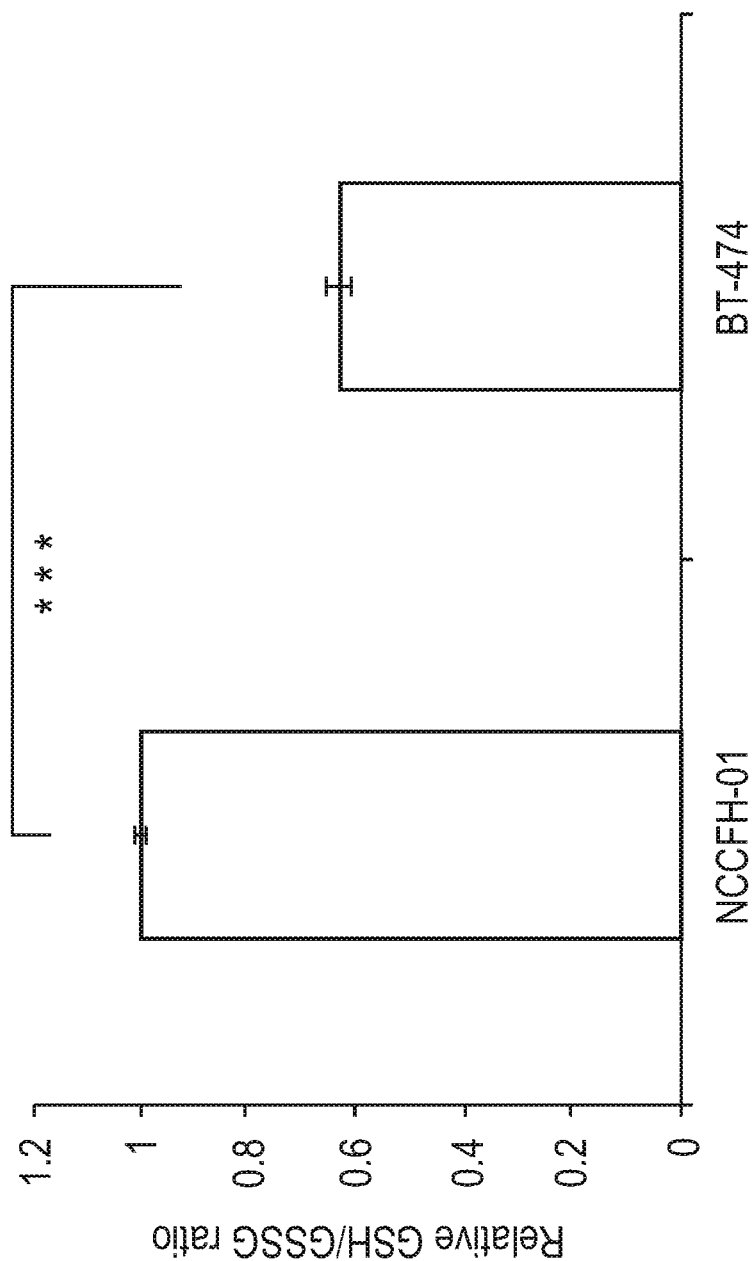
FIG. 6 is a bar graph showing the relative ratio of glutathione (GSH) to glutathione disulphide (GSSG) in NCCFH-01 and BT-474 cells. Data are expressed as average±SD of 3 independent experiments; P value<0.001.

Baseline levels of intracellular glutathione (GSH) were measured in NCCFH-01 and BT-474 cells to assess the contribution of GSH to the activity of the drug-loaded particles in each cell line. Measurements of intracellular GSH and GSSG showed that NCCFH-01 cells had higher levels of GSH (FIG. 5, bar graph) and also maintained a significantly higher ratio of GSH to GSSG (FIG. 6, bar graph) compared to BT-474 cells. These results are in agreement with previous studies suggesting that human cells lacking fumarate hydratase have increased pools of GSH. This suggests that the larger pool of GSH in NCCFH-01 cells may result in a greater release of drug from the drug-loaded particle in NCCFH-01 cells compared to BT-474 cells.

In Vitro Cytotoxicity

Cytotoxicity of free DOX, DOX-loaded particles, and blank particles was determined through MTT assay. BT-474 cells and NCCFH-01 cells were seeded into 96-well plates at a density of $5 \times 10^3$ cells per well and incubated overnight in 100 microliters of RPMI-1640 containing 25 mM Hepes and L-Glutamine, supplemented with 10% FBS and 5% penicillin-streptomycin at 37 C, 5% $CO_2$. Free DOX, freshly prepared DOX-loaded particles (against BT-474 cells), lyophilized DOX-loaded particles (against NCCFH-01 cells) and blank particles were dissolved in RPMI-1640 at various concentrations. The sample solution (100 microliters) was used to replace the medium in each well and the plates were incubated at 37 C, 5% $CO_2$ for 48 h. Six replicates were tested for each concentration and only RPMI was added for control. At the end of 48 h treatment, each sample solution was substituted with 100 microliters of fresh RPMI-1640 and 20 microliters of MTT solution (5 mg/mL in PBS). The plates were then maintained at 37 C, 5% $CO_2$ for 4 h. Subsequently, the medium solution was removed and DMSO (150 microliters) was added to each well to dissolve the purple formazan crystals internalized by live cells. After gentle agitation for 15 minutes, the absorbance of formazan crystals was taken to be that at 550 nm subtracted by that at 690 nm (TECAN, Switzerland). Cell viability was expressed as a percentage of absorbance of the control cells.

Figure 7:
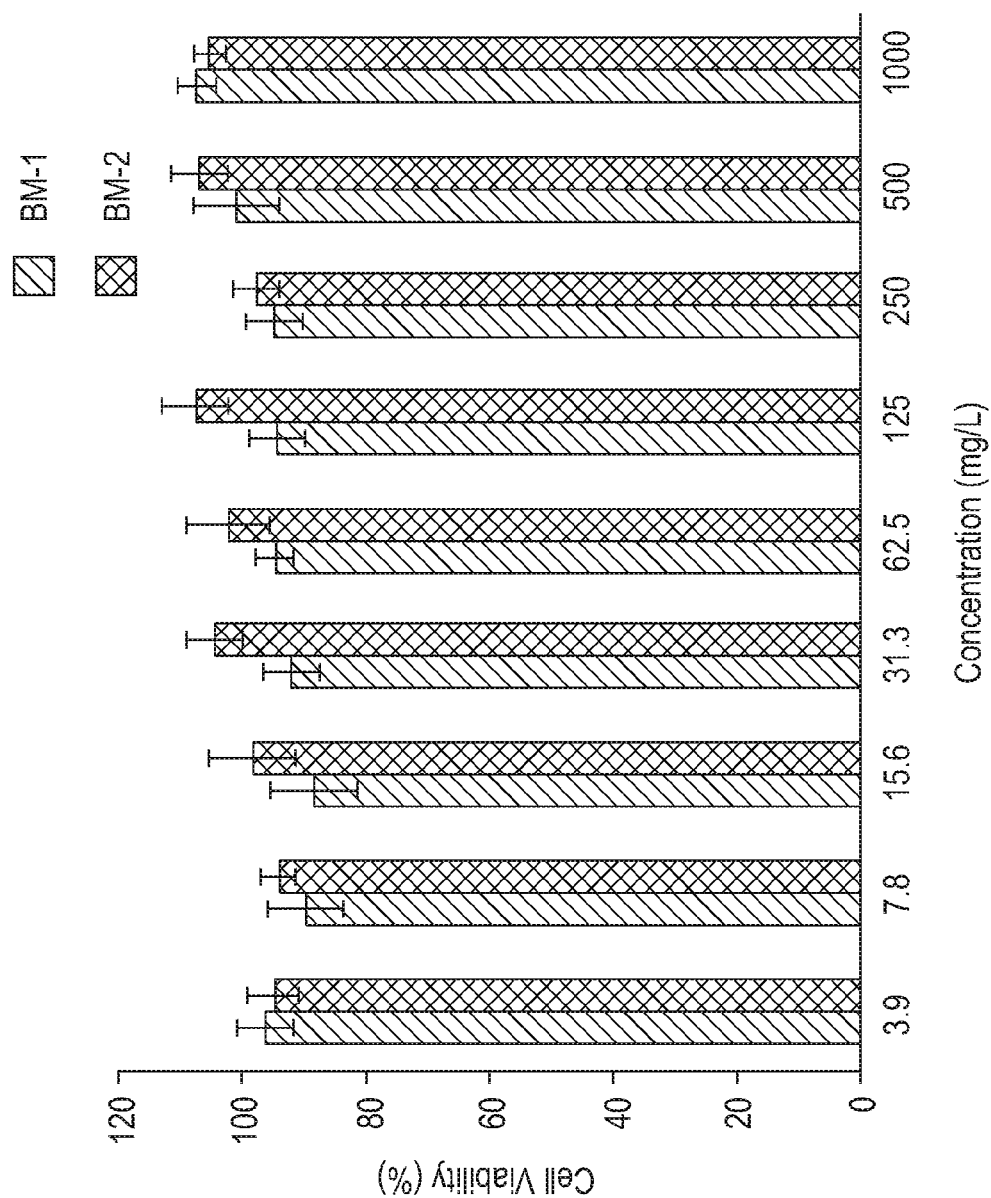
FIG. 7 is a bar graph showing the viability of human breast cancer cells BT-474 after 48 hour incubation with blank particles BM-1 and BM-2.
Figure 8:
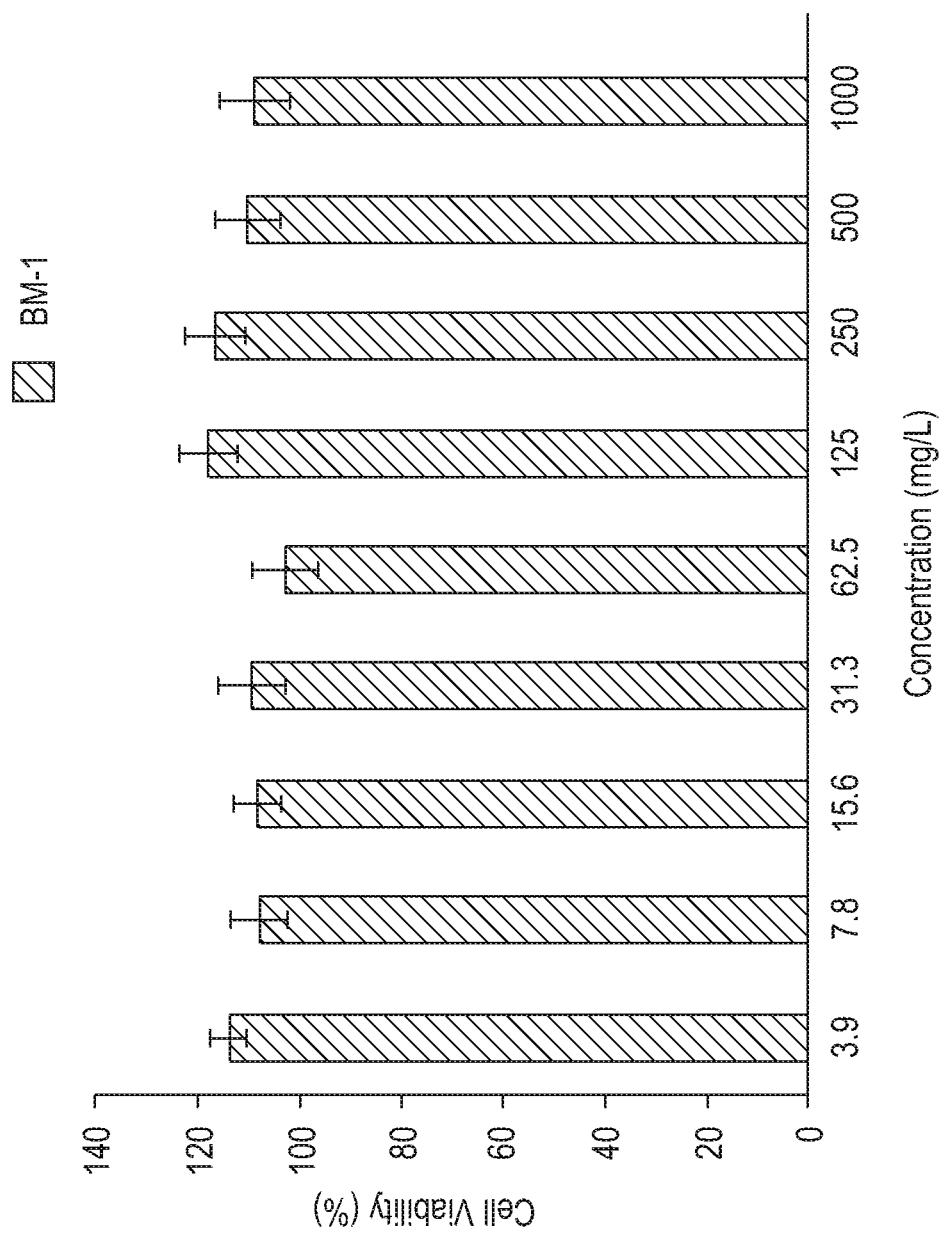
FIG. 8 is a bar graph showing the viability of hereditary leiomyomastosis and renal cancer cells (NCCFH-01 cell line) after 48 hour incubation with blank particles BM-1.

FIG. 7 is a bar graph showing the viability of BT-474 cells after incubation with blank particles BM-1 (DSP-1) and BM-2 (DSP-2) at 37° C. and pH 7.4 for 48 hours. FIG. 8 is a bar graph showing the viability of NCCFH-01 cells after incubation with blank particles BM-1 (DSP-1) at 37° C. and pH 7.4 for 48 hours. No significant cytotoxicity was observed against either cell line. More than 85% of the BT-474 cells and NCCFH-01 cells survived a 48 hour incubation with BM-1 and BM-2 particles at the highest particle concentration (1000 mg/L).

Figure 9:
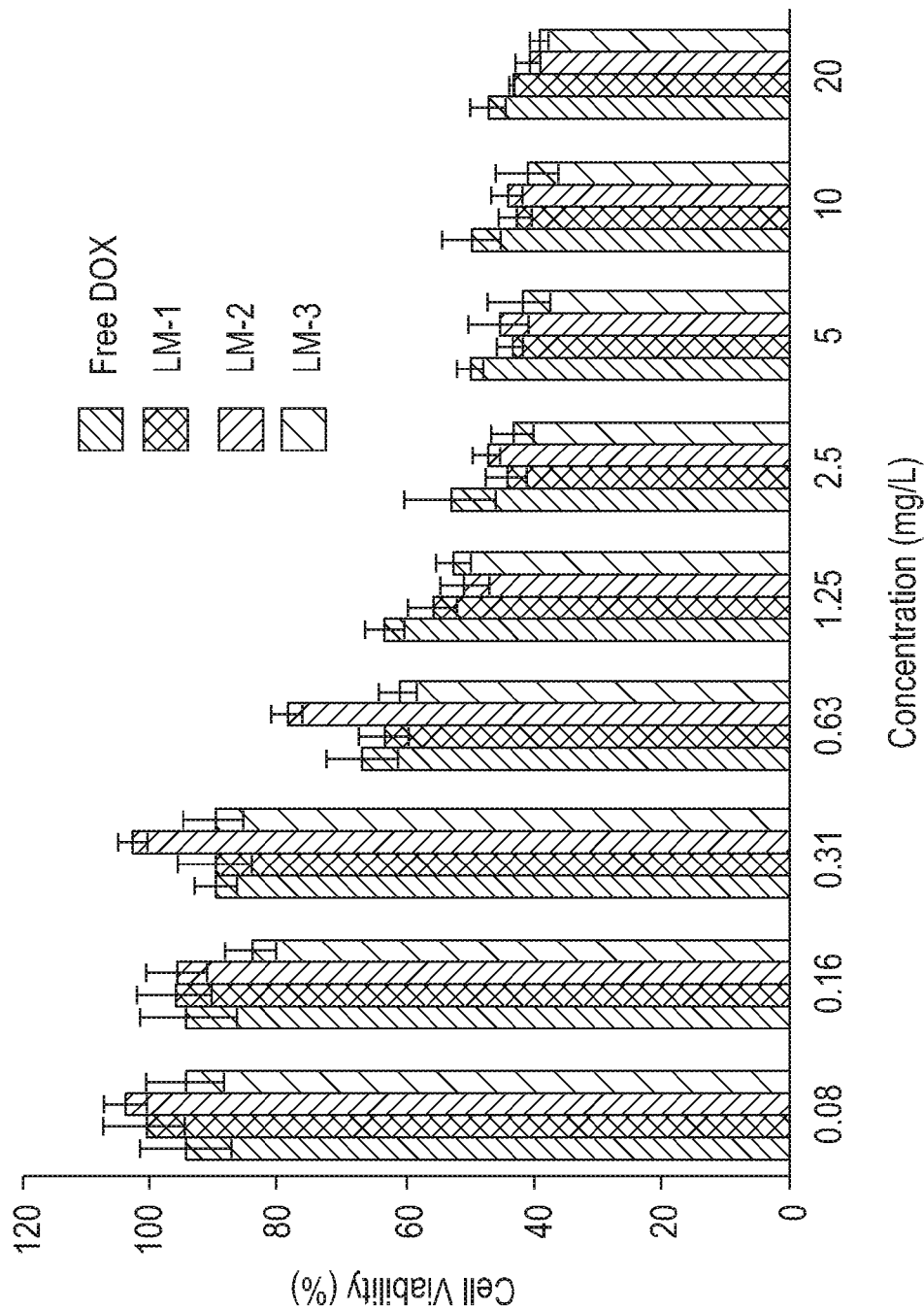
FIG. 9 is a bar graph showing the viability of human breast cancer cells (BT-474 cell line) after 48 hour incubation at 37° C. and pH 7.4 with free DOX, and loaded particles LM-1, LM-2, and LM-3.

FIG. 9 is a bar graph showing the viability of BT-474 cells after incubation 48 hours with DOX, DOX-loaded particles LM-1 (DSP-1, feed mole ratio 1), LM-2 (DSP-1, feed mole ratio 2), and LM-3 (DSP-2, feed mole ratio 1) at 37° C. and pH 7.4 for 48 hours. Similar cytotoxicity trends were observed for free DOX and DOX loaded particles LM-1, LM-2, and LM-3. This indicates the DOX-loaded polymer particles effectively released the DOX and were able to suppress the proliferation of BT-474 cells over a period of 48 hours.

Figure 10:
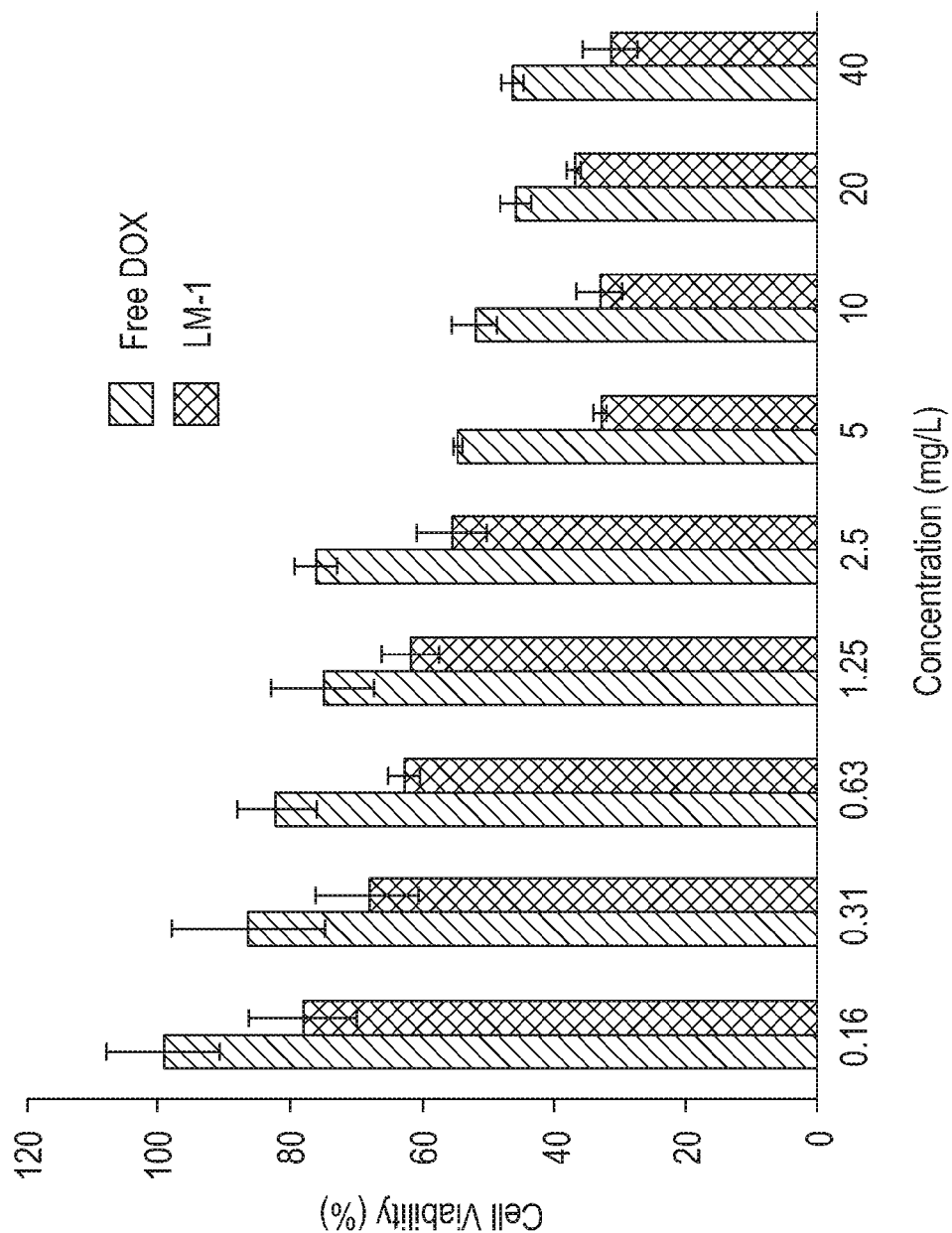
FIG. 10 is a bar graph showing the viability of NCCFH-01 cells after 48 hour incubation at 37° C. and pH 7.4 with free DOX, and loaded particles LM-1.

FIG. 10 is a bar graph showing the viability of NCCFH-01 cells after incubation 48 hours with DOX and, loaded particles LM-1 (DSP-1, feed mole ratio 1) at 37° C. and pH 7.4 for 48 hours. The toxicity of DOX-loaded particles LM-1 against NCCFH-01 cells was several-fold higher than for free DOX. The half maximal inhibitory concentration $IC_{50}$ of the DOX-loaded particles was 2.9 mg/L, and that of free drug was 12.7 mg/L. Given the deficiency of fumarate hydratase in NCCFH-01 cells, which leads to higher lactate production and lower pH, DOX release from particles might be enhanced in the NCCFH-01 cells.

In Vivo Antitumor Efficacy

Female BALB/c nude mice were provided by Singapore Biological Research Center (BRC) at 6 weeks of age (20-22 g). All animal studies were adhered to protocols approved by the Singapore BRC's Institutional Animal Care and Use Committee. BT-474 cells ($1 \times 10^7$) were suspended in 200 microliters of a solution containing Matrigel and PBS (volume ratio: 50/50) and subcutaneously injected into the right flank of female BALB/c nude mice. Estradiol pellet (0.72 mg/pellet, 60 days release) was subcutaneously administered into mice one day before the inoculation. Once the tumor volume reached about 200 $mm^3$ on the 14th day (recorded as day 0), the mice were randomly divided into 5 groups (7-8 animals per group): group 1 for 0.9% saline as control, group 2 for blank particles, group 3 for free DOX, group 4 for DOX-loaded particles LM-1, and group 5 for DOX-loaded particles LM-2. The dose of DOX in all formulations was 5 mg/kg. The formulations were given to mice via tail vein injection at day 0, 3, 6 and 10. At the predetermined time points, mice were weighed and tumor size was measured with a Vernier caliper. The tumor volume was calculated using the following formula: Tumor volume=length×width$^2$/2.

Figure 11:
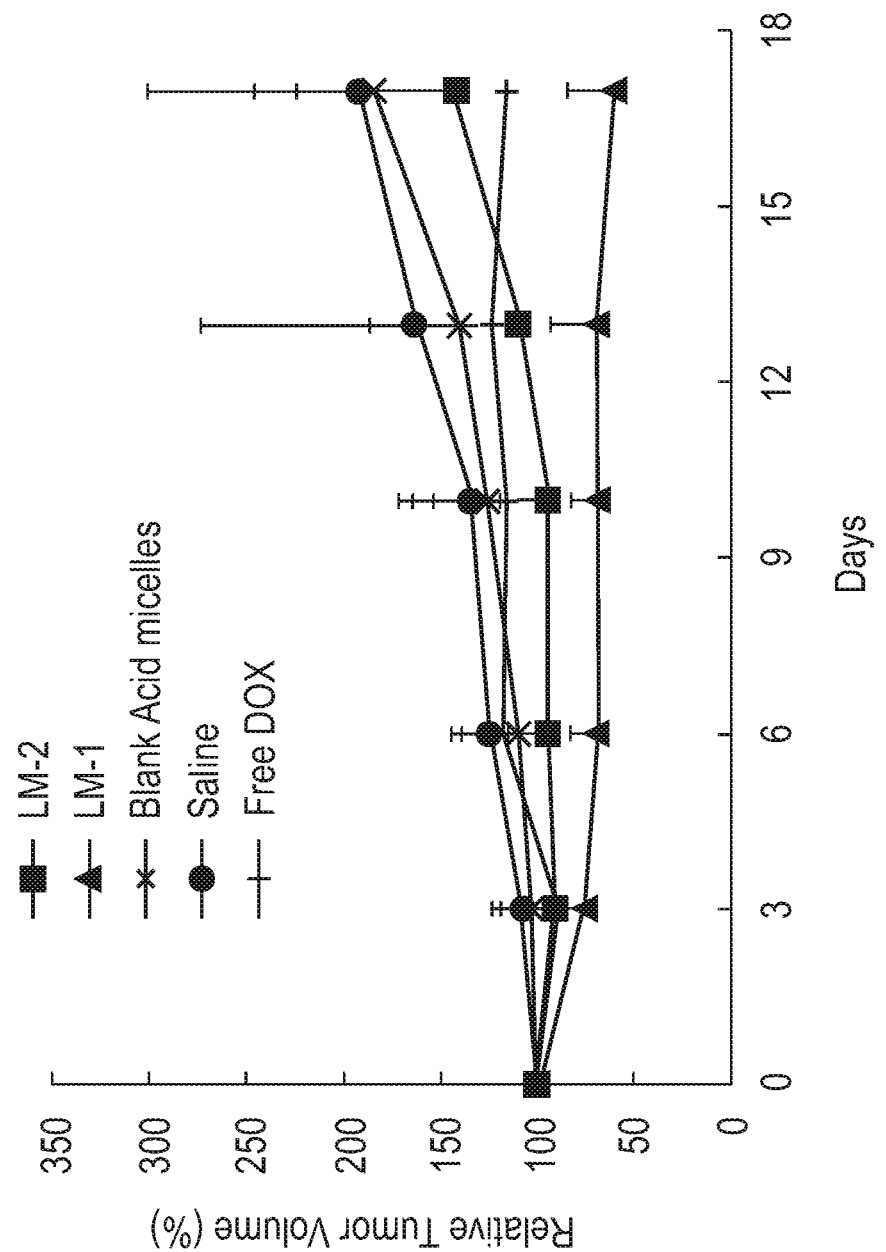
FIG. 11 is a graph showing the in vivo antitumor effect in terms of tumor volume change of various formulations in nude mice bearing BT-474 xenografts: 0.9% saline, blank particles BM-1, free DOX (5 mg/kg), DOX-loaded particles LM-1 (5 mg/kg), and DOX-loaded particles LM-2 (5 mg/kg); P value<0.01, LM-1 versus other groups.

FIG. 11 (graph) shows the relative tumor volume changes following the treatment with various formulations in nude mice bearing BT-474 xenografts. The LM-1 particles showed stronger antitumor efficacy than free DOX, which may be due to the enhanced permeability and retention (EPR) effect of the self-assembled particles. At the same time, the LM-1 particles showed stronger antitumor activity than LM-2 particles, which might be due to the higher drug loading level of LM-2, which might have limited the number of particles reaching the tumor site, resulting in less tumor uptake compared to LM-1 particles. The blank particles did not show any antitumor efficacy, indicating that the antitumor activity of various DOX-loaded particles came from DOX.

Figure 12:
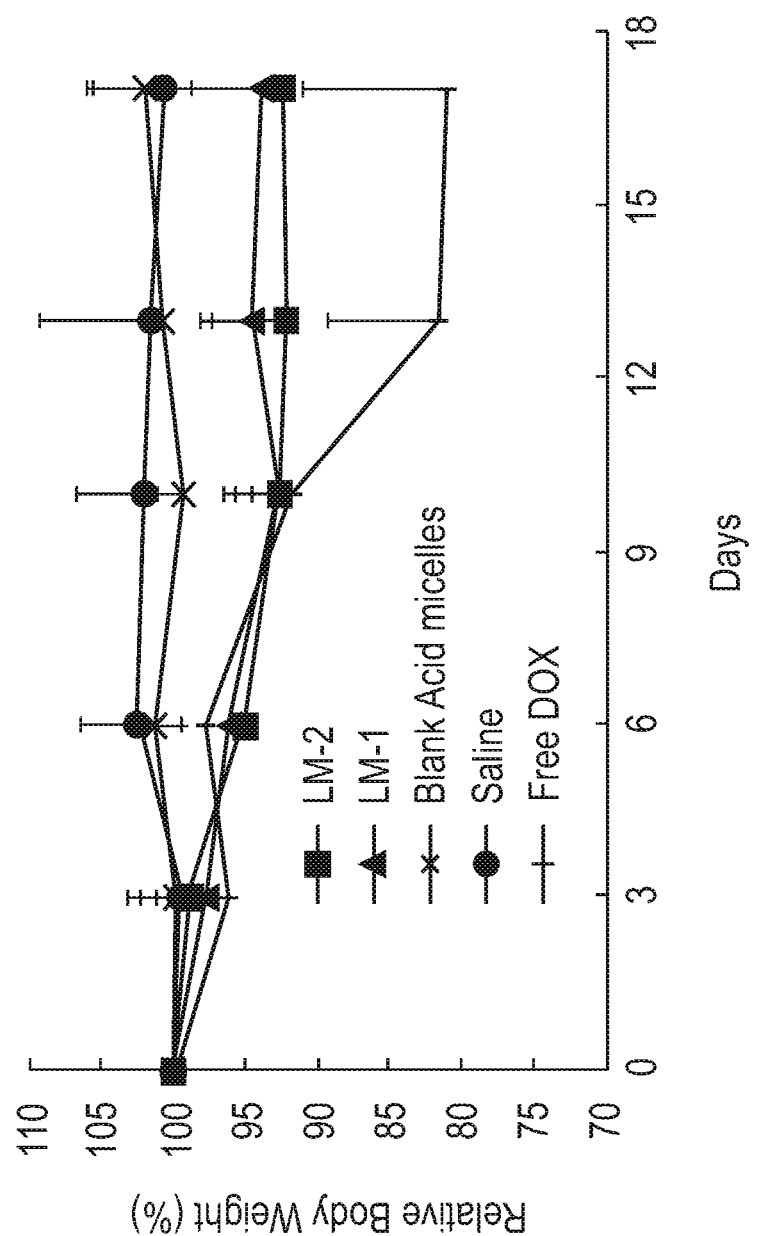
FIG. 12 is a graph showing the change in mouse body weight during the in vivo treatments; P value<0.01, free DOX versus other groups.

In addition, DOX-loaded particles did not cause significant body weight loss, while the treatment with free DOX led to 20% weight loss (FIG. 12, graph). This finding indicated that the particles were capable of mitigating the toxicity of free DOX.

CONCLUSIONS

Diblock copolymers comprising a PEG block and biodegradable polycarbonate block functionalized with disulfide bonds and carboxylic acid groups were synthesized. The block copolymers form self-assembled particles in aqueous solution that can be loaded with hydrophobic drugs for therapeutic drug delivery. The loaded particles have small particle sizes (<100 nm), narrow particle size distributions, and high drug loading capacity. The higher the feeding molar ratio of DOX to carboxylic acid group, the higher the drug loading, up to about 50 wt % loading, based on total dry weight of the loaded particle. In particular, particles loaded with DOX have been shown to release the DOX in response to changes in pH and glutathione (GSH) redox chemistry. The loaded particles efficiently delivered and released DOX within cancer cells. At the endosomal pH of 5.0 and in the presence of GSH at the cytoplasmic concentration, drug release was significantly accelerated. Most importantly, while blank particles (containing no therapeutic agent) did not induce cytotoxicity to cells, DOX-loaded particles were able to effectively suppress growth of tumor cells at a similar or even lower drug concentration than free DOX. Given their superior antitumor activity, these pH and redox dual-responsive biodegradable particles are promising carriers of anti-cancer drugs for targeted drug delivery.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A block copolymer (BCP), comprising:
i) a hydrophilic block A having a structure according to formula (A-1):

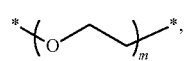

wherein m represents average degree of polymerization (DP), and m has a value greater than 1; and ii) a block B which comprises an aliphatic carbonate repeat unit of formula (A-2):

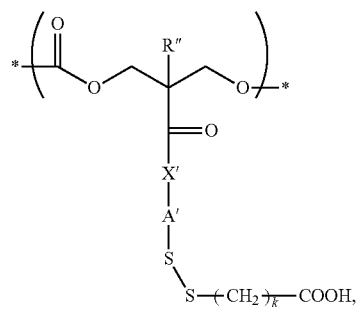

wherein
k is a positive integer having a value of 2-10,
A' is a divalent hydrocarbon linking group comprising 2-10 carbons,
R" is a monovalent radical selected from the group consisting of hydrogen, methyl, ethyl, and propyl, and
X' is *—O—* or *—NH—*;
wherein
the BCP is a linear block copolymer,
block B is a polycarbonate chain or a polyestercarbonate chain, and
an end repeat unit of block A is directly covalently linked to an end repeat unit of block B by a single bond, or is indirectly covalently linked to an end repeat unit of block B by a divalent linking group L' comprising 0-20 carbons.

2. The BCP of claim 1, wherein the block copolymer is a diblock copolymer, and block B is a polycarbonate chain of formula (A-3):

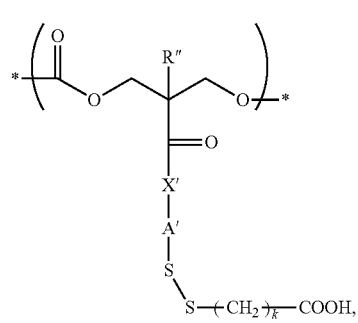

wherein
n represents average degree of polymerization, and n has a value between 1 and 100,
each k is an independent positive integer having a value of 2-10,
each A' is an independent divalent hydrocarbon group comprising 2-10 carbons,
each R" is an independent monovalent radical selected from the group consisting of hydrogen, methyl, ethyl, and propyl, and
each X' is an independent member of the group consisting of *—O—* and *—NH—*.

3. The BCP of claim 1, wherein the block copolymer is a B-A-B-type triblock copolymer comprising a second block B, wherein the second block B comprises an aliphatic carbonate repeat unit of formula (A-2), and an end repeat unit of the second block B is directly covalently linked to a second end repeat unit of block A by a single bond, or is indirectly covalently linked to a second end repeat unit of block A by a divalent linking group L" comprising 0-20 carbons.

4. The BCP of claim 1, wherein the block copolymer is an A-B-A-type triblock copolymer comprising a hydrophilic second block A having a structure of formula (A-1), wherein an end repeat unit of the second block A is directly covalently linked to a second end repeat unit of block B by a single bond, or is indirectly covalently linked to a second end repeat unit of block B by a divalent linking group L" comprising 0-20 carbons.

5. The BCP of claim 1, wherein the carbonate repeat unit has the structure:

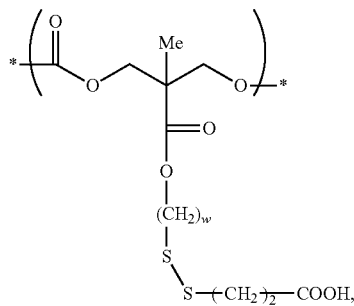

wherein w is an independent positive integer having a value of 2-10.

6. The BCP of claim 1, wherein the carbonate repeat unit has the structure:

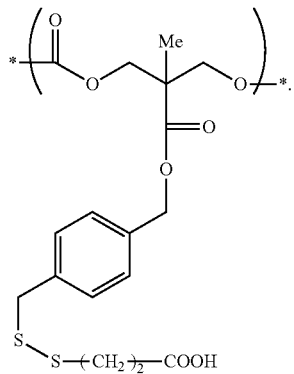

7. The BCP of claim 1, wherein the BCP is capable of self-assembling in water, thereby forming particles dispersed in the water, the particles comprising two or more macromolecules of the BCP bound by non-covalent interactions.

8. A composition comprising:
water; and
loaded particles dispersed in the water, wherein each of the loaded particles comprises two or more macromolecules of the BCP of claim 1 and a therapeutic agent for a medical treatment, the BCP and the therapeutic agent bound by non-covalent interactions;
wherein
the therapeutic agent is selected from the group consisting of genes, proteins, peptides, drugs, and combinations thereof, the loaded particles have an average cross-sectional circular diameter of about 10 nm to about 500 nm, and
the loaded particles are capable of releasing the therapeutic agent in response to a change in pH and/or reaction with a disulfide reducing agent.

9. The composition of claim 8, wherein the disulfide reducing agent is glutathione (GSH).

10. The composition of claim 8, wherein the particles are capable of delivering the therapeutic agent to a cell, transporting the therapeutic agent through a membrane of the cell, and releasing the therapeutic agent within the cell in response to an intracellular change in pH and/or reaction with an intracellular disulfide reducing agent.

11. The composition of claim 8, wherein the therapeutic agent is a drug.

12. The composition of claim 11, wherein the drug is a cancer drug.

13. The composition of claim 11, wherein the cancer drug is doxorubicin.

14. The composition of claim 8, wherein the therapeutic agent is an antimicrobial agent.

15. The composition of claim 8, wherein the loaded particles have an average cross-sectional circular diameter of 10 nm to 100 nm.

16. The composition of claim 8, wherein the composition is capable of being administered by injection.

17. A method of forming the BCP of claim 1, comprising:
preparing an initial block copolymer by organocatalyzed ring opening polymerization (ROP) of a cyclic carbonate monomer comprising a pendent leaving group, the ROP initiated by a polymeric initiator comprising a poly(ethylene oxide) chain, the initial block copolymer comprising a poly(ethylene oxide) chain designated block A and a second block comprising an aliphatic carbonate repeat unit comprising a sidechain leaving group, wherein an end repeat unit of block A is directly covalently linked to an end repeat unit of the second block by a single bond, or is indirectly covalently linked to an end repeat unit of the second block by a divalent linking group L' comprising 0-20 carbons;
treating the initial block copolymer with a compound comprising a thiosulfonate anion, thereby forming a modified block copolymer by nucleophilic substitution of the leaving group by the thiosulfonate anion, the modified block copolymer comprising a carbonate repeat unit comprising a sidechain thiosulfonate group; and
treating the modified block copolymer with a compound comprising a thiol group and a carboxylic acid group, thereby forming the BCP of claim 1.

18. The method of claim 17, wherein the cyclic carbonate monomer has a structure according to formula (A-15):

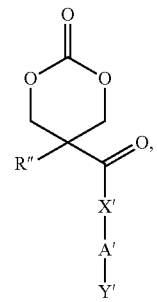

wherein
- A' is a divalent hydrocarbon linking group comprising 2-10 carbons,
- R" is a monovalent radical selected from the group consisting of hydrogen, methyl, ethyl, and propyl,
- X' is *—O—* or *—NH—*, and
- Y' is a monovalent leaving group capable of undergoing a nucleophilic substitution reaction with a thiosulfonate anion.

19. The method of claim 17, wherein the cyclic carbonate monomer is MTC-PrCl:

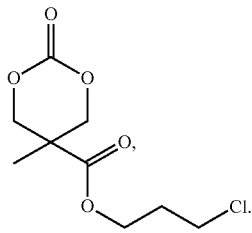

20. The method of claim 17, wherein the cyclic carbonate monomer is MTC-BnCl:

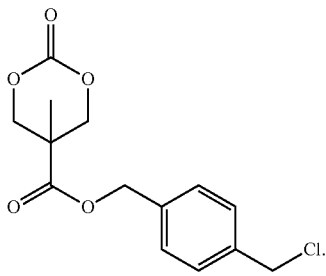

21. The method of claim 17, wherein the carbonate repeat unit of the initial block copolymer has a structure according to formula (A-16):

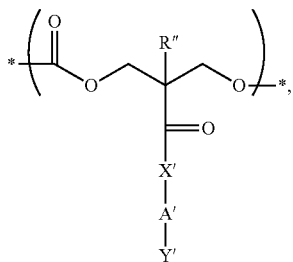

(A-16)

wherein
- A' is a divalent hydrocarbon linking group comprising 2-10 carbons,
- R" is a monovalent radical selected from the group consisting of hydrogen, methyl, ethyl, and propyl,
- X' is *—O—* or *—NH—*, and
- Y' is a monovalent leaving group capable of undergoing a nucleophilic substitution reaction with a thiosulfonate anion.

22. The method of claim 17, wherein the carbonate repeat unit of the modified block copolymer has a structure according to formula (A-19):

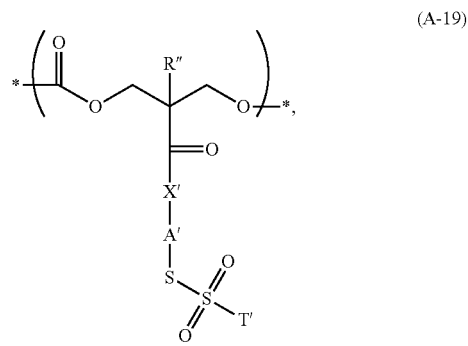

(A-19)

wherein
- A' is a divalent hydrocarbon linking group comprising 2-10 carbons,
- R" is a monovalent radical selected from the group consisting of hydrogen, methyl, ethyl, and propyl,
- X' is *—O—* or *—NH—*, and
- T' is a monovalent $C_1$-$C_{10}$ hydrocarbon group.

23. The method of claim 17, wherein the ROP is initiated by a mono-endcapped poly(ethylene glycol), and the BCP is a diblock copolymer.

24. The method of claim 17, wherein the ROP is initiated by poly(ethylene glycol), the BCP is a triblock copolymer comprising said block A, said block B, and an independent third polymer block designated block B', wherein i) block B' comprises an aliphatic carbonate repeat unit comprising a disulfide group and a carboxyl acid group and ii) a second end unit of block A is directly covalently linked to an end repeat unit of block B' by a single bond, or is indirectly covalently linked to an end repeat unit of block B' by a divalent linking group L" comprising 0-20 carbons.

25. The method of claim 17, wherein the initial block copolymer is treated with an endcap agent comprising a poly(ethylene oxide) chain, the BCP is a triblock copolymer comprising an independent third polymer block designated block A', wherein i) block A' comprises the poly(ethylene oxide) chain of the endcap agent and ii) a second end unit of block B is directly or indirectly covalently linked to an end repeat unit of block A' by a single bond, or is indirectly covalently linked to an end repeat unit of block A' by a divalent linking group L" comprising 0-20 carbons.

* * * * *